US012600715B2

(12) United States Patent
Flack et al.

(10) Patent No.: US 12,600,715 B2
(45) Date of Patent: Apr. 14, 2026

(54) SOLUBLE GUANYLATE CYCLATE ACTIVATORS FOR TREATING SYSTEMIC SCLEROSIS

(71) Applicant: Boehringer Ingelheim International GmbH, Ingelheim am Rhein (DE)

(72) Inventors: Mary Ruth Flack, New York, NY (US); Julia Kaufman, Eastchester, NY (US); Indra Sethy-Coraci, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 288 days.

(21) Appl. No.: 18/386,267

(22) Filed: Nov. 2, 2023

(65) Prior Publication Data

US 2024/0174653 A1 May 30, 2024

Related U.S. Application Data

(60) Provisional application No. 63/422,452, filed on Nov. 4, 2022.

(51) Int. Cl.

*C07D 405/14* (2006.01)
*A61P 11/00* (2006.01)
*A61P 17/00* (2006.01)

(52) U.S. Cl.

CPC ............ *C07D 405/14* (2013.01); *A61P 11/00* (2018.01); *A61P 17/00* (2018.01)

(58) Field of Classification Search

CPC ........ C07D 405/14; A61P 11/00; A61P 17/00; A61P 17/02; A61P 29/00; A61P 37/00; A61K 31/553; A61K 31/4725

See application file for complete search history.

(56) References Cited

U.S. PATENT DOCUMENTS

| | | | |
|---|---|---|---|
| 2,429,312 A | 10/1947 | Pharma | |
| 8,569,339 B2 | 10/2013 | Brenneman et al. | |
| 8,906,904 B2 | 12/2014 | Brenneman et al. | |
| RE46,886 E | 6/2018 | Brenneman et al. | |
| 11,690,848 B2 * | 7/2023 | Ertle .................... | A61K 31/505 514/229.2 |
| 2002/0173514 A1 | 11/2002 | Stasch et al. | |
| 2009/0209556 A1 | 8/2009 | Bittner et al. | |
| 2010/0016305 A1 | 1/2010 | Krahn et al. | |
| 2010/0216764 A1 | 8/2010 | Kim et al. | |
| 2010/0257638 A1 | 10/2010 | Cai et al. | |
| 2013/0065918 A1 | 3/2013 | Brenneman et al. | |
| 2013/0158028 A1 | 6/2013 | Stasch et al. | |
| 2013/0203729 A1 | 8/2013 | Bosanac et al. | |
| 2014/0073629 A1 | 3/2014 | Brenneman et al. | |
| 2019/0371469 A1 | 12/2019 | Sandner et al. | |

FOREIGN PATENT DOCUMENTS

| | | | |
|---|---|---|---|
| CA | 2720343 | A1 | 10/2009 |
| EP | 2594270 | A2 | 5/2013 |
| JP | 2003274950 | A | 9/2003 |
| JP | 20105000029 | | 2/2008 |
| WO | 2002026712 | A2 | 4/2002 |
| WO | 2003101959 | A1 | 12/2003 |
| WO | 2004058176 | A2 | 7/2004 |
| WO | 2002043201 | | 12/2005 |
| WO | 2008021207 | A2 | 2/2008 |

(Continued)

OTHER PUBLICATIONS

Nagaraja, Vivek et al. "A multicenter randomized, double-blind, placebo-controlled pilot study to assess the efficacy and safety of riociguat in systemic sclerosis-associated digital ulcers" (2019) 21:202, 14 pgs.

Neuen, Brendon L et al."Sodium-Glucose Cotransporter 2 Inhibitors and Risk of Hyperkalemia in People With Type 2 Diabetes: A Meta-Analysis of Individual Participant Data From Randomized, Controlled Trials" (2022) Circulation, 145, 1460-1470.

Notice of Allowance mailed May 23, 2014 for US Patent U.S. Appl. No. 13/570,432, filed Aug. 9, 2012, (Boehringer Ingelheim Docket No. 09-0574), Inventor: Todd BOSANAC.

(Continued)

*Primary Examiner* — Joseph K McKane
*Assistant Examiner* — Meghan C Heasley
(74) *Attorney, Agent, or Firm* — David L. Kershner

(57) ABSTRACT

The present invention relates to methods for treating patients with systemic sclerosis, comprising administering to a patient in need thereof a therapeutically effective amount of a soluble guanylate cyclase (sGC) activator of formula (I), (I)

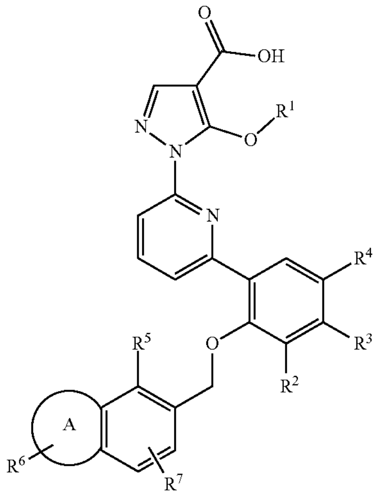

or a pharmaceutically acceptable salt thereof, where $R^1$-$R^7$ and A are as defined herein.

20 Claims, 10 Drawing Sheets

(56) References Cited

FOREIGN PATENT DOCUMENTS

| | | | |
|---|---|---|---|
| WO | 2008021339 | A2 | 2/2008 |
| WO | 2008138483 | A1 | 11/2008 |
| WO | 2009032249 | A1 | 3/2009 |
| WO | 2009068652 | A1 | 6/2009 |
| WO | 2009071504 | A1 | 6/2009 |
| WO | 2010015652 | A2 | 2/2010 |
| WO | 2010015653 | A1 | 2/2010 |
| WO | 2010065275 | A1 | 6/2010 |
| WO | 2010099054 | A2 | 9/2010 |
| WO | 2011095534 | A1 | 8/2011 |
| WO | 2011095553 | A1 | 8/2011 |
| WO | 2011147810 | A1 | 12/2011 |
| WO | 2011161099 | A1 | 12/2011 |
| WO | 2012058132 | A1 | 5/2012 |
| WO | 2012122340 | A1 | 9/2012 |
| WO | 2013025425 | A1 | 2/2013 |
| WO | 2014039434 | A1 | 3/2014 |
| WO | 2016014463 | A1 | 1/2016 |
| WO | 2016177660 | A1 | 11/2016 |
| WO | 2017200857 | A1 | 11/2017 |
| WO | 2020011804 | A1 | 1/2020 |

OTHER PUBLICATIONS

Pope, Janet "Measures of Systemic Sclerosis (Scleroderma) Health Assessment Questionnaire (HAQ) andScleroderma Haq (Shaq), Physician- and Patient-Rated Global Assessments, Symptom Burden Index (SBI), University of California, Los Angeles, Scleroderma Clinical Trials Consortium Gastrointestinal Scale (Ucla Sctc Git) 2.0, Baseline Dyspnea Index (BDI) and Transition Dyspnea Index (TDI) (Mahler's Index), Cambridge Pulmonary Hypertension Outcome Review (CAMPHOR), and Raynaud's Condition Score (RCS)" (2011) Arthritis Care &.

Reiberger, Thomas et al., "Measurement of the Hepatic Venous Pressure Gradient and Transjugular Liver Biopsy" (2020), Jove, J. Vis. Exp., vol. 160, e58819, doi: 103791/58819, 16 pages.

Reiberger, Thomas et al., "The rationale and study design of two phase II trials examining the effects of BI 685,509, a soluble guanylyl cyclase activator, on clinically significant portal hypertension in patients with compensated cirrhosis", (2023) Trials, vol. 24,293, pp. 1-17.

Reiberger, Thomas, et al., Austrian consensus guidelines on the management and treatment of portal hypertension (Billroth III), (2017) Wien Klin Wochenschr, vol. 129, S3, S135-S158.

Reinhart, The novel, clinical stage soluble guanylate cyclase activator BI 685509 protects from disease progression in models of renal injury and disease, Journal od pharmcology and experimental therapeutics, 2022, downloaded from https://doi.org/10.1124/jpet.122.001423.

Rodan, Allyn "Potassium: friend or foe?" (2017) Pediatric Nephology, 32, 1109-1121.

Salazar, Gloria A et al. "KL-6 But Not CCL-18 Is a Predictor of Early Progression in Systemic Sclerosis-related Interstitial Lung Disease" (2018) Journal of Rheumatology, 1153-1158.

Satoh, H et al. "Increased levels of KL-6 and subsequent mortality in patients with interstitial lung diseases" (2006) Journal of Internal Medicine; 260: 429-434.

Schindler, Biochemistry and Pharmacology of Novel Anthralic Acid derivatives activating Heme-oxidized Soluble Guanylyl Clyclase, Molecular Pharma, 2006, 9 pages.

Schindler, Ursula., "Biochemistry and Pharmacology of Novel Anthranilic Acid Derivates Activating Heme-Oxidized Soluble Guanylyl Cyclase" Molecular Pharmacology (2006) vol. 69', No. 4 pp. 1260-1268.

Stasch, Johannes-Peter, et al., "No. and HAEM-Independent Activation of Soluble Guanylyl Cyclase: Molecular Basis and Cardiovascular Implications of a New Pharmacological Principle" British Journal of Pharmacology (2002) vol. 136 pp. 773-783.

Stasch, No. and haem-independent activation of soluble guanylyl cyclase, British Journal of Pharmacology, 2002, vol. 136, 3 pages.

Steen, Virginia et al. "The Value of the Health Assessment Questionnaire and in Systemic Sclerosis Patients Over Time Special Patient-Generated Scales To Demonstrate Change" (1997) Arthritis & Rheumatism, 40(11), 1984-1991.

Sullivan, K.M et al. "Myeloablative Autologous Stem-Cell Transplantation for Severe Scleroderma" (2018) N Engl J Med, 378(1), 35-47.

U.S. Appl. No. 61/697,899, filed Sep. 7, 2012.

US Serial No. 8569339, Issued Oct. 29, 2013, Inventor Jehrod Burnett Brenneman.

US Serial No. 8815857, issued Aug. 26, 2014, Inventor Zhonghua Zhang.

US Serial No. 8906904, Issued Dec. 9, 2014, Inventor Jehrod Burnett Brenneman.

Villanueva, Candid et al., "Development of Hyperdynamic Circulation and Response to ß-Blockers in Compensated Cirrhosis with Portal Hypertenstion" (2016), Hepatology, vol. 63, 197-206.

Wanner, Christoph et al. "Empagliflozin and Progression of Kidney Disease in Type 2 Diabetes" (2016) NEJM, vol. 375, 323-334.

Abstracts, Hepatology, vol. 74, Issue 51, https://aasldpubs.onlinelibrary.wiley.com/doi/full/10/1002/hep.32188, last visited on Jul. 5, 2022.

Abstracts, vol. 74, Issue 51, https://assldpubs.onlinelibrary.wiley.com/doi/full/10.1002/hep.32188, last visited on Jul. 5, 2022, p. 1238A.

Andersen, Karl et al. "The Effects of Aldosterone Synthase Inhibition on Aldosterone and Cortisol in Patients With Hypertension: A Phase II, Randomized, Double-Blind, Placebo-Controlled, Multicenter Study" (2012) The Journal of Clinical Hypertension, vol. 14, No. 9, 580-587.

Ansel, Pharmaceutical Dosage Forms and Drug Delivery Systems, 5th Ed., Lea and Febiger, 1990.

Bairkdar, Majd et al. "Incidence and prevalence of systemic sclerosis globally: a comprehensive systematic review and meta-analysis" (2021) Rheumatology 60: 3121-3133.

Bruce, B et al. "The Health Assessment Questionnaire (HAQ)" (2005) Clin Exp Rheumatol, 23, (Supple 39) s-14-s18.

Chen, Hongxing, et al. "Soluble Guanylate Cyclase Activator BI 685509 Reduces Portal Hypertension and Portosystemic Shunting in a Rat Thioacetamide-Induced Cirrhosis Model" (2022) Hepatology, vol. 76, p. 1190.

Cherney, Pahse Ib study of the SOluble Guanylate Cyclase activator BI 685509 in patients with Diabetic kidney disease, Session information diabetic kidney disease: Clinical Nov. 4, 2021, Abstract, P00479, downloaded at American Society of Nephrology, Kidney Week-Abstract details (2021) (asn-online.org).

Clinical Trials, NCT05559580, A study in people with systemic sclerosis to test whether Avenciguat has an effect on lung function and other systemic Sclerosis symptoms, Oct. 18, 2022.

Clinical Trials: NCT05161481 "A Study to Test whether Two Different Doses of BI 685509 Help People with Liver Cirrhosis and High Blood Pressure in the Portal Vein (Main Vessel Going to the Liver)" Sponsor: Boehringer Ingelheim, Jan. 12, 2022, 8 pages.

Clinical Trials: NCT05161481 "A Study to Test whether Two Different Doses of BI 685509 Help People with Liver Cirrhosis and High Blood Pressure in the Portal Vein (Main Vessel Going to the Liver)" Sponsor: Boehringer Ingelheim, Retrieved from the internet, https://clinicaltrials.gov/ct2/show/NCT05161481, retrieved on 2023-05-31, 5 pgs.

Clinical Trials: NCT05282121 "A Study to Test whether BI 685509 Alone or in Combination with Empagliflozin Helps People with Liver Cirrhosis Caused by Viral Hepatitis or Non-Alcholic Steatohepatitis who have High Blood Pressure in the Portal Vein (Main Vessel Going to the Liver)," Sponsor: Boehringer Ingelheim, Retrieved from the internet, https:// www.clinicaltrials.gov/ct2/show/NCT05282121, 2023-05-31.

D'amico, G et al. "Competing Risks and Prognostic Stages of Cirrhosis: a 25 year inception cohort study of 494 patients", (2014) APT Alimentary Pharmacology and Therapeutics, vol. 39, 1180-1193.

Epstein, Murray "Hyperkalemia constitutes a constraint for implementing renin-angiotensin-aldosterone inhibition: the widening gap

(56) References Cited

OTHER PUBLICATIONS between mandated treatment guidelines and the real-world clinical arena" (2016) Kidney International Supplements, vol. 6, 20-28.
Evgenov, Oleg, V et al., "No. Independent Stimulators and Activators of Soluble Guanylate Cyclase: Discovery and Therapeutic Potential" Nature Reviews / Drug Discovery (2006) vol. 5 pp. 755-768.
Ferreira, Joao Pedro, et al. "Empagliflozin and serum potassium in heart failure: an analysis from EMPEROR-Pooled" (2022) European Heart Journal, vol. 43, 2984-2993.
Ferreira, Joao Pedro, et al. "Interplay of Mineralocorticoid Receptor Antagonists and Empagliflozin in Heart Failure" (2021) Journal of American College of Cardiology, vol. 77, No. 11, 1397-1407.
Gabrielli, Armando et al. "Mechanisms of Disease Scheroderma" (2009) N Engl J Med, 360, 1989-2003.
Garcia-Tsao, Guadalupe et al., "Portal Hypertensive Bleeding in Cirrhosis: Risk Stratification, Diagonis, and Management, 2016 Practice Guidance by the American Association for the Study of Liver Disease" (2017) Hepatology, vol. 65, No. 1, 310-335.
Gladue, Heather et al. "Evaluation of test characteristics for outcome measures used in Raynaud's phenomenon clinical trials" (2013) Arthritis Care Res, 65(4), 630-636.
Graham, Brian L. et al. "Standardization of Spirometry 2019 Update An Official American Thoracic Society and European Respiratory Society Technical Statement" (2019) Am J Respir Crit Care Med, 200(8), e70-e88.
Groszmann, Roberto J. et al. "Beta-Blockers to Prevent Gastroesophageal Varices in Patients with Cirrhosis" (2005), The New England Journal of Medicine, vol. 353, 21, 2254-2261.
Hargovan, Milan et al. "Aldosterone synthase inhibitors in hypertension: current status and future possibilities" (2014) Journal of the Royal Society of Medicine Cardiovascular Disease, 0(0), 1-9.
Herdman, M et al. "Development and preliminary testing of the new five-level version of EQ-5D (EQ-5D-5L)" (2011) Qual Life Res, 20, 1727-1736.
Herrington, William G. et al. "The potential for improving cardio-renal outcomes by sodium-glucose co-transporter-2 inhibition in people with chronic kidney disease: a rationale for the EMPA-KIDNEY study" (2018) Clinical Kidney Journal, 749-761.
Herzog, Erica L. et al. Interstitial Lung Disease Associated With Systemic Sclerosis and Idiopathic Pulmonary Fibrosis How Similar and Distinct? (2014) Arthritis & Rheumatology, vol. 66, No. 8, 1967-1978.
Hinchcliff, Monique et al. "Validity of Two New Patient Reported Outcome Measures in Systemic Sclerosis: the PROMIS-29 Profile and the FACIT-Dyspnea" (2011) Arthiritis Care Res, 63(11) 1620-1628.
Hunter, Robert W. et al. "Hyperkalemia: pathophysiology, risk factors and consequences" (2019) Nephrology Dialysis Transplantation, 34, iii2-iii11.
International Search Report and Written Opinion PCT/US2023/015604 mailed on Mar. 20, 2023.
International Search Report and Written Opinion for PCT/US2012/028205 mailed Jul. 4, 2012.
International Search Report and Written Opinion for PCT/US2015041245, PCT/ISA220, mailed Oct. 7, 2015.
International Search Report and Written Opinion for PCT/US23/036634 mailed Apr. 4, 2024.
International Search Report for PCT/EP2019/068448 mailed Jan. 21, 2021.
International Search Report for PCT/US2012/050052 mailed Oct. 22, 2012.
Issue Fee Payment for U.S. Appl. No. 13/570,432, filed Jun. 6, 2014, (Boehringer Ingelheim Docket No. 09-0574). Inventor: Todd BOSANAC.
Jones, Amanda K. et al., "Soluble Guanylyl Cyclase Activator BI 685509 Reduces Portal Hypertension and Portosystemic Shunting in a Rat Thioacetamide-Induced Cirrhosis Model" (2023), J. of Pharmacology and Experimental Therapeutics, vol. 25, 36 pgs.
Khanna, Dinesh et al. "New composite endpoint in early diffuse cutaneous systemic sclerosis: revisiting the provisional American College of Rheumatology Composite Response Index in Systemic Sclerosis" (2021) Ann Rheum Dis, 80, 641-650.
Khanna, Dinesh et al. "Standardization of the modified Rodnan skin score for use in clinical trials of systemic sclerosis" (2017) 2(1), 11-18.
Khanna, Dinesh et al. "The American College of Rheumatology provisional composite response index for clinical trials in early diffuse cutaneous systemic sclerosis" (2016) Arthritis Rheumatol, 68(2), 299-311.
Kowal-Bielecka, O et al. "EULAR recommendations for the treatment of systemic sclerosis: a report from the EULAR Scleroderma Trials and Research group (EUSTAR)" (2017) Ann Rheum Dis, 76, 1327-1339.
Kuwana, Masataka et al. "Elevated Serum Krebs von den Lungen-6 in Early Disease Predicts Subsequent Deterioration of Pulmonary Function in Patients with Systemic Sclerosis and Interstitial Lung Disease" (2016) 43(10), 1825-1831.
Lancet, "Global, regional, and national age-sex specific all-cause and cause-specific mortality for 240 causes of death, 1990-2013: a systematic analysis for the global burden of Disease study", Europe PMC Founders Group, Lancet, vol. 385, 2015, 117-171.
Lawitz, BI685509 improves hepatic function in subjects with Child-Pugh A cirrhosis and a liver stiffness measureness of >15kPa: results from the HepQuant Shunt test, American Assoc. for the Study of Liver Diseases, The liver Meeting, November 12-15, Anaheim, CA, USA, downloaded from https://hepquant. com/wp-content/uploads/2021/12/AASLD-2021-HepQuant-poster_v3_0_Child-Pugh-A-cirrhosis.pdf.
Leroy, E. Carwile et al. "Scleroderma (Systemic Sclerosis): Classification, Subsets and Pathogenesis" (1988) Journal of Rheumatology, 15:2, 202-205.
Macintyre, N et al. "Standardisation of the single-breath determination of carbon monoxide uptake in the lung" (2005) Eur Respir J, 26, 720-735.
Man, Ada et al. "Development and validation of a patient-reported outcome instrument for skin involvement in patients with systemic sclerosis" (2017) 76, 1374-1380.
Mandorfer, Mattias et al., "Changes in Hepatic Venous Pressure Gradient Predict Hepatic Decompensation in Patients Who Achieved Sustained Virologic Response to Interferon-Free Therapy", (2020) Hepatology, vol. 71, No. 3, 1023-1036.
Mandorfer, Mattias, et al., "Hepatic Venous Pressure Gradient Response in Non-Selective Beta-Blocker Treatment, Is it Worth Measuring" (2019) Current Hepatology Reports, vol. 18, 174-186.
Merkel, Carlo et al., "A Placebo-Controlled Clinical Trial of Nadolol in the Prophylaxis of Growth of Small Esophageal Varices in Cirrhosis" (2004) Gastroenterology, vol. 127, 2004, 476-484.
Merkel, Peter A. et al. "Measuring Disease Activity and Functional Status in Patients With Scleroderma and Raynaud's Phenomenon" (2002) Arthritis & Rheumatism, 46(9), 2410-2420.

* cited by examiner

SOLUBLE GUANYLATE CYCLATE ACTIVATORS FOR TREATING SYSTEMIC SCLEROSIS

FIELD OF THE INVENTION

The invention relates to the use of certain soluble guanylate cyclase activators for treating systemic sclerosis.

BACKGROUND

Systemic sclerosis is a devastating disease of unknown etiology. It is a rare, chronic, heterogenous connective tissue disease with vascular, inflammatory and fibrotic features, and it primarily affects women. The estimated worldwide prevalence of SSc is 17.6 per 100,000, ranging from 6.8 per 100,000 in Asia to 25.9 per 100,000 in North America. (M. Bairkdar et al. "Incidence and prevalence of systemic sclerosis globally: a comprehensive systematic review and meta-analysis," Rheumatology 2021; 60(7):3121-3133.) It is considered an orphan disease, with a prevalence rate of approximately 50 to 300 per million in US, 20 to 50 per million in Asia and 100 to 200 per million in Europe. (See, e.g., J. Barnes et al., "Epidemiology of systemic sclerosis: incidence, prevalence, survival, risk factors, malignancy, and environmental triggers," Curr Opin Rheumatol 2012; 24(2):165-170 and A. Gabrielli et al., N Engl J Med 2009; 360(19): 1989-2003.) Disease progression is variable and unpredictable, with cumulative survival from diagnosis estimated at 74.9% at 5 years and 62.5% at 10 years. (B. Thoreau et al., "Treatment of systemic sclerosis," Presse Med (Paris) 2021: 50(1): 104088.) In systemic sclerosis-associated interstitial lung disease (SSc-ILD), median survival is 5 to 8 years. (E. L. Herzog et al. "Interstitial lung disease associated with systemic sclerosis and idiopathic pulmonary fibrosis: how similar and distinct?," Arthritis and Rheumatology, 2014. p. 1967-1978.)

Systemic sclerosis is characterized by potentially widespread and progressive fibrosis of the skin and vascular abnormalities, early development of Raynaud phenomenon (RP), and potential involvement in the musculoskeletal, gastrointestinal, pulmonary, cardiac, renal, neuromuscular, and genitourinary systems. Clinical characteristics are heterogenous and encompass a wide range of disease severity and manifestations. Raynaud phenomenon is a common first manifestation, followed by joint and muscle pain, fatigue, skin tightening, calcinosis, and DUs. Patients with these symptoms struggle to manage their daily life and can be stigmatized due to their facial appearance and limb deformity. These external features are associated with internal organ involvement, including gastrointestinal dysfunction, renal failure, and lung disease, with interstitial lung disease (ILD) and pulmonary arterial hypertension (PAH) as the most common causes of mortality.

Due to the heterogeneity of clinical manifestations and organ involvement, current disease management comprises individually tailored, organ-based symptomatic therapy. Symptomatic treatment of SSc-related organ complications may include immunosuppressants, dihydropyridine-type calcium antagonists, endothelin receptor antagonists, the soluble guanylate cyclase (sGC) stimulator riociguat, prostacyclin analogues, and PDE-5-inhibitors. (O. Kowal-Bielecka et al, "Update of EULAR recommendations for the treatment of systemic sclerosis," Ann Rheum Dis 2017; 76:1327-1339). Immunosuppressive and antifibrotic therapy has been proposed as a treatment of SSc, with limited controlled data. Nintedanib and tocilizumab have been approved for SSc-ILD. Currently, no disease-modifying therapies address the underlying vasculopathy and the prevention of organ damage resulting from vasculopathy.

BRIEF SUMMARY OF THE INVENTION

The present invention relates to methods for treating patients with systemic sclerosis, comprising administering to the patient a pharmaceutically effective amount of a soluble guanylate cyclase (sGC) activator, or a pharmaceutically acceptable salt thereof.

In another embodiment, the invention relates to methods for treating a patient with diffuse cutaneous systemic sclerosis (dcSSc) and vasculopathy, comprising administering to the patient a therapeutically effective amount of a sGC activator, or a pharmaceutically acceptable salt thereof.

The invention also relates to a SGC activator, or a pharmaceutically acceptable salt thereof, for use in treating a patient with dcSSc and vasculopathy.

In another embodiment, the invention relates to methods for treating a patient with early progressive dcSSc and vasculopathy, comprising administering to the patient a therapeutically effective amount of a sGC activator, or a pharmaceutically acceptable salt thereof.

The invention also relates to a SGC activator, or a pharmaceutically acceptable salt thereof, for use in treating a patient with early progressive dcSSc and vasculopathy.

WO 2014/039434 and WO 2020/011804 describe oral, small-molecule activators of sGC useful in the methods of the invention ("the sGC activators of the invention").

In one embodiment of the invention, the sGC activator used in the methods of the invention is a compound of formula (I)

I

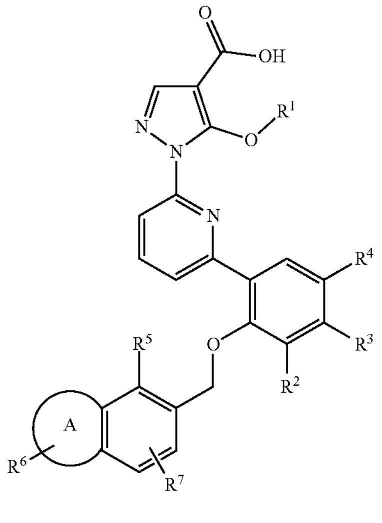

wherein:

A is a 5-7 membered saturated heterocyclyl group containing one nitrogen and optionally one oxygen, wherein one carbon of said heterocyclyl group is optionally substituted with one or two groups selected from $C_{1-3}$alkyl and oxo;

$R^1$ is $C_{1-4}$ alkyl optionally substituted with a methoxy group;

$R^2$ is selected from H, F, Cl, $C_{1-3}$alkyl, —CN, —OMe and —$CF_3$;

$R^3$ is selected from H and —$CH_3$;

$R^4$ is selected from H, F, —$CH_3$ and —OMe;

$R^5$ is selected from H, Cl, —$CH_3$, —$CH_2CH_3$, —$CF_3$, F, and —OMe;

$R^6$ is bonded to the nitrogen on A and is selected from H, $C_{1-6}$alkyl, —$(CH_2)_n C_{3-6}$cycloalkyl, —C(O)$C_{1-6}$alkyl, —$(CH_2)_n$ heterocyclyl, —$(CH_2)_n$ aryl —$(CH_2)_n$ heteroaryl, —$SO_2$aryl, $SO_2C_{1-6}$alkyl wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH, oxo, —$(CH_2)_{1-3}$OH $(CH_2)_{2-3}$OH, and —$SO_2CH_3$;

$R^7$ is selected from H, —$CH_3$, —$CH_2CH_3$, —$CF_3$, F, and —CN;

n is 0, 1 or 2 or a salt thereof.

Unless otherwise stated herein, the terms "the compounds of formula (I)," "the sGC activators of the invention," and "the compounds of the invention" used interchangeably.

In another embodiment, the invention relates to the method described in the embodiment above, wherein:

A is a 5-7 membered saturated heterocyclyl group containing one nitrogen, wherein one carbon of said heterocyclyl group is optionally substituted with one or two $C_{1-3}$alkyl groups;

$R^1$ is $C_{1-3}$alkyl;

$R^2$ is selected from H, F, Cl, $C_{1-3}$alkyl, —CN, —OMe and —$CF_3$;

$R^3$ is selected from H and —$CH_3$;

$R^4$ is selected from H and F;

$R^5$ is selected from H, Cl and —$CH_3$;

$R^6$ is bonded to the nitrogen on A and is selected from H, $C_{1-6}$alkyl, —$(CH_2)_n C_{3-6}$cycloalkyl, —C(O)$C_{1-6}$alkyl, —$(CH_2)_n$ heterocyclyl, —$(CH_2)_n$ aryl and —$(CH_2)_n$ heteroaryl, wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH and —$SO_2CH_3$;

$R^7$ is H;

and n is 0, 1 or 2;

or a salt thereof.

In another embodiment, the invention relates to the methods as described in any of the embodiments above, wherein:

$R^1$ is methyl, ethyl or isopropyl; and the group

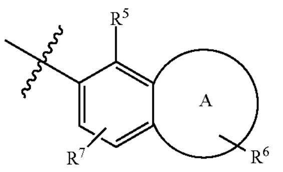

is selected from:

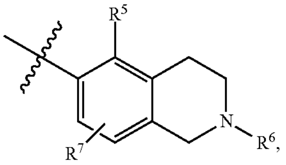

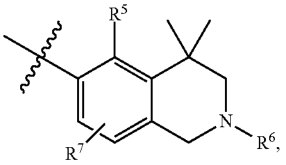

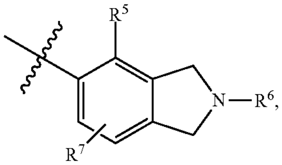

and

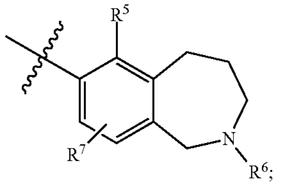

or a salt thereof.

In another embodiment, the invention relates to the methods as described in any of the embodiments above, wherein:

$R^2$ is selected from —$CH_3$, F, Cl, and —$CF_3$; and $R^6$ is selected from H, $C_{1-6}$alkyl, —$(CH_2)_n C_{3-6}$cycloalkyl, —C(O)$C_{1-6}$alkyl and —$(CH_2)_n$ heterocyclyl, wherein said $C_{1-6}$alkyl, —$(CH_2)_n$ cycloalkyl and —$(CH_2)_n$ heterocyclyl are optionally substituted with one to four groups independently selected from $C_{1-3}$alkyl, halogen, $C_{1-3}$alkoxy, —$CF_3$, —OH and —$SO_2CH_3$;

or a salt thereof.

In another embodiment, the invention relates to the methods as described in any of the embodiments above, wherein said heterocyclyl referred to in $R^6$ is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl, 1-oxaspiro[4.5]decanyl and pyrrolidin-2-one;

said heteroaryl referred to in $R^6$ is selected from imidazolyl, isoxazolyl, pyrazinyl, pyrazolyl, pyridinyl, pyrimidinyl, thiazolyl and 4,5,6,7-tetrahydrobenzothiazolyl;

and said aryl referred to in $R^6$ is phenyl;

or a salt thereof.

In another embodiment, the invention relates to the methods as described in any of the embodiments above, wherein:

$R^6$ is —$(CH_2)_n$ heterocyclyl, wherein said heterocyclyl is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl and 1-oxaspiro[4.5]decanyl;

or a salt thereof.

In another embodiment, the invention relates to the methods as described in any of the embodiments above, wherein:

$R^2$ is —$CH_3$;

$R^3$ is H;

$R^4$ is H or —$CH_3$;

$R^5$ is H, or —$CH_3$;

$R^7$ is in the position para to $R^5$ and is H, —$CH_3$ or —$CH_2CH_3$;

or a salt thereof.

In another embodiment, the invention relates to the methods as described in any of the embodiments above, wherein:

the group

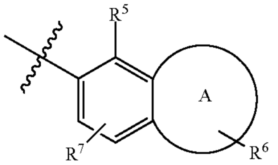

is

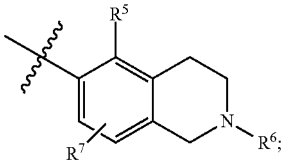

or a salt thereof.

In another embodiment, the invention relates to the methods as described in any of the embodiments above, wherein:

$R^3$ is H; and $R^4$ is H;

or a salt thereof.

Table 1 shows representative compounds of the invention which can be used according to the methods of the invention.

TABLE 1

| Cpd No. | Structure |
|---|---|
| 1 | 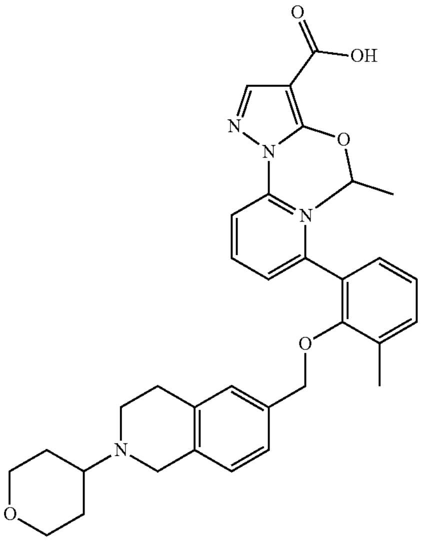 |

TABLE 1-continued

| Cpd No. | Structure |
|---|---|
| 2 | 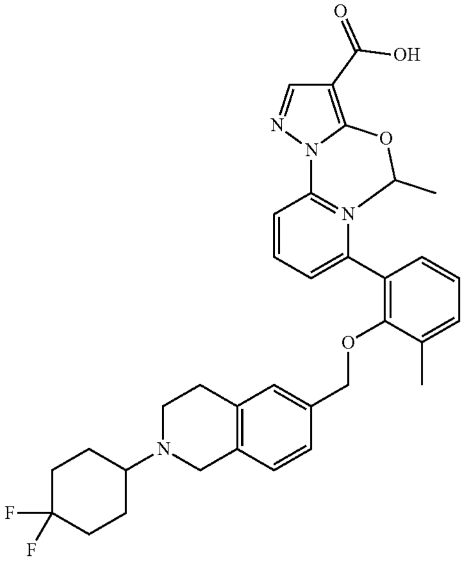 |
| 3 | 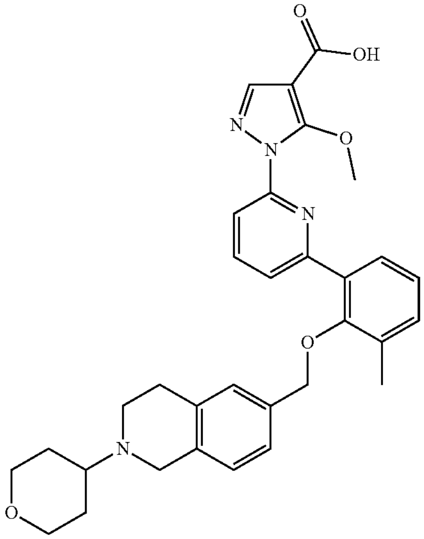 [SMILES: COc1c(C(=O)O)cnn1-c1cccc(-c2cccc(C)c2OCc2ccc3c(c2)CCN(C2CCOCC2)C3)n1] |
| 4 | 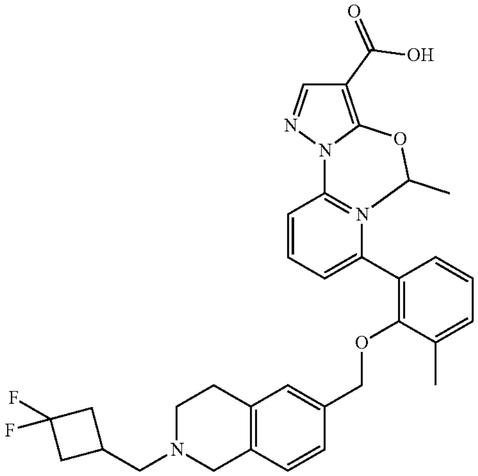 |

TABLE 1-continued
| Cpd No. | Structure |
|---|---|
| 5 | 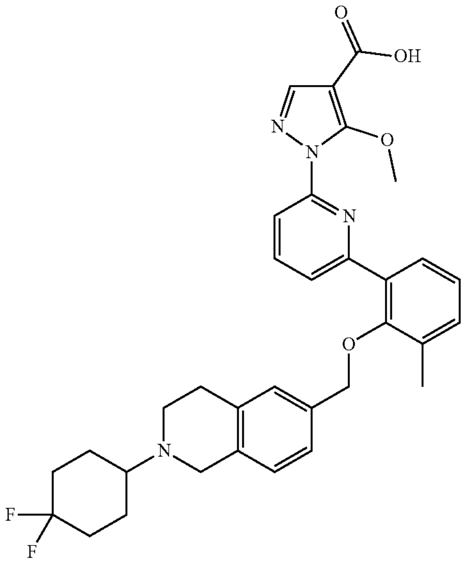 [SMILES: COc1c(C(=O)O)cnn1-c1cccc(-c2cccc(C)c2OCc2ccc3c(c2)CCN(C2CCC(F)(F)CC2)C3)n1] |
| 6 | 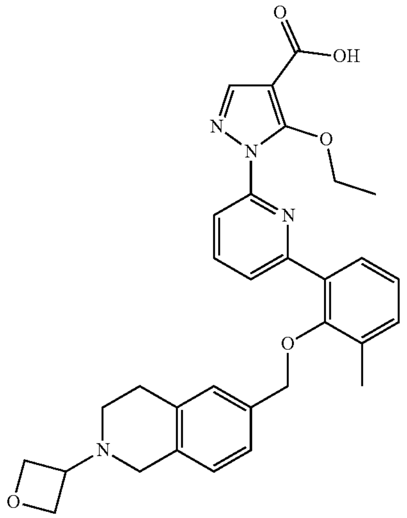 [SMILES: CCOc1c(C(=O)O)cnn1-c1cccc(-c2cccc(C)c2OCc2ccc3c(c2)CCN(C2COC2)C3)n1] |
| 7 | 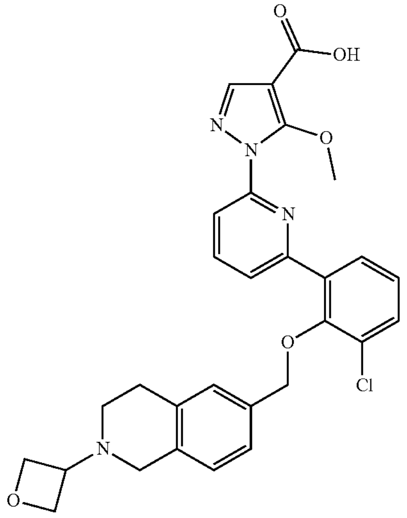 [SMILES: COc1c(C(=O)O)cnn1-c1cccc(-c2cccc(Cl)c2OCc2ccc3c(c2)CCN(C2COC2)C3)n1] |
TABLE 1-continued
| Cpd No. | Structure |
|---|---|
| 8 | 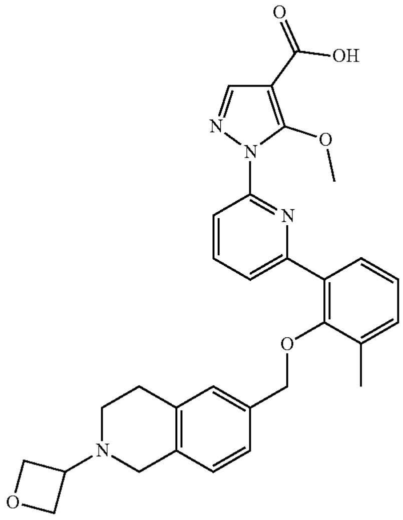 [SMILES: COc1c(C(=O)O)cnn1-c1cccc(-c2cccc(C)c2OCc2ccc3c(c2)CCN(C2COC2)C3)n1] |
| 9 | 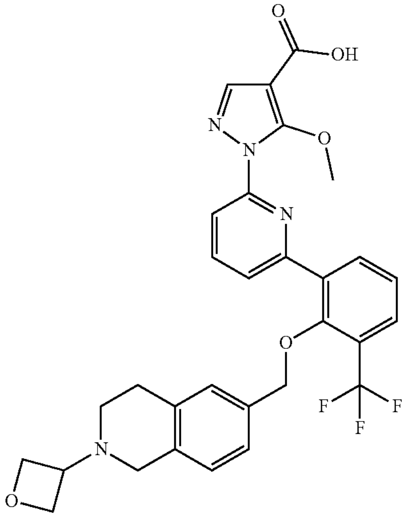 [SMILES: COc1c(C(=O)O)cnn1-c1cccc(-c2cccc(C(F)(F)F)c2OCc2ccc3c(c2)CCN(C2COC2)C3)n1] |
| 10 | 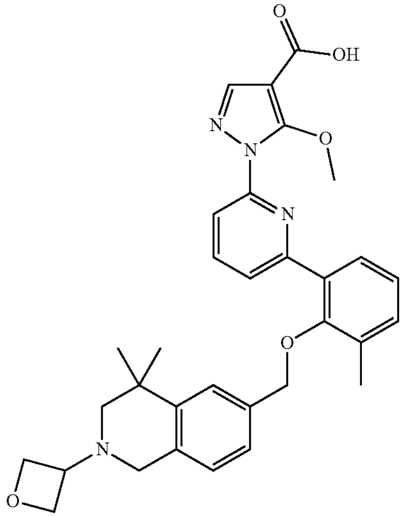 [SMILES: COc1c(C(=O)O)cnn1-c1cccc(-c2cccc(C)c2OCc2ccc3c(c2)C(C)(C)CN(C2COC2)C3)n1] |

TABLE 1-continued
| Cpd No. | Structure |
| --- | --- |
| 11 | 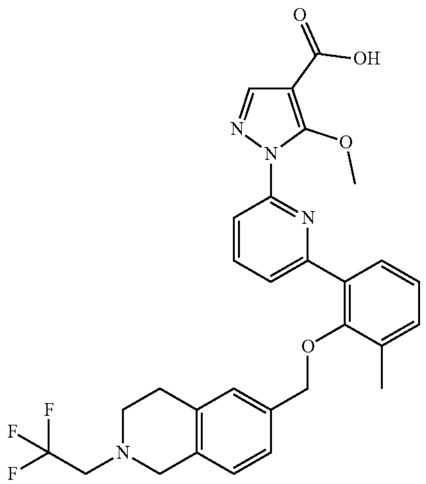 [SMILES: COc1c(C(=O)O)cnn1-c1cccc(-c2cccc(C)c2OCc2ccc3c(c2)CCN(CC(F)(F)F)C3)n1] |
| 12 | 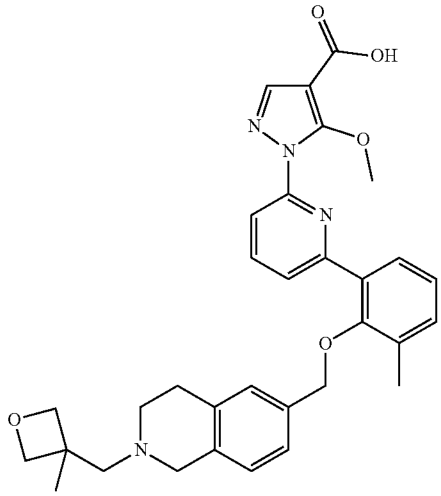 [SMILES: COc1c(C(=O)O)cnn1-c1cccc(-c2cccc(C)c2OCc2ccc3c(c2)CCN(CC2(C)COC2)C3)n1] |
| 13 | 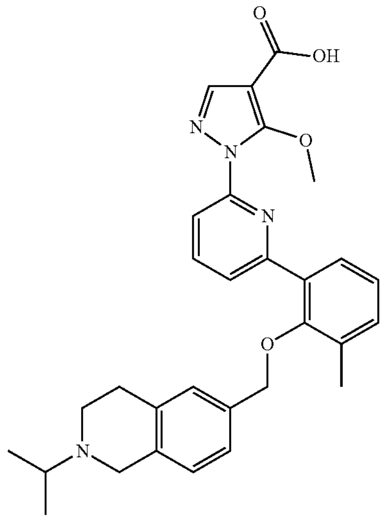 [SMILES: COc1c(C(=O)O)cnn1-c1cccc(-c2cccc(C)c2OCc2ccc3c(c2)CCN(C(C)C)C3)n1] |
TABLE 1-continued
| Cpd No. | Structure |
| --- | --- |
| 14 | 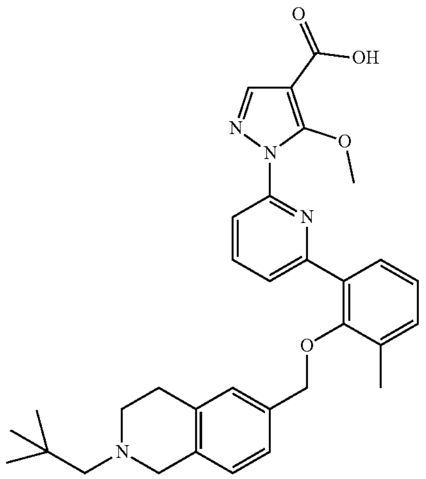 [SMILES: COc1c(C(=O)O)cnn1-c1cccc(-c2cccc(C)c2OCc2ccc3c(c2)CCN(CC(C)(C)C)C3)n1] |
| 15 | 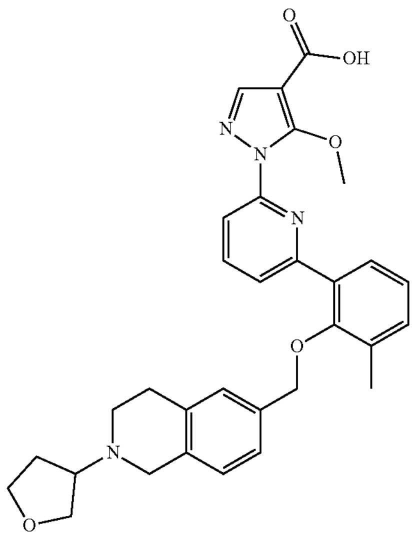 [SMILES: COc1c(C(=O)O)cnn1-c1cccc(-c2cccc(C)c2OCc2ccc3c(c2)CCN(C2CCOC2)C3)n1] |
| 16 | 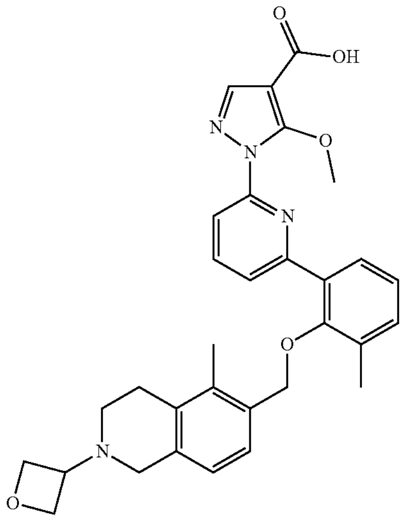 [SMILES: COc1c(C(=O)O)cnn1-c1cccc(-c2cccc(C)c2OCc2ccc3c(c2C)CCN(C2COC2)C3)n1] |

| Cpd No. | Structure |
|---|---|
| 17 | 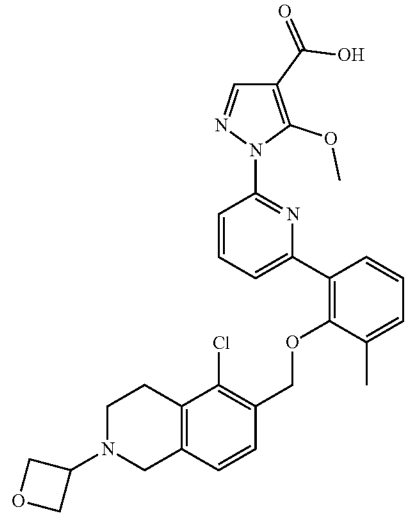 [SMILES: COc1c(C(=O)O)cnn1-c1cccc(-c2cccc(C)c2OCc2ccc3c(c2Cl)CCN(C2COC2)C3)n1] |
| 18 | 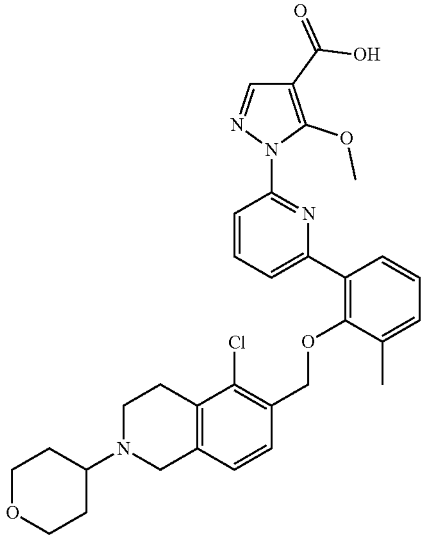 [SMILES: COc1c(C(=O)O)cnn1-c1cccc(-c2cccc(C)c2OCc2ccc3c(c2Cl)CCN(C2CCOCC2)C3)n1] |
| 19 | 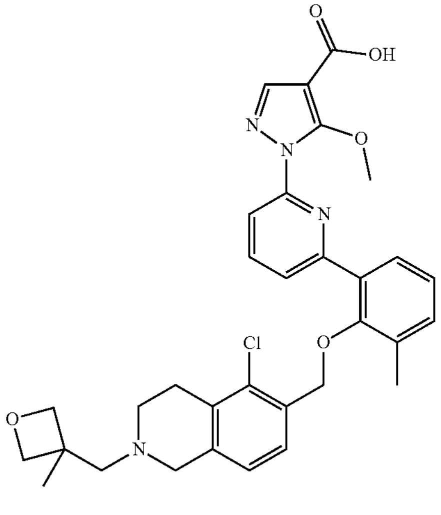 [SMILES: COc1c(C(=O)O)cnn1-c1cccc(-c2cccc(C)c2OCc2ccc3c(c2Cl)CCN(CC2(C)COC2)C3)n1] |
| Cpd No. | Structure |
|---|---|
| 20 | 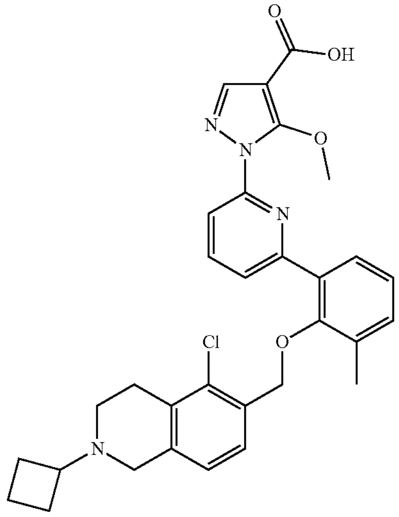 [SMILES: COc1c(C(=O)O)cnn1-c1cccc(-c2cccc(C)c2OCc2ccc3c(c2Cl)CCN(C2CCC2)C3)n1] |
| 21 | 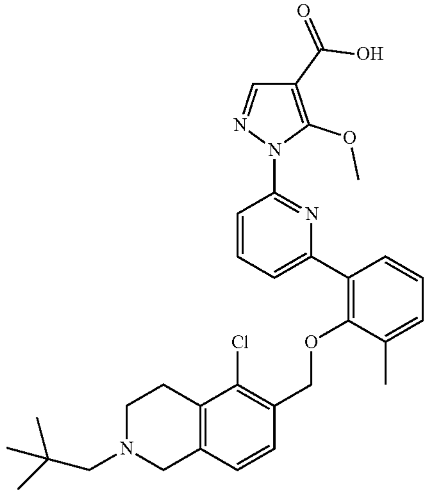 [SMILES: COc1c(C(=O)O)cnn1-c1cccc(-c2cccc(C)c2OCc2ccc3c(c2Cl)CCN(CC(C)(C)C)C3)n1] |
| 22 | 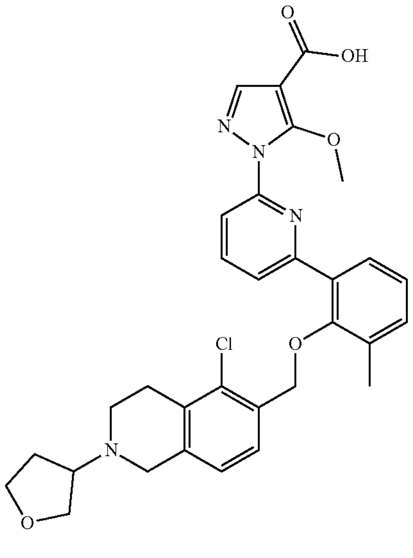 [SMILES: COc1c(C(=O)O)cnn1-c1cccc(-c2cccc(C)c2OCc2ccc3c(c2Cl)CCN(C2CCOC2)C3)n1] |

TABLE 1-continued
| Cpd No. | Structure |
|---|---|
| 23 | 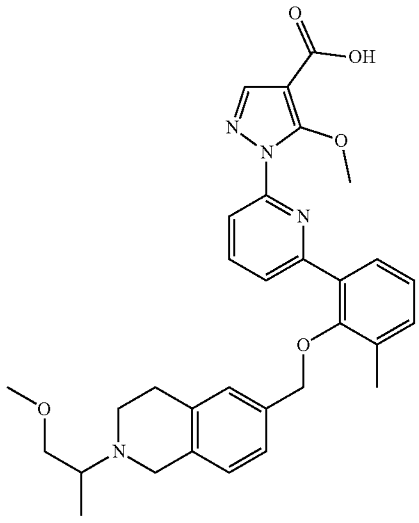 [SMILES: COCC(C)N1CCc2cc(COc3c(C)cccc3-c3cccc(-n4ncc(C(=O)O)c4OC)n3)ccc2C1] |
| 24 | 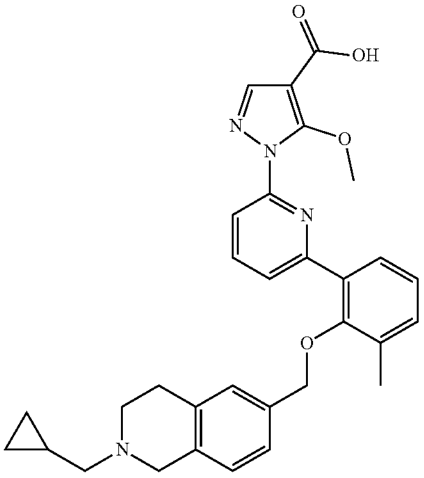 [SMILES: COc1c(C(=O)O)cnn1-c1cccc(-c2cccc(C)c2OCc2ccc3c(c2)CCN(CC2CC2)C3)n1] |
| 25 | 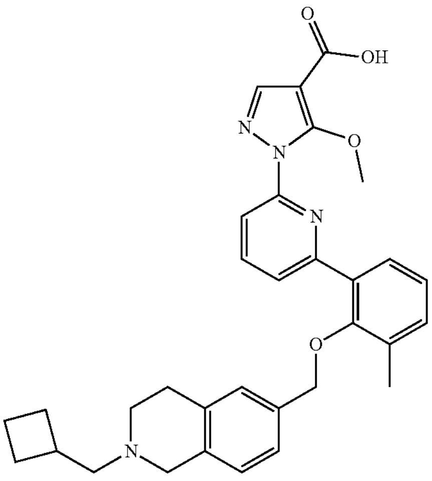 [SMILES: COc1c(C(=O)O)cnn1-c1cccc(-c2cccc(C)c2OCc2ccc3c(c2)CCN(CC2CCC2)C3)n1] |
TABLE 1-continued
| Cpd No. | Structure |
|---|---|
| 26 | 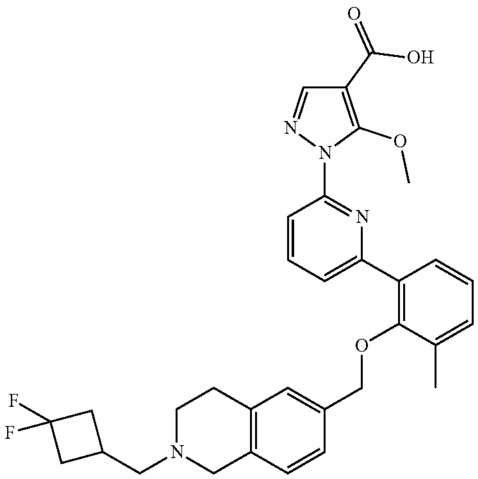 [SMILES: COc1c(C(=O)O)cnn1-c1cccc(-c2cccc(C)c2OCc2ccc3c(c2)CCN(CC2CC(F)(F)C2)C3)n1] |
| 27 | 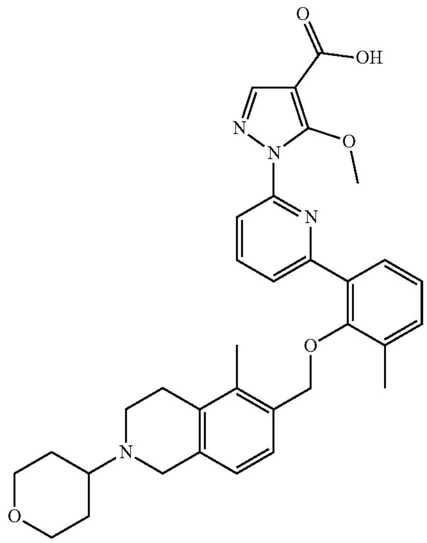 [SMILES: COc1c(C(=O)O)cnn1-c1cccc(-c2cccc(C)c2OCc2ccc3c(c2C)CCN(C2CCOCC2)C3)n1] |
| 28 | 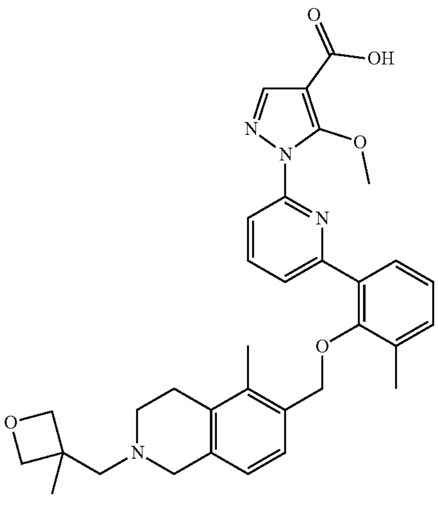 [SMILES: COc1c(C(=O)O)cnn1-c1cccc(-c2cccc(C)c2OCc2ccc3c(c2C)CCN(CC2(C)COC2)C3)n1] |

TABLE 1-continued
| Cpd No. | Structure |
|---|---|
| 29 | 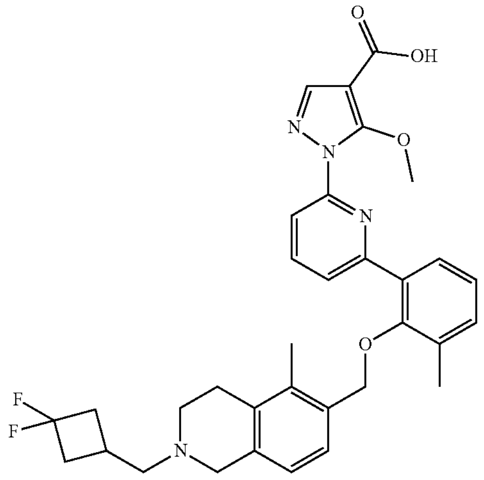 [SMILES: COc1c(C(=O)O)cnn1-c1cccc(-c2cccc(C)c2OCc2ccc3c(c2C)CCN(CC2CC(F)(F)C2)C3)n1] |
| 30 | 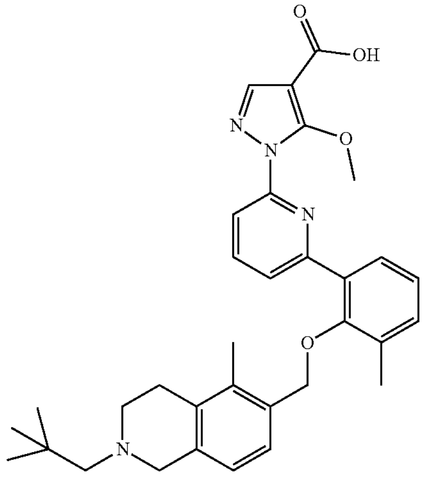 [SMILES: COc1c(C(=O)O)cnn1-c1cccc(-c2cccc(C)c2OCc2ccc3c(c2C)CCN(CC(C)(C)C)C3)n1] |
| 31 | 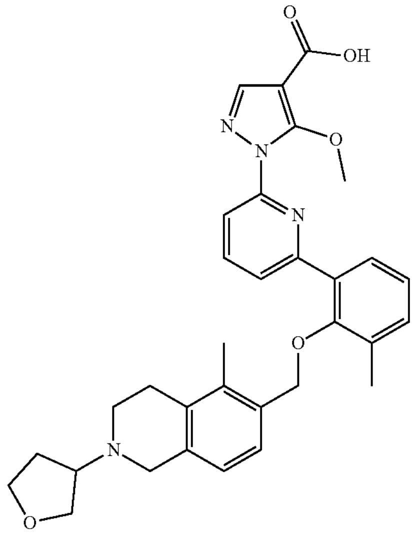 [SMILES: COc1c(C(=O)O)cnn1-c1cccc(-c2cccc(C)c2OCc2ccc3c(c2C)CCN(C2CCOC2)C3)n1] |
TABLE 1-continued
| Cpd No. | Structure |
|---|---|
| 32 | 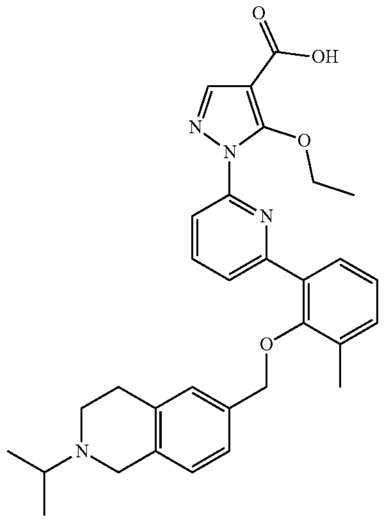 [SMILES: CCOc1c(C(=O)O)cnn1-c1cccc(-c2cccc(C)c2OCc2ccc3c(c2)CCN(C(C)C)C3)n1] |
| 33 | 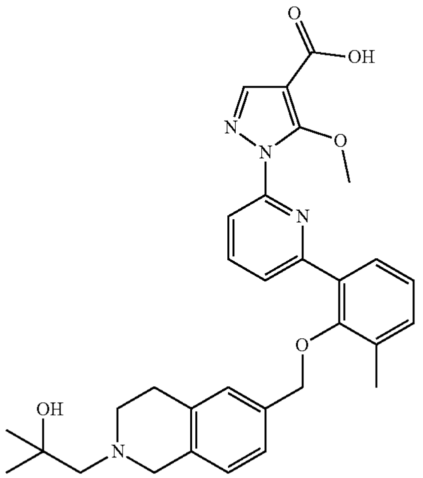 [SMILES: COc1c(C(=O)O)cnn1-c1cccc(-c2cccc(C)c2OCc2ccc3c(c2)CCN(CC(C)(C)O)C3)n1] |
| 34 | 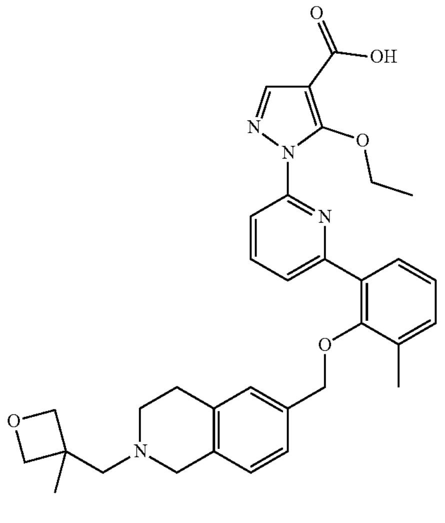 [SMILES: CCOc1c(C(=O)O)cnn1-c1cccc(-c2cccc(C)c2OCc2ccc3c(c2)CCN(CC2(C)COC2)C3)n1] |

TABLE 1-continued
| Cpd No. | Structure |
| --- | --- |
| 35 | 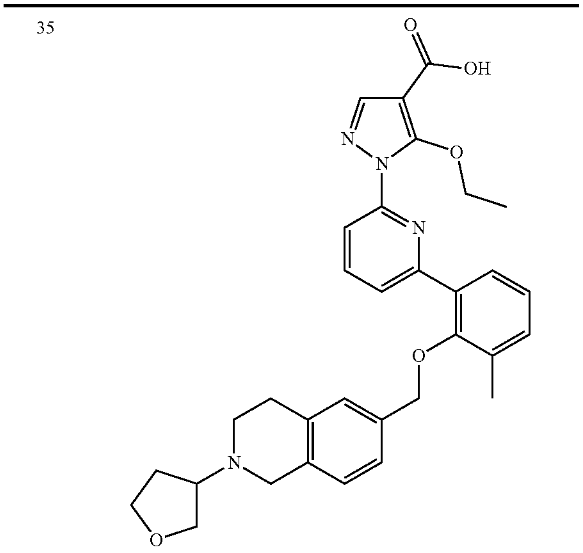 |
| 336 | 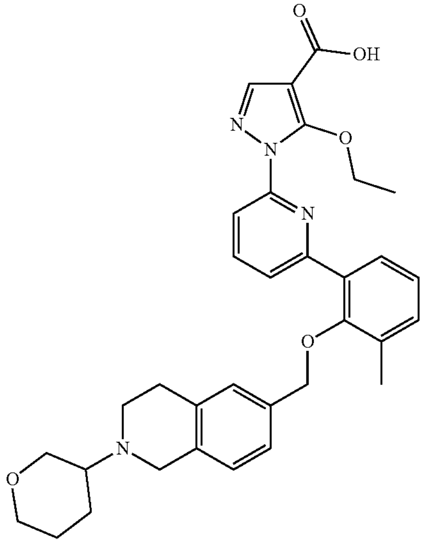 |
| 37 | 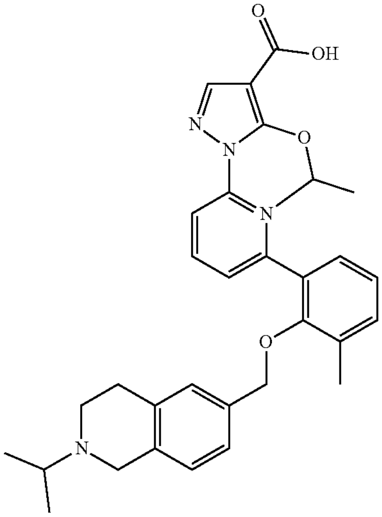 |
| 38 | 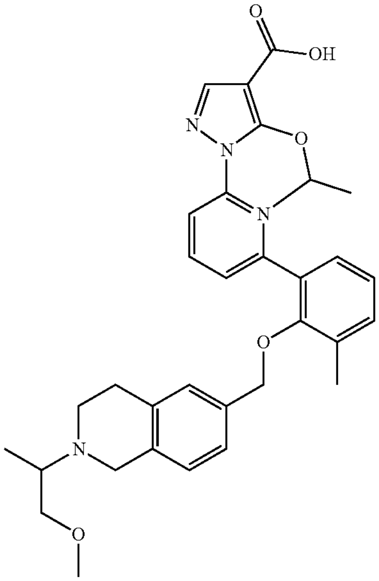 |
| 39 | 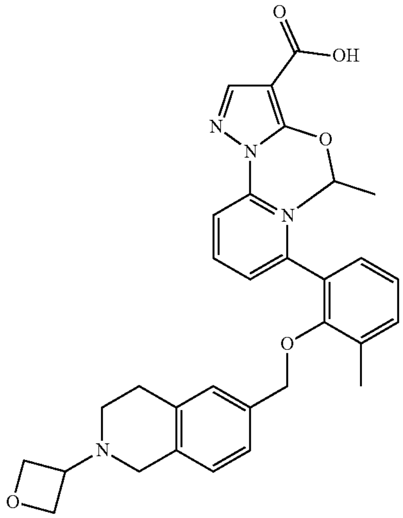 |

TABLE 1-continued
| Cpd No. | Structure |
|---|---|
| 40 | 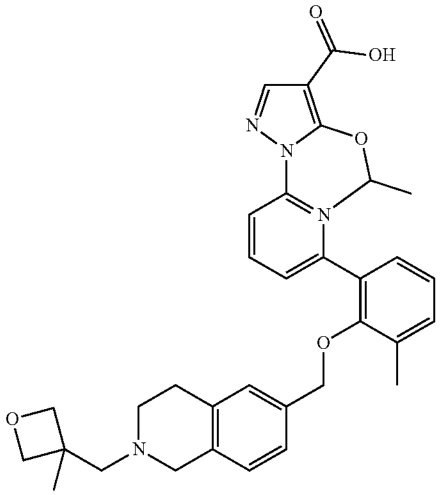 |
| 41 | 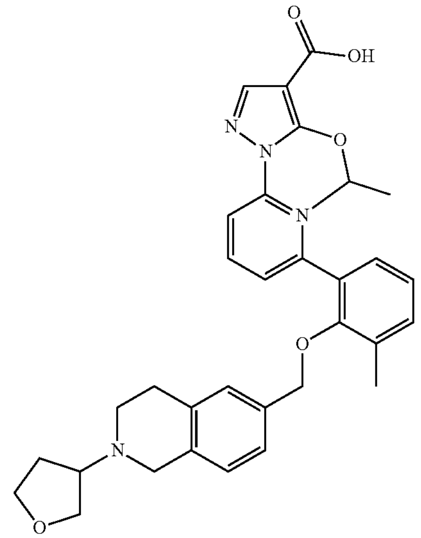 |
| 42 | 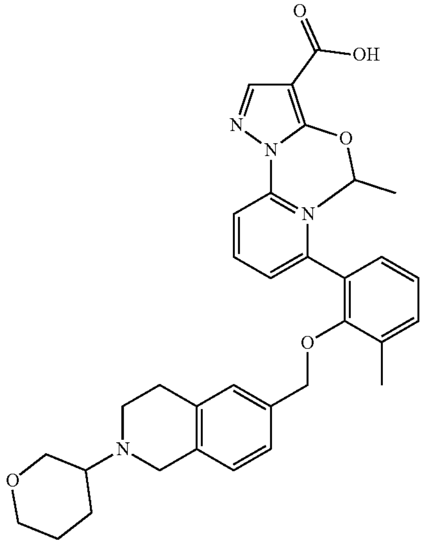 |
TABLE 1-continued
| Cpd No. | Structure |
|---|---|
| 43 | 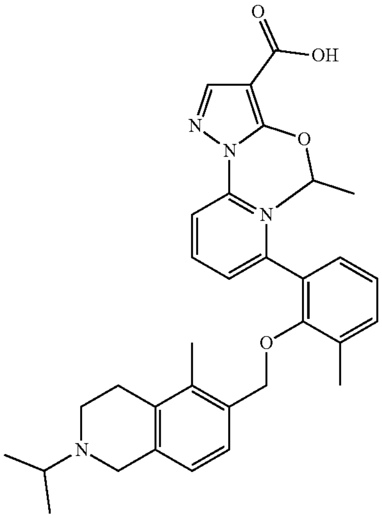 |
| 44 | 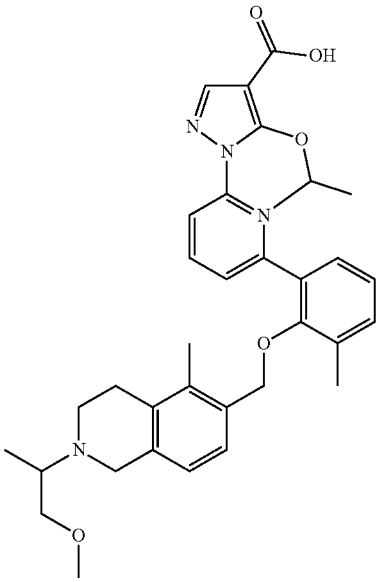 |

TABLE 1-continued
| Cpd No. | Structure |
|---|---|
| 45 | 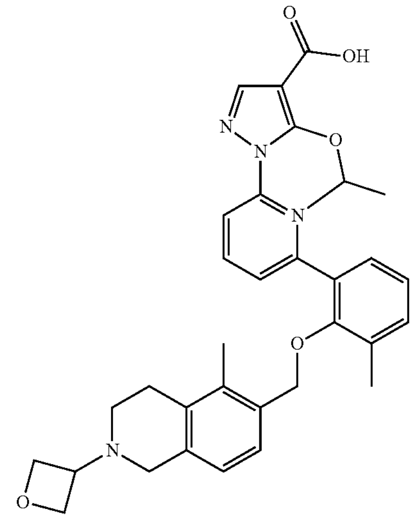 |
| 46 | 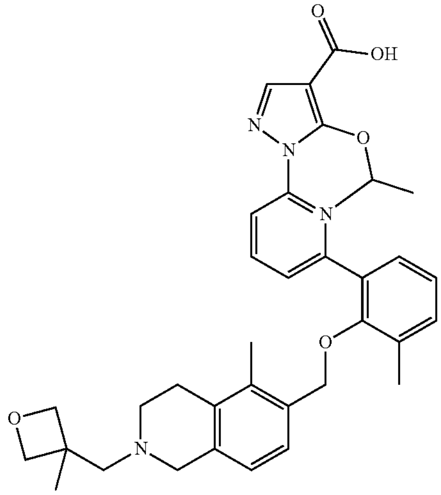 |
| 47 | 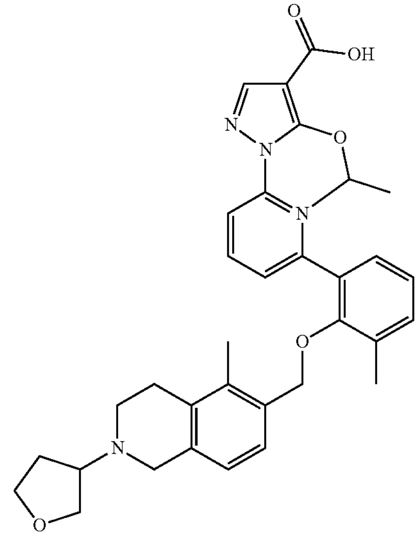 |
| 48 | 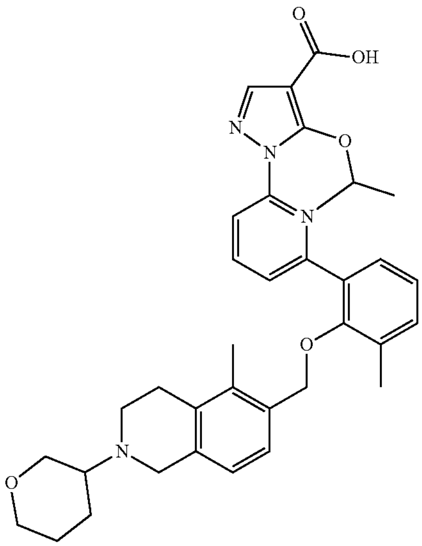 |
| 49 | 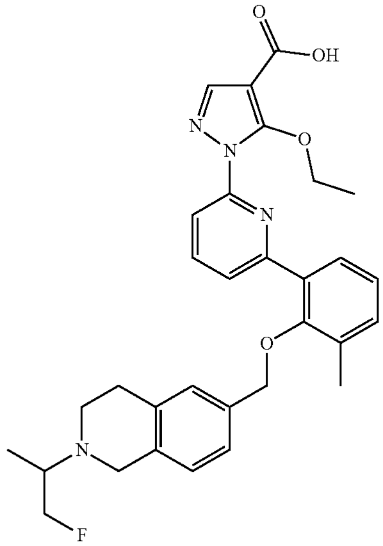 [SMILES: CCOc1c(C(=O)O)cnn1-c1cccc(-c2cccc(C)c2OCc2ccc3c(c2)CCN(C(C)CF)C3)n1] |
| 50 | 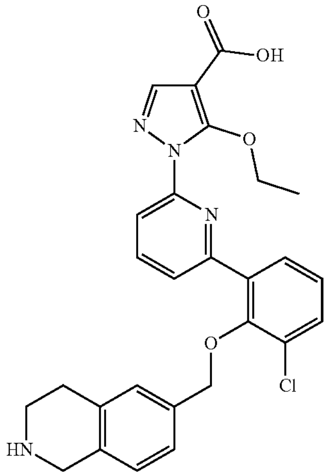 [SMILES: CCOc1c(C(=O)O)cnn1-c1cccc(-c2cccc(Cl)c2OCc2ccc3c(c2)CCNC3)n1] |

TABLE 1-continued
| Cpd No. | Structure |
| --- | --- |
| 51 | 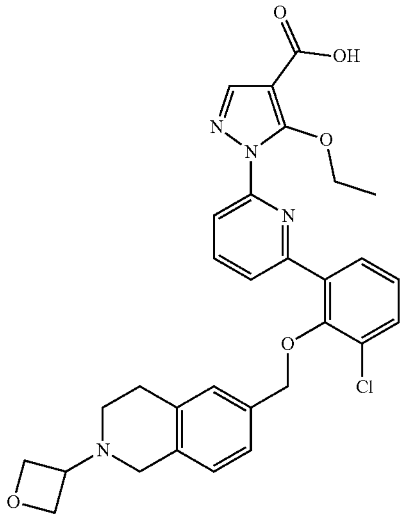 [SMILES: CCOc1c(C(=O)O)cnn1-c1cccc(-c2cccc(Cl)c2OCc2ccc3c(c2)CCN(C2COC2)C3)n1] |
| 52 | 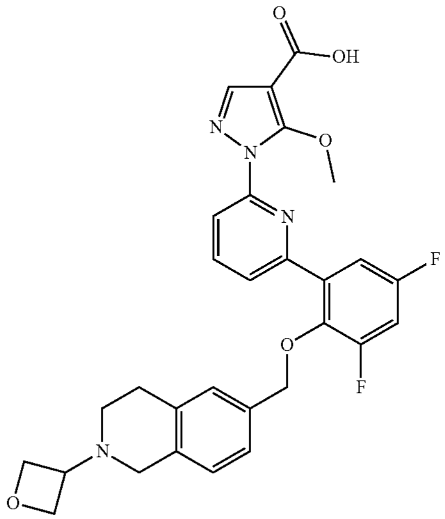 [SMILES: COc1c(C(=O)O)cnn1-c1cccc(-c2cc(F)cc(F)c2OCc2ccc3c(c2)CCN(C2COC2)C3)n1] |
| 53 | 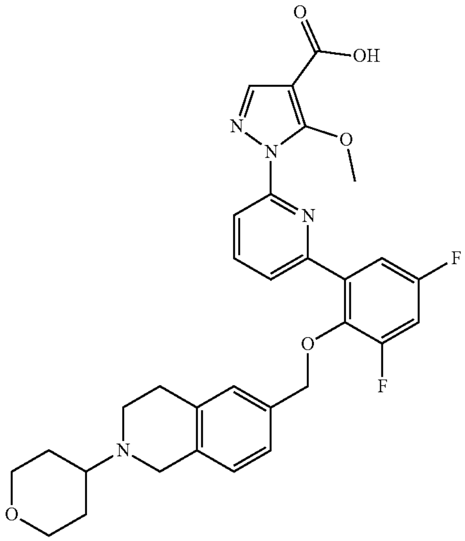 [SMILES: COc1c(C(=O)O)cnn1-c1cccc(-c2cc(F)cc(F)c2OCc2ccc3c(c2)CCN(C2CCOCC2)C3)n1] |
TABLE 1-continued
| Cpd No. | Structure |
| --- | --- |
| 54 | 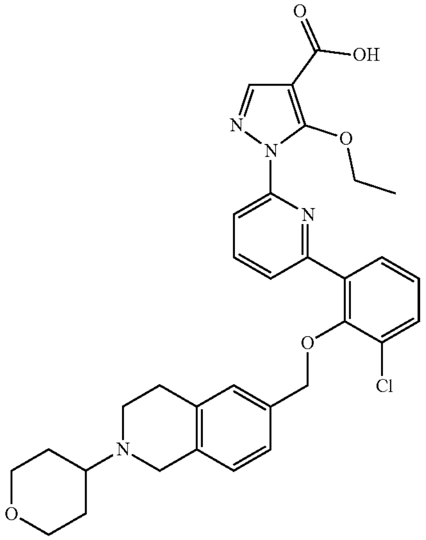 [SMILES: CCOc1c(C(=O)O)cnn1-c1cccc(-c2cccc(Cl)c2OCc2ccc3c(c2)CCN(C2CCOCC2)C3)n1] |
| 55 | 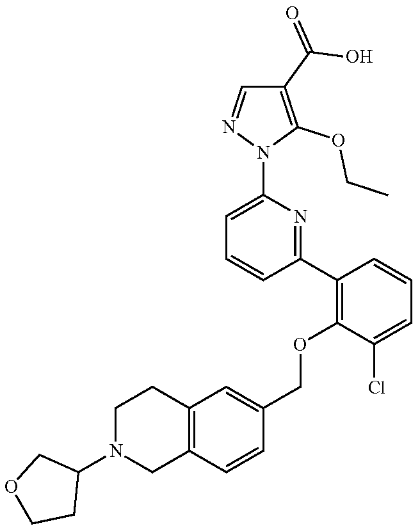 [SMILES: CCOc1c(C(=O)O)cnn1-c1cccc(-c2cccc(Cl)c2OCc2ccc3c(c2)CCN(C2CCOC2)C3)n1] |

TABLE 1-continued
| Cpd No. | Structure |
|---|---|
| 56 | 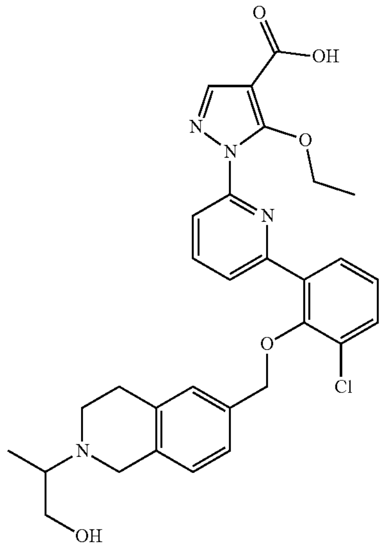 [SMILES: CCOc1c(C(=O)O)cnn1-c1cccc(-c2cccc(Cl)c2OCc2ccc3c(c2)CCN(C(C)CO)C3)n1] |
| 57 | 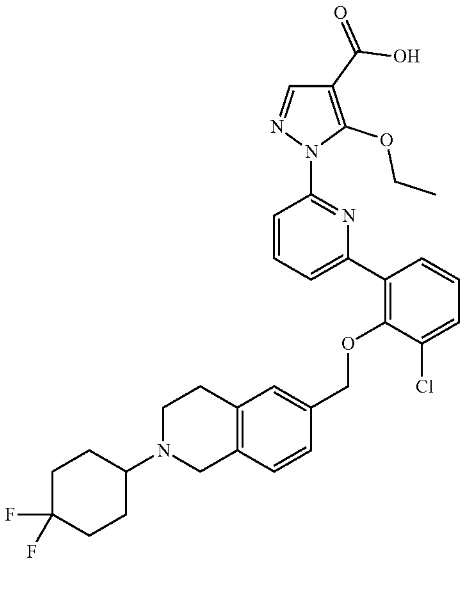 [SMILES: CCOc1c(C(=O)O)cnn1-c1cccc(-c2cccc(Cl)c2OCc2ccc3c(c2)CCN(C2CCC(F)(F)CC2)C3)n1] |
TABLE 1-continued
| Cpd No. | Structure |
|---|---|
| 58 | 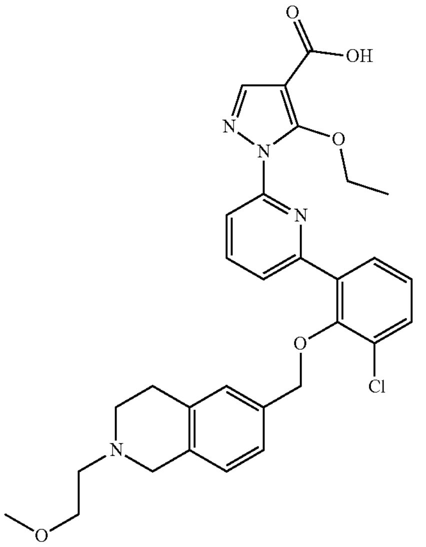 [SMILES: CCOc1c(C(=O)O)cnn1-c1cccc(-c2cccc(Cl)c2OCc2ccc3c(c2)CCN(CCOC)C3)n1] |
| 59 | 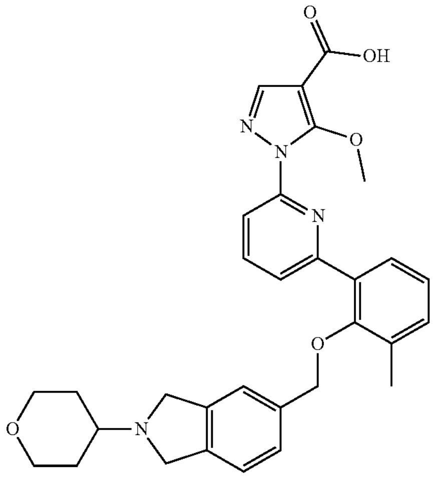 [SMILES: COc1c(C(=O)O)cnn1-c1cccc(-c2cccc(C)c2OCc2ccc3c(c2)CN(C2CCOCC2)C3)n1] |
| 60 | 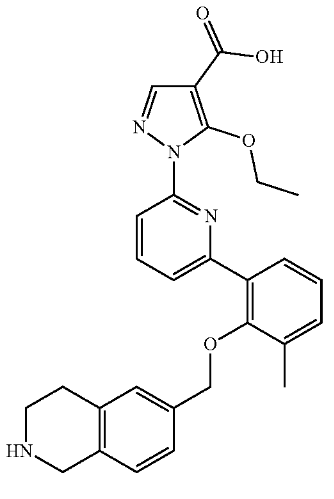 [SMILES: CCOc1c(C(=O)O)cnn1-c1cccc(-c2cccc(C)c2OCc2ccc3c(c2)CCNC3)n1] |

TABLE 1-continued
| Cpd No. | Structure |
|---|---|
| 61 | 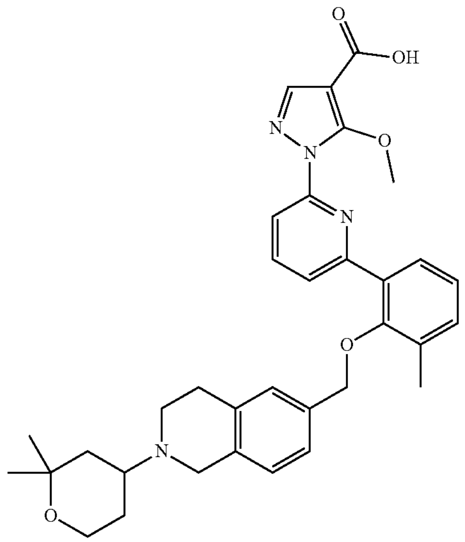 [SMILES: COc1c(C(=O)O)cnn1-c1cccc(-c2cccc(C)c2OCc2ccc3c(c2)CCN(C2CCOC(C)(C)C2)C3)n1] |
| 62 | 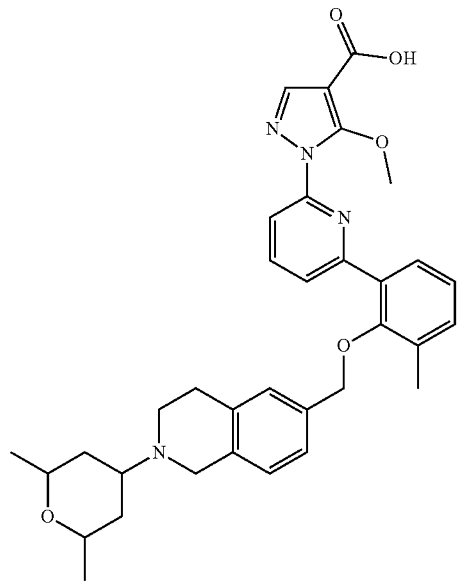 [SMILES: COc1c(C(=O)O)cnn1-c1cccc(-c2cccc(C)c2OCc2ccc3c(c2)CCN(C2CC(C)OC(C)C2)C3)n1] |
TABLE 1-continued
| Cpd No. | Structure |
|---|---|
| 63 | 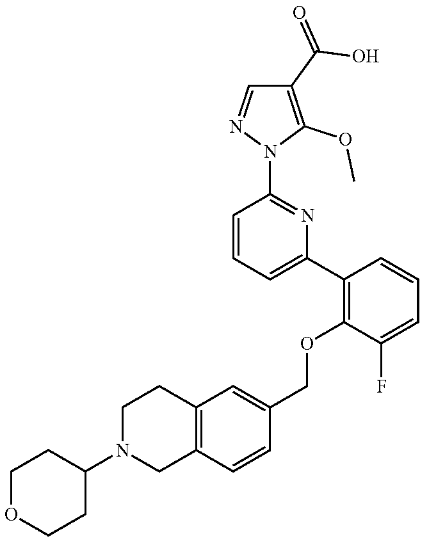 |
| 64 | 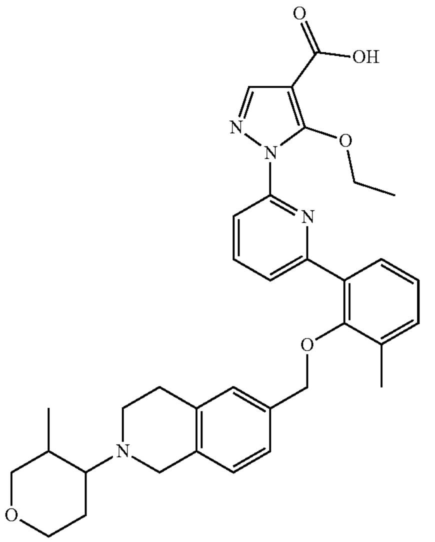 [SMILES: CCOc1c(C(=O)O)cnn1-c1cccc(-c2cccc(C)c2OCc2ccc3c(c2)CCN(C2CCOCC2C)C3)n1] |

TABLE 1-continued
| Cpd No. | Structure |
| --- | --- |
| 65 | 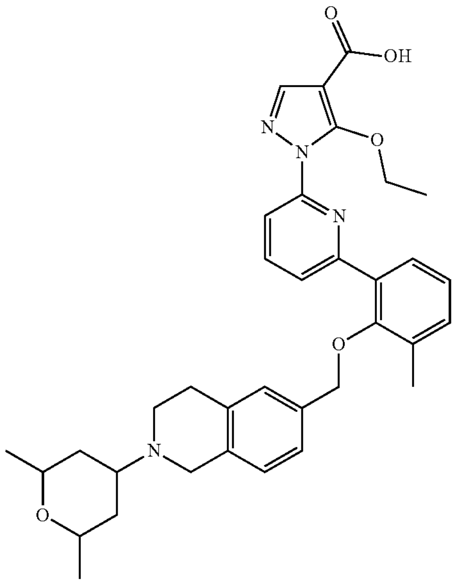 [SMILES: CCOc1c(C(=O)O)cnn1-c1cccc(-c2cccc(C)c2OCc2ccc3c(c2)CCN(C2CC(C)OC(C)C2)C3)n1] |
| 66 | 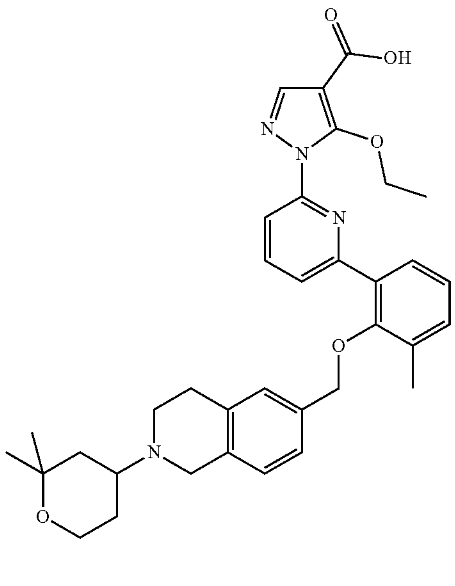 [SMILES: CCOc1c(C(=O)O)cnn1-c1cccc(-c2cccc(C)c2OCc2ccc3c(c2)CCN(C2CCOC(C)(C)C2)C3)n1] |
TABLE 1-continued
| Cpd No. | Structure |
| --- | --- |
| 67 | 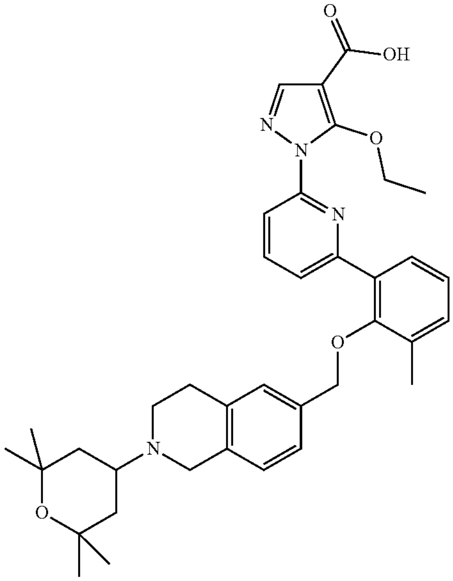 [SMILES: CCOc1c(C(=O)O)cnn1-c1cccc(-c2cccc(C)c2OCc2ccc3c(c2)CCN(C2CC(C)(C)OC(C)(C)C2)C3)n1] |
| 68 | 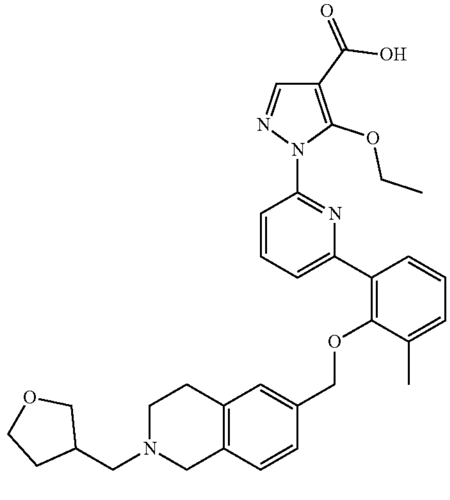 [SMILES: CCOc1c(C(=O)O)cnn1-c1cccc(-c2cccc(C)c2OCc2ccc3c(c2)CCN(CC2CCOC2)C3)n1] |
| 69 | 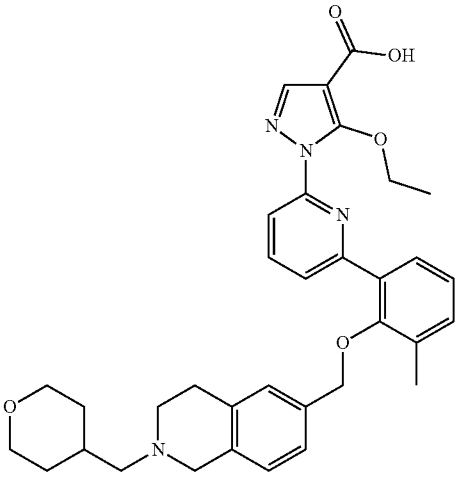 [SMILES: CCOc1c(C(=O)O)cnn1-c1cccc(-c2cccc(C)c2OCc2ccc3c(c2)CCN(CC2CCOCC2)C3)n1] |

TABLE 1-continued
| Cpd No. | Structure |
| --- | --- |
| 70 | 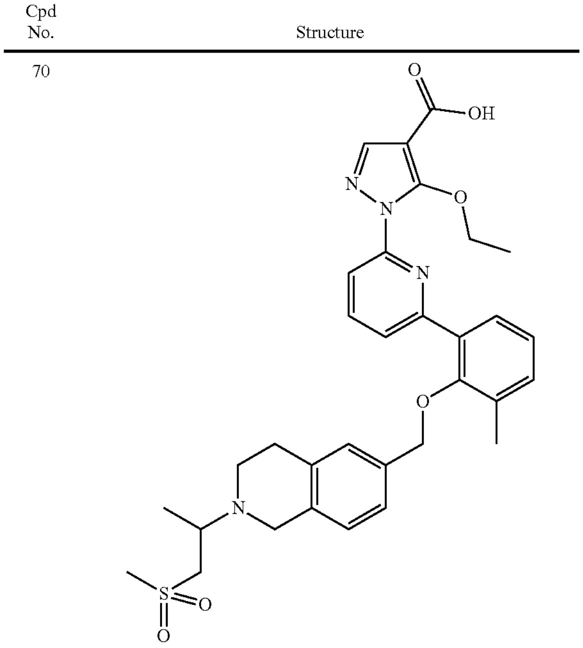 |
| 71 | 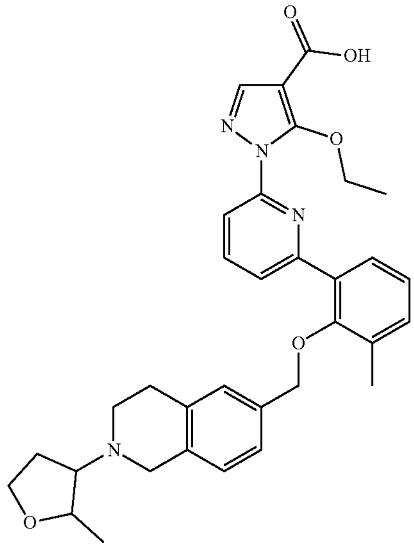 [SMILES: CCOc1c(C(=O)O)cnn1-c1cccc(-c2cccc(C)c2OCc2ccc3c(c2)CCN(C2CCOC2C)C3)n1] |
| 72 | 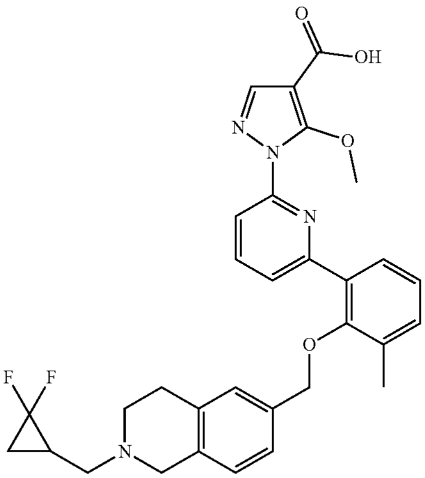 [SMILES: COc1c(C(=O)O)cnn1-c1cccc(-c2cccc(C)c2OCc2ccc3c(c2)CCN(CC2CC2(F)F)C3)n1] |
TABLE 1-continued
| Cpd No. | Structure |
| --- | --- |
| 73 | 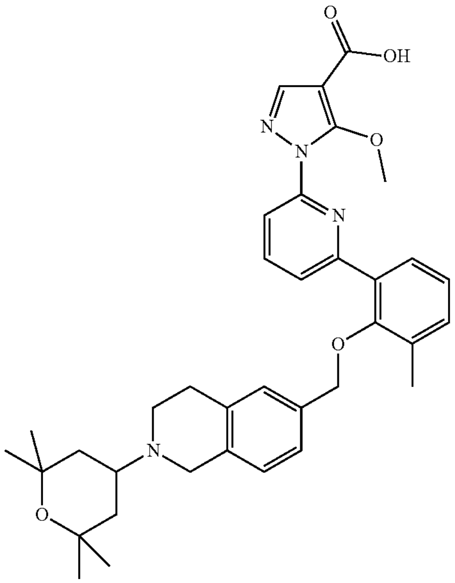 [SMILES: COc1c(C(=O)O)cnn1-c1cccc(-c2cccc(C)c2OCc2ccc3c(c2)CCN(C2CC(C)(C)OC(C)(C)C2)C3)n1] |
| 74 | 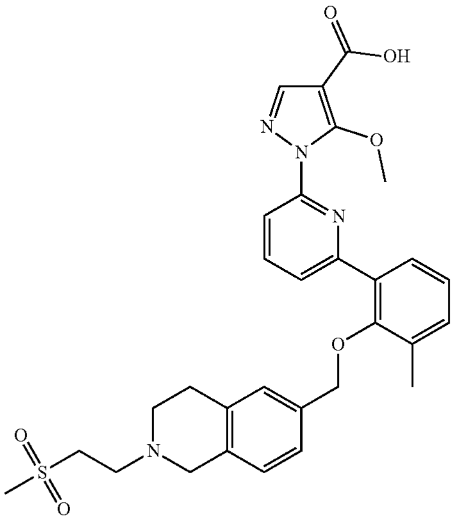 [SMILES: COc1c(C(=O)O)cnn1-c1cccc(-c2cccc(C)c2OCc2ccc3c(c2)CCN(CCS(C)(=O)=O)C3)n1] |

TABLE 1-continued
| Cpd No. | Structure |
|---|---|
| 75 | 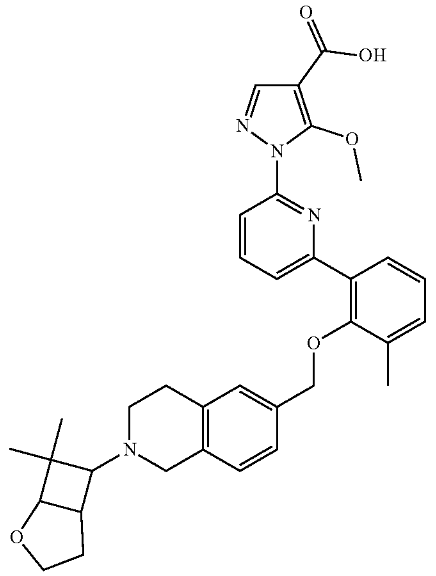 [SMILES: COc1c(C(=O)O)cnn1-c1cccc(-c2cccc(C)c2OCc2ccc3c(c2)CCN(C2C4CCOC4C2(C)C)C3)n1] |
| 76 | 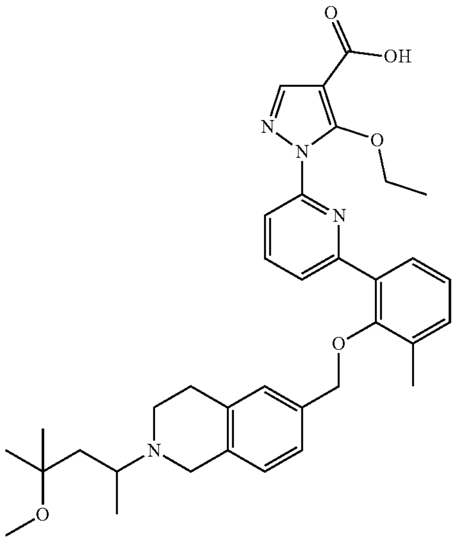 [SMILES: CCOc1c(C(=O)O)cnn1-c1cccc(-c2cccc(C)c2OCc2ccc3c(c2)CCN(C(C)CC(C)(C)OC)C3)n1] |
TABLE 1-continued
| Cpd No. | Structure |
|---|---|
| 77 | 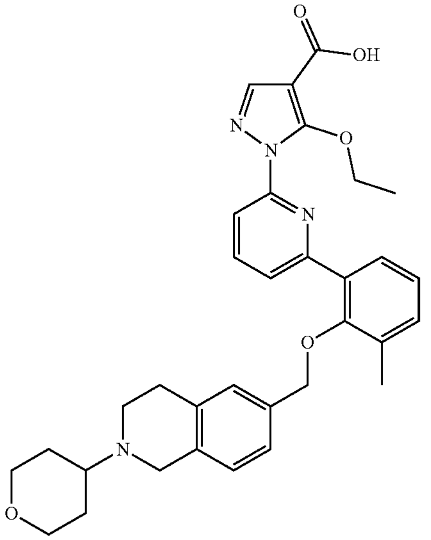 [SMILES: CCOc1c(C(=O)O)cnn1-c1cccc(-c2cccc(C)c2OCc2ccc3c(c2)CCN(C2CCOCC2)C3)n1] |
| 78 | 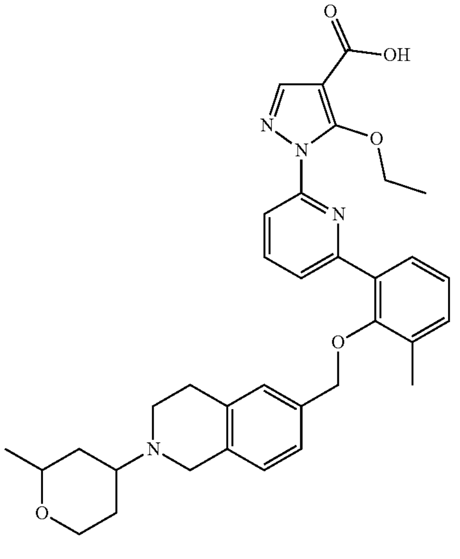 [SMILES: CCOc1c(C(=O)O)cnn1-c1cccc(-c2cccc(C)c2OCc2ccc3c(c2)CCN(C2CCOC(CC)C2)C3)n1] |

TABLE 1-continued
| Cpd No. | Structure |
|---|---|
| 79 | 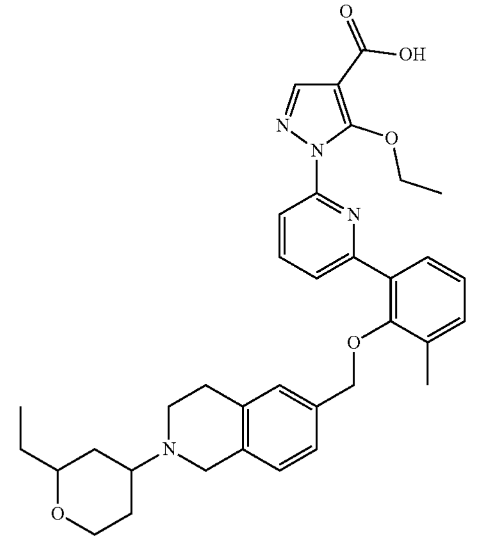 |
| 80 | 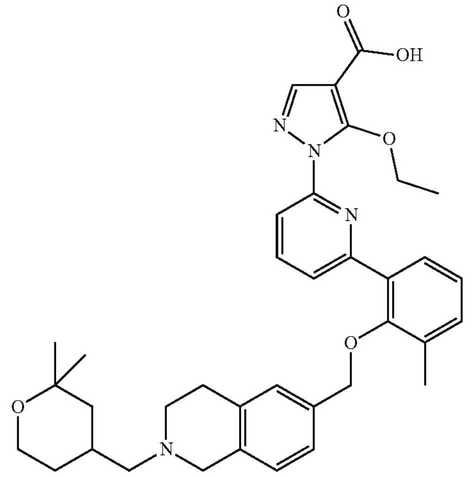 [SMILES: CCOc1c(C(=O)O)cnn1-c1cccc(-c2cccc(C)c2OCc2ccc3c(c2)CCN(CC2CCOC(C)(C)C2)C3)n1] |
| 81 | 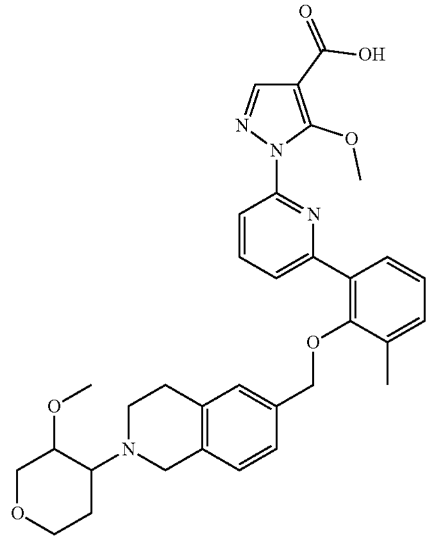 [SMILES: COc1c(C(=O)O)cnn1-c1cccc(-c2cccc(C)c2OCc2ccc3c(c2)CCN(C2CCOCC2OC)C3)n1] |
| 82 | 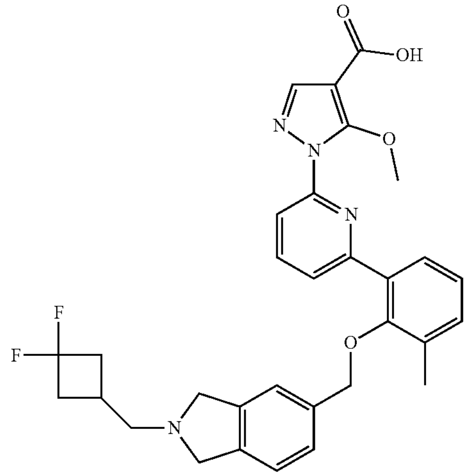 [SMILES: COc1c(C(=O)O)cnn1-c1cccc(-c2cccc(C)c2OCc2ccc3c(c2)CN(CC2CC(F)(F)C2)C3)n1] |
| 83 | 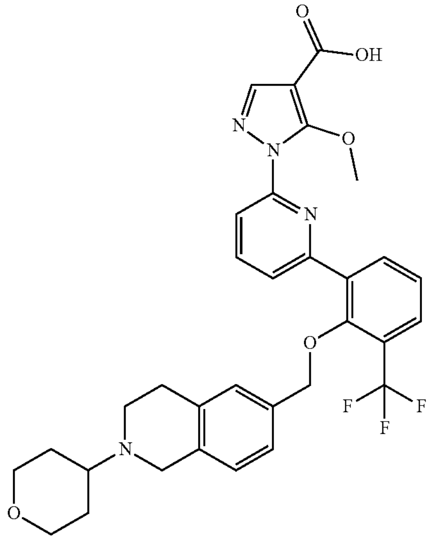 [SMILES: COc1c(C(=O)O)cnn1-c1cccc(-c2cccc(C(F)(F)F)c2OCc2ccc3c(c2)CCN(C2CCOCC2)C3)n1] |
| 84 | 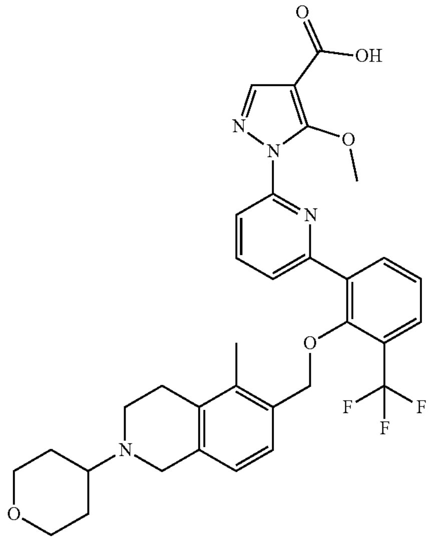 [SMILES: COc1c(C(=O)O)cnn1-c1cccc(-c2cccc(C(F)(F)F)c2OCc2ccc3c(c2C)CCN(C2CCOCC2)C3)n1] |

TABLE 1-continued
| Cpd No. | Structure |
|---|---|
| 85 | 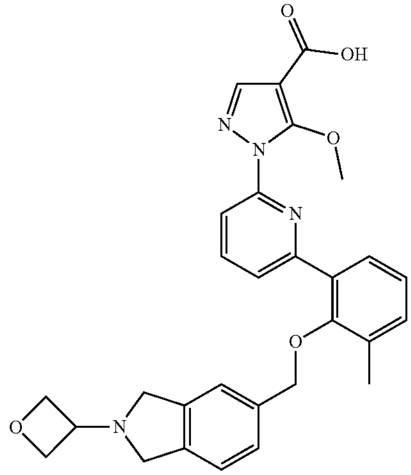 [SMILES: COc1c(C(=O)O)cnn1-c1cccc(-c2cccc(C)c2OCc2ccc3c(c2)CN(C2COC2)C3)n1] |
| 86 | 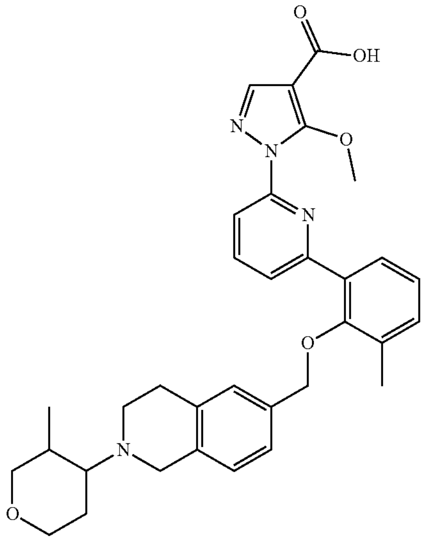 [SMILES: COc1c(C(=O)O)cnn1-c1cccc(-c2cccc(C)c2OCc2ccc3c(c2)CCN(C2CCOCC2C)C3)n1] |
| 87 | 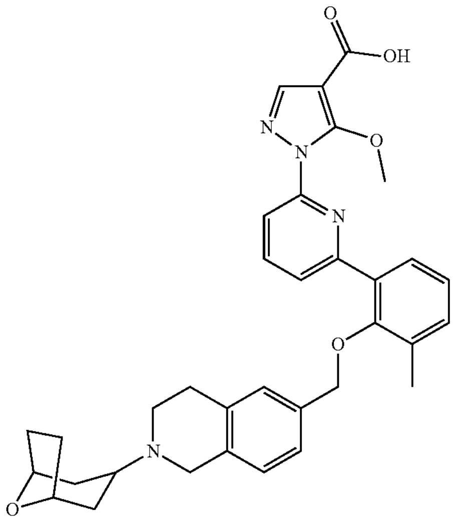 [SMILES: COc1c(C(=O)O)cnn1-c1cccc(-c2cccc(C)c2OCc2ccc3c(c2)CCN(C2CC4CCC(C2)O4)C3)n1] |
| 88 | 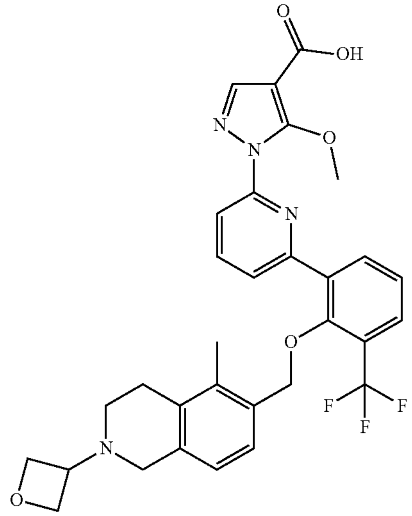 [SMILES: COc1c(C(=O)O)cnn1-c1cccc(-c2cccc(C(F)(F)F)c2OCc2ccc3c(c2C)CCN(C2COC2)C3)n1] |
| 89 | 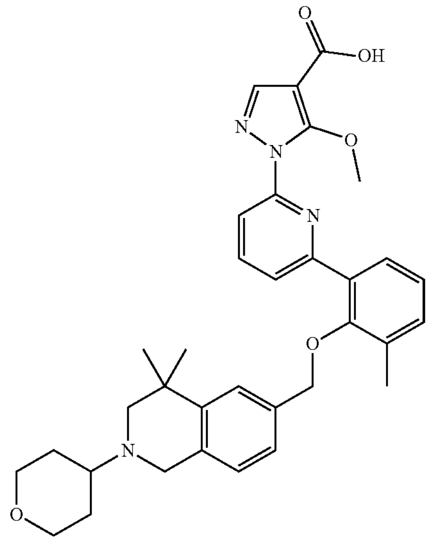 [SMILES: COc1c(C(=O)O)cnn1-c1cccc(-c2cccc(C)c2OCc2ccc3c(c2)C(C)(C)CN(C2CCOCC2)C3)n1] |
| 90 | 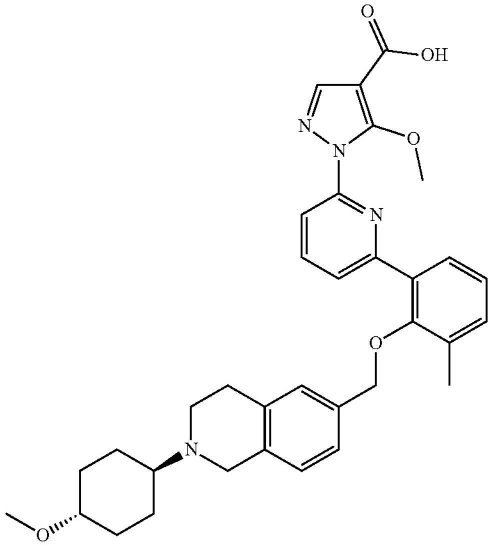 [SMILES: COc1c(C(=O)O)cnn1-c1cccc(-c2cccc(C)c2OCc2ccc3c(c2)CCN([C@H]2CC[C@H](OC)CC2)C3)n1] |

TABLE 1-continued
| Cpd No. | Structure |
|---|---|
| 91 | 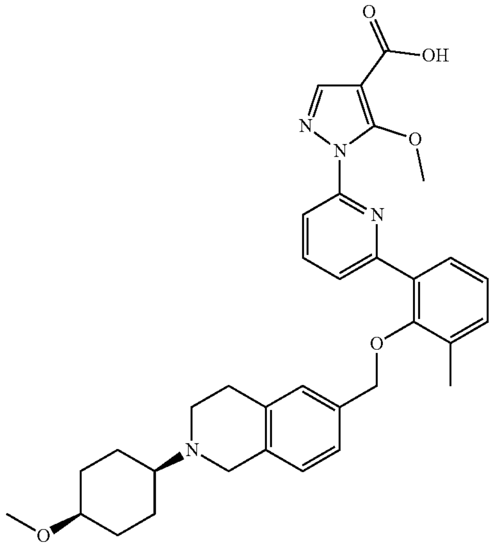 [SMILES: COc1c(C(=O)O)cnn1-c1cccc(-c2cccc(C)c2OCc2ccc3c(c2)CCN([C@H]2CC[C@@H](OC)CC2)C3)n1] |
| 92 | 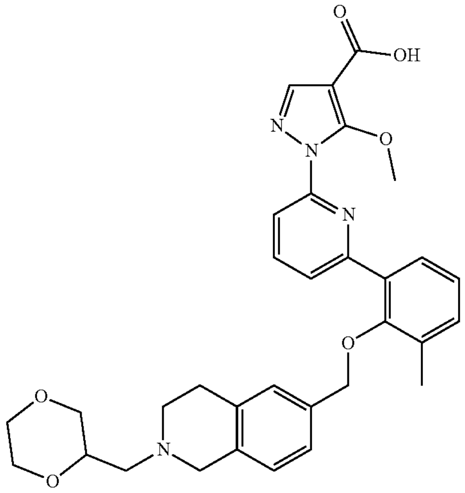 [SMILES: COc1c(C(=O)O)cnn1-c1cccc(-c2cccc(C)c2OCc2ccc3c(c2)CCN(CC2COCCO2)C3)n1] |
| 93 | 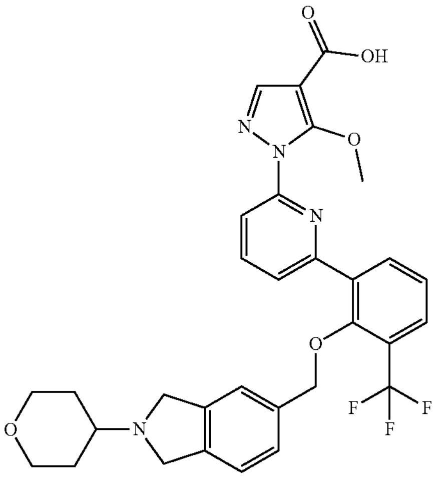 [SMILES: COc1c(C(=O)O)cnn1-c1cccc(-c2cccc(C(F)(F)F)c2OCc2ccc3c(c2)CN(C2CCOCC2)C3)n1] |
TABLE 1-continued
| Cpd No. | Structure |
|---|---|
| 94 | 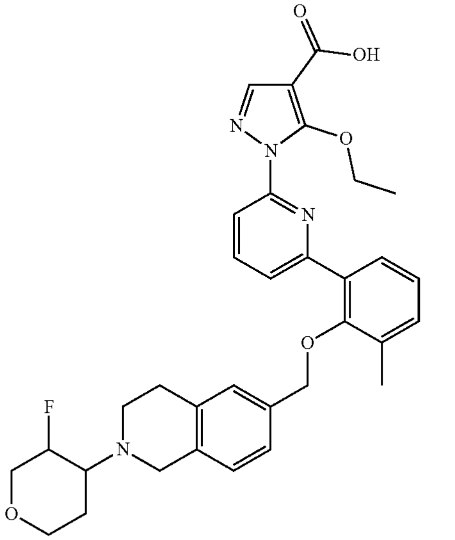 [SMILES: CCOc1c(C(=O)O)cnn1-c1cccc(-c2cccc(C)c2OCc2ccc3c(c2)CCN(C2CCOCC2F)C3)n1] |
| 95 | 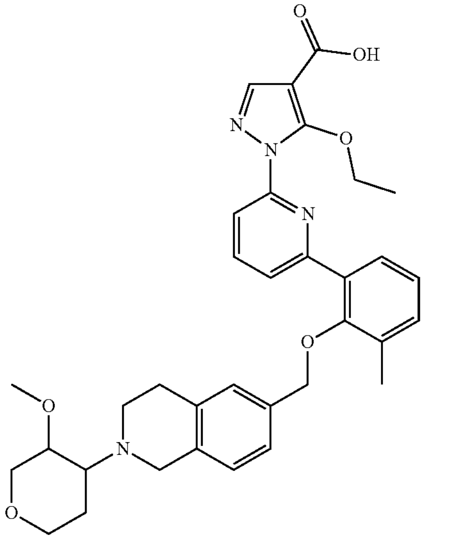 [SMILES: CCOc1c(C(=O)O)cnn1-c1cccc(-c2cccc(C)c2OCc2ccc3c(c2)CCN(C2CCOCC2OC)C3)n1] |
| 96 | 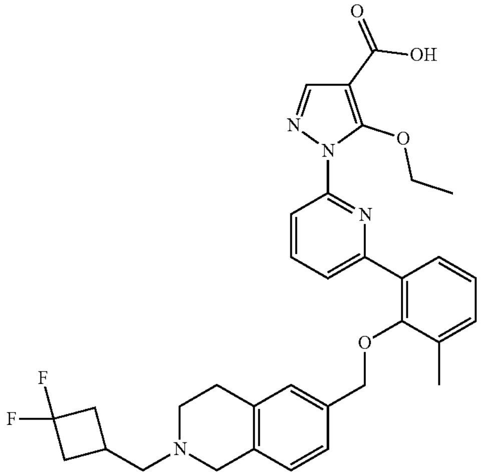 [SMILES: CCOc1c(C(=O)O)cnn1-c1cccc(-c2cccc(C)c2OCc2ccc3c(c2)CCN(CC2CC(F)(F)C2)C3)n1] |

TABLE 1-continued
| Cpd No. | Structure |
| --- | --- |
| 97 | 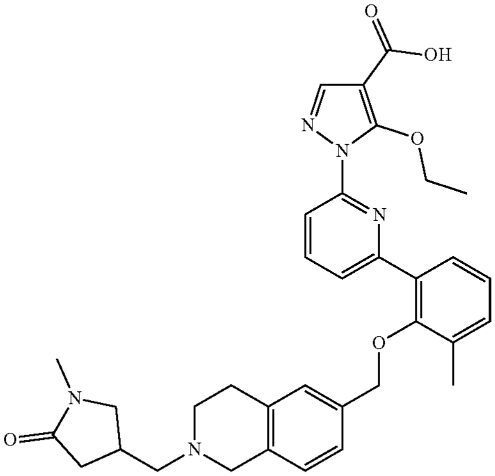 [SMILES: CCOc1c(C(=O)O)cnn1-c1cccc(-c2cccc(C)c2OCc2ccc3c(c2)CCN(CC2CC(=O)N(C)C2)C3)n1] |
| 98 | 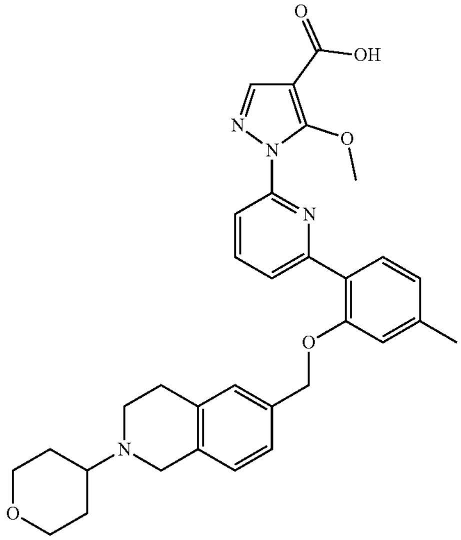 [SMILES: COc1c(C(=O)O)cnn1-c1cccc(-c2ccc(C)cc2OCc2ccc3c(c2)CCN(C2CCOCC2)C3)n1] |
| 99 | 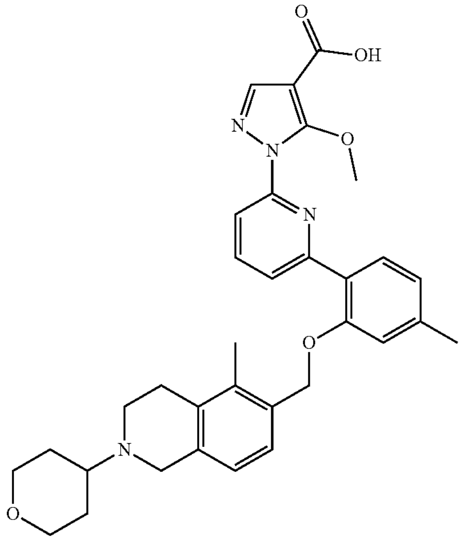 [SMILES: COc1c(C(=O)O)cnn1-c1cccc(-c2ccc(C)cc2OCc2ccc3c(c2C)CCN(C2CCOCC2)C3)n1] |
TABLE 1-continued
| Cpd No. | Structure |
| --- | --- |
| 100 | 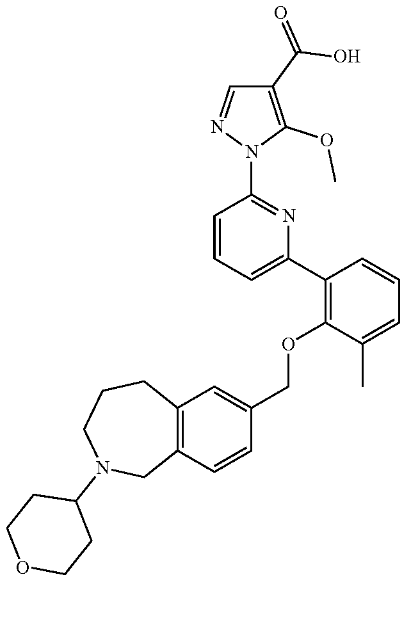 [SMILES: COc1c(C(=O)O)cnn1-c1cccc(-c2cccc(C)c2OCc2ccc3c(c2)CCCN(C2CCOCC2)C3)n1] |
| 101 | 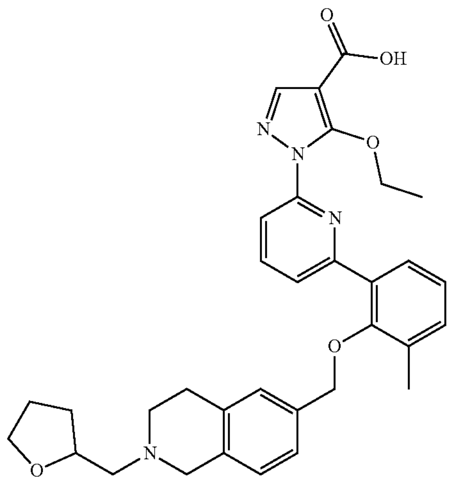 [SMILES: CCOc1c(C(=O)O)cnn1-c1cccc(-c2cccc(C)c2OCc2ccc3c(c2)CCN(CC2CCCO2)C3)n1] |

TABLE 1-continued
| Cpd No. | Structure |
| --- | --- |
| 102 | 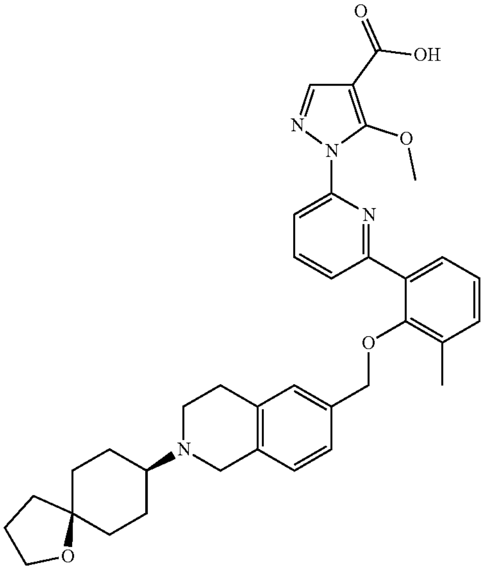 [SMILES: COc1c(C(=O)O)cnn1-c1cccc(-c2cccc(C)c2OCc2ccc3c(c2)CCN([C@H]2CC[C@]4(CCCO4)CC2)C3)n1] |
| 103 | 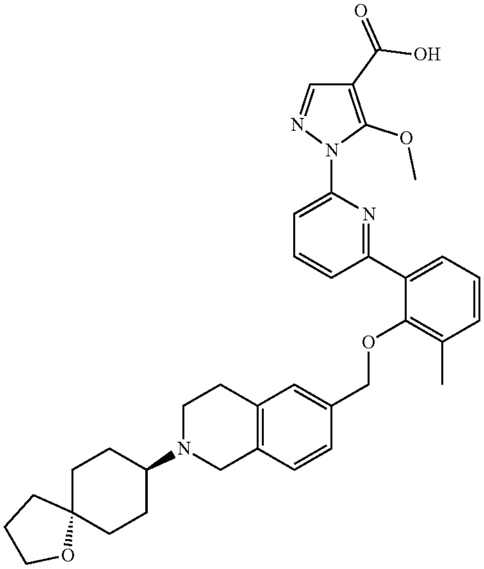 [SMILES: COc1c(C(=O)O)cnn1-c1cccc(-c2cccc(C)c2OCc2ccc3c(c2)CCN([C@H]2CC[C@@]4(CCCO4)CC2)C3)n1] |
TABLE 1-continued
| Cpd No. | Structure |
| --- | --- |
| 104 | 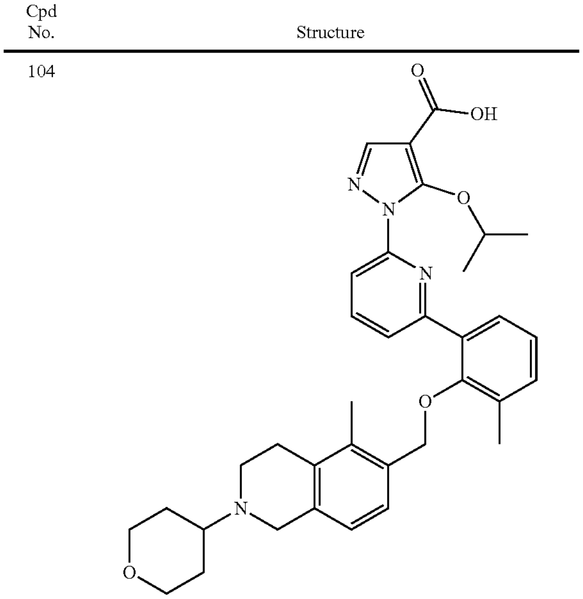 |
| 105 | 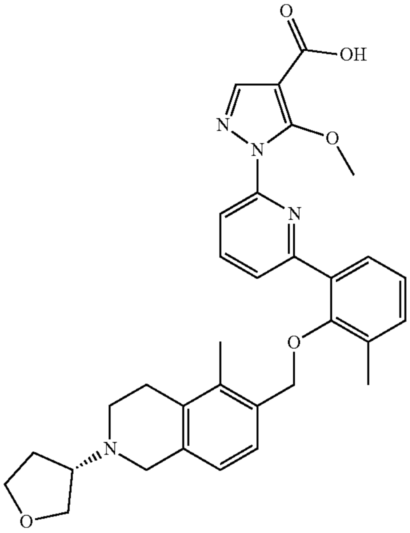 [SMILES: COc1c(C(=O)O)cnn1-c1cccc(-c2cccc(C)c2OCc2ccc3c(c2C)CCN([C@H]2CCOC2)C3)n1] |
| 106 | 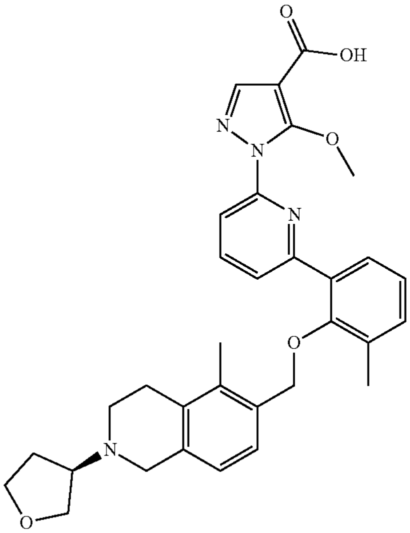 [SMILES: COc1c(C(=O)O)cnn1-c1cccc(-c2cccc(C)c2OCc2ccc3c(c2C)CCN([C@@H]2CCOC2)C3)n1] |

TABLE 1-continued
| Cpd No. | Structure |
|---|---|
| 107 | 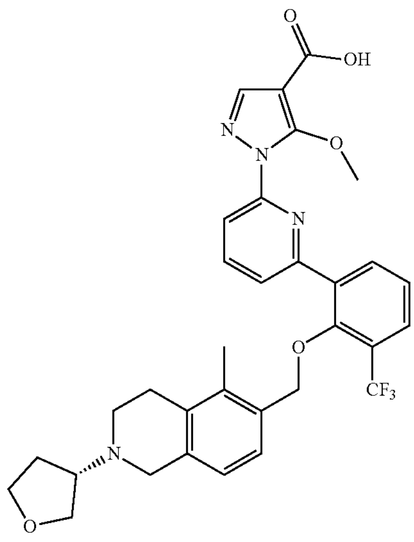 [SMILES: COc1c(C(=O)O)cnn1-c1cccc(-c2cccc(C(F)(F)F)c2OCc2ccc3c(c2C)CCN([C@H]2CCOC2)C3)n1] |
| 108 | 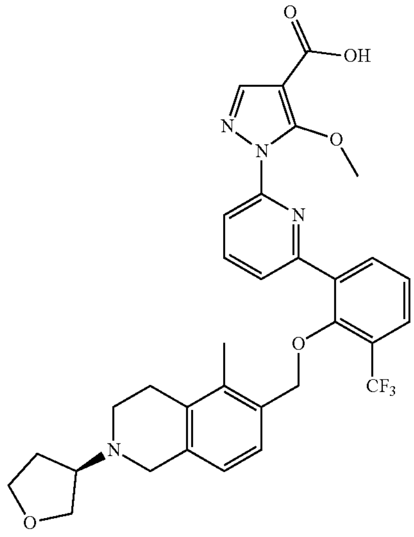 [SMILES: COc1c(C(=O)O)cnn1-c1cccc(-c2cccc(C(F)(F)F)c2OCc2ccc3c(c2C)CCN([C@@H]2CCOC2)C3)n1] |
| 109 | 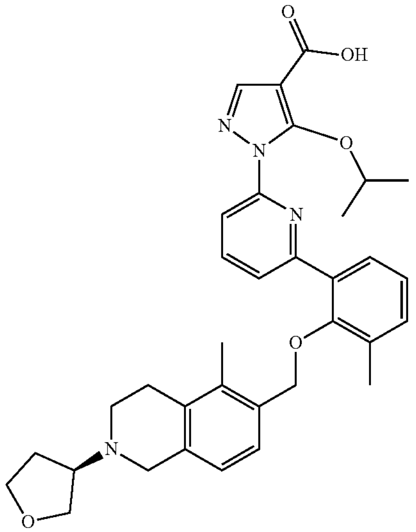 [SMILES: Cc1cccc(-c2cccc(-n3ncc(C(=O)O)c3OC(C)C)n2)c1OCc1ccc2c(c1C)CCN([C@@H]1CCOC1)C2] |
| 110 | 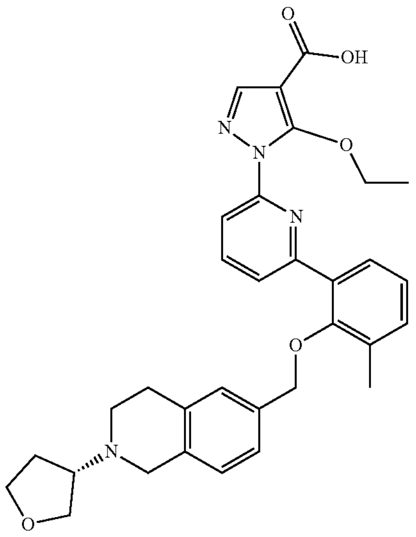 [SMILES: CCOc1c(C(=O)O)cnn1-c1cccc(-c2cccc(C)c2OCc2ccc3c(c2)CCN([C@H]2CCOC2)C3)n1] |
| 111 | 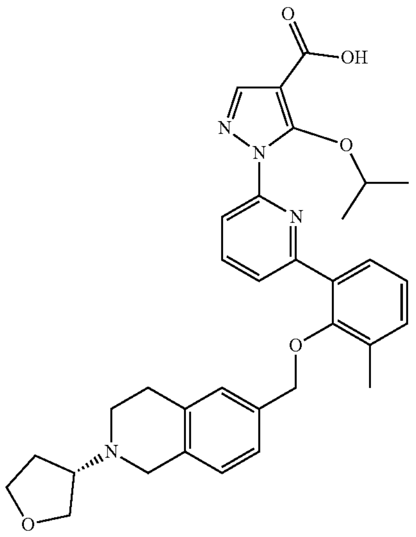 [SMILES: Cc1cccc(-c2cccc(-n3ncc(C(=O)O)c3OC(C)C)n2)c1OCc1ccc2c(c1)CCN([C@H]1CCOC1)C2] |

TABLE 1-continued
| Cpd No. | Structure |
| --- | --- |
| 112 | 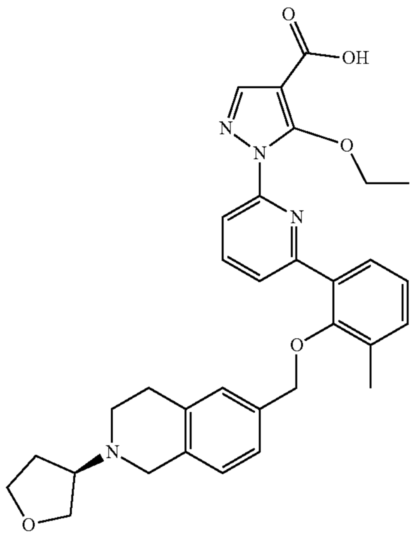 [SMILES: CCOc1c(C(=O)O)cnn1-c1cccc(-c2cccc(C)c2OCc2ccc3c(c2)CCN([C@@H]2CCOC2)C3)n1] |
| 113 | 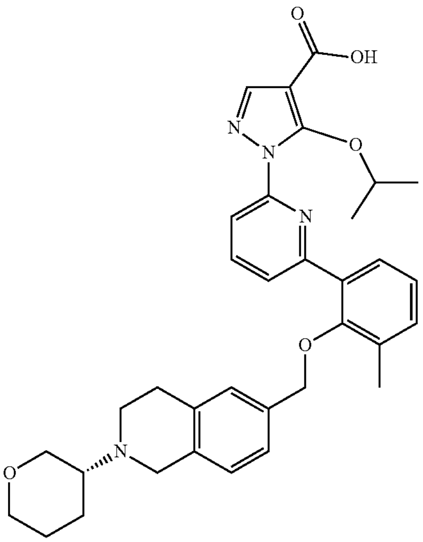 [SMILES: Cc1cccc(-c2cccc(-n3ncc(C(=O)O)c3OC(C)C)n2)c1OCc1ccc2c(c1)CCN([C@@H]1CCCOC1)C2] |
TABLE 1-continued
| Cpd No. | Structure |
| --- | --- |
| 114 | 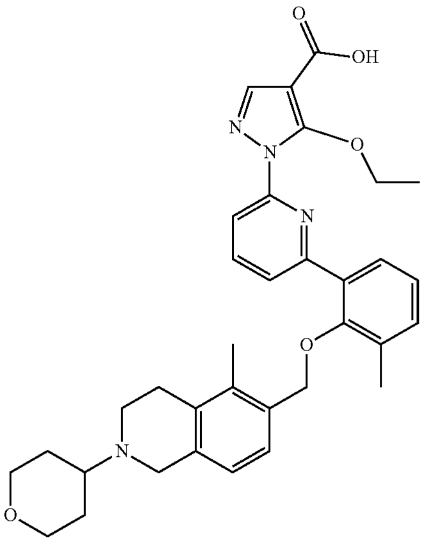 [SMILES: CCOc1c(C(=O)O)cnn1-c1cccc(-c2cccc(C)c2OCc2ccc3c(c2C)CCN(C2CCOCC2)C3)n1] |
| 115 | 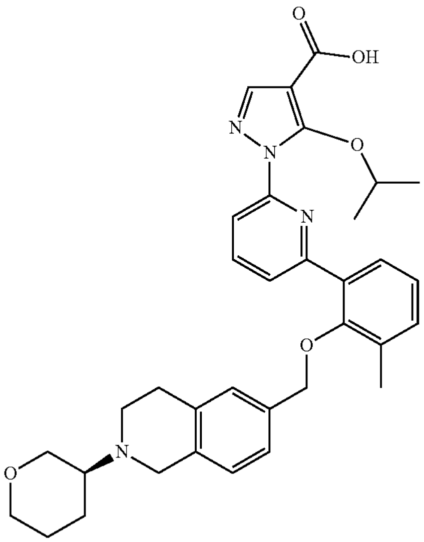 [SMILES: Cc1cccc(-c2cccc(-n3ncc(C(=O)O)c3OC(C)C)n2)c1OCc1ccc2c(c1)CCN([C@H]1CCCOC1)C2] |

TABLE 1-continued
| Cpd No. | Structure |
|---|---|
| 116 | 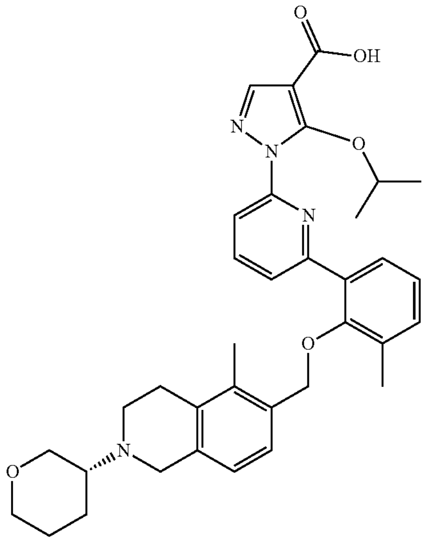 [SMILES: Cc1cccc(-c2cccc(-n3ncc(C(=O)O)c3OC(C)C)n2)c1OCc1ccc2c(c1C)CCN([C@@H]1CCCOC1)C2] |
| 117 | 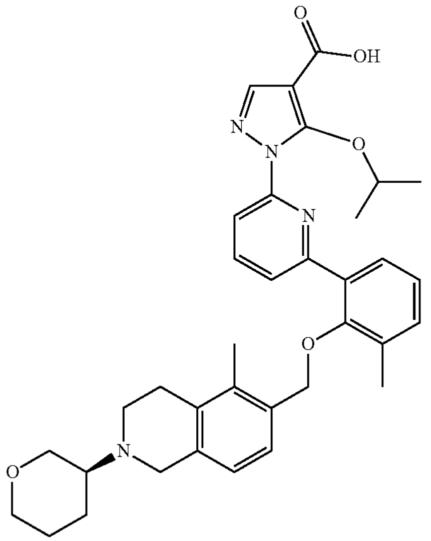 [SMILES: Cc1cccc(-c2cccc(-n3ncc(C(=O)O)c3OC(C)C)n2)c1OCc1ccc2c(c1C)CCN([C@H]1CCCOC1)C2] |
| 118 | 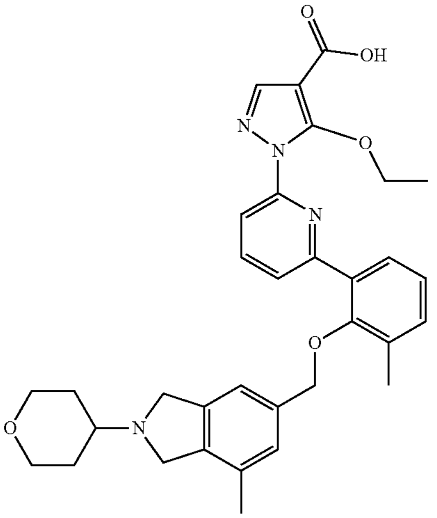 [SMILES: CCOc1c(C(=O)O)cnn1-c1cccc(-c2cccc(C)c2OCc2cc(C)c3c(c2)CN(C2CCOCC2)C3)n1] |
TABLE 1-continued
| Cpd No. | Structure |
|---|---|
| 119 | 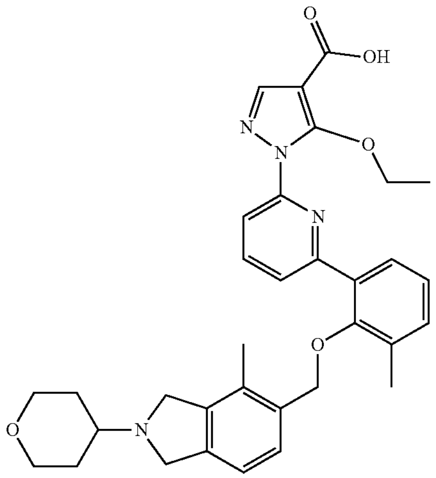 [SMILES: CCOc1c(C(=O)O)cnn1-c1cccc(-c2cccc(C)c2OCc2ccc3c(c2C)CN(C2CCOCC2)C3)n1] |
| 120 | 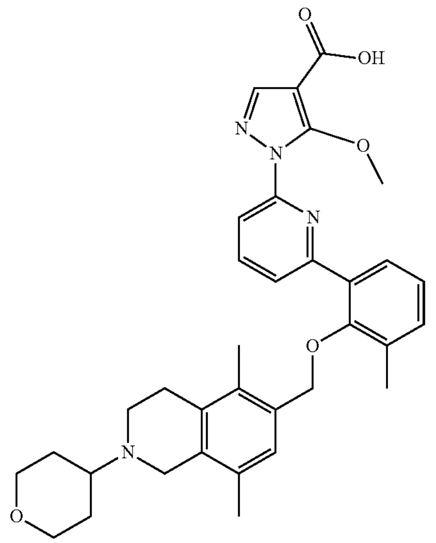 [SMILES: COc1c(C(=O)O)cnn1-c1cccc(-c2cccc(C)c2OCc2cc(C)c3c(c2C)CCN(C2CCOCC2)C3)n1] |
| 121 | 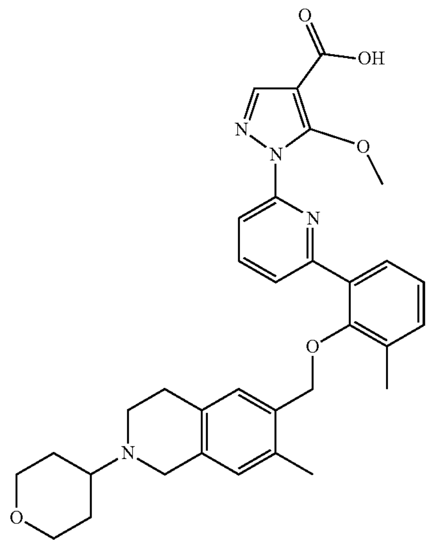 [SMILES: COc1c(C(=O)O)cnn1-c1cccc(-c2cccc(C)c2OCc2cc3c(cc2C)CN(C2CCOCC2)CC3)n1] |

TABLE 1-continued
| Cpd No. | Structure |
|---|---|
| 122 | 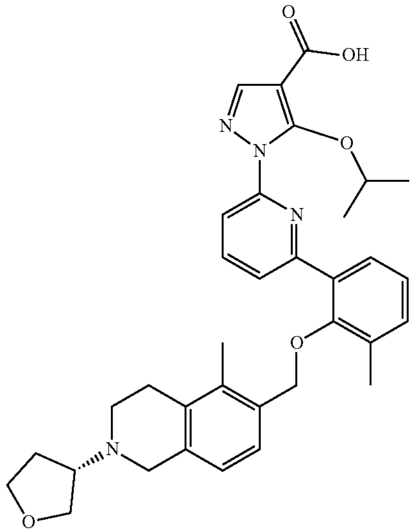 [SMILES: Cc1cccc(-c2cccc(-n3ncc(C(=O)O)c3OC(C)C)n2)c1OCc1ccc2c(c1C)CCN([C@H]1CCOC1)C2] |
| 123 | 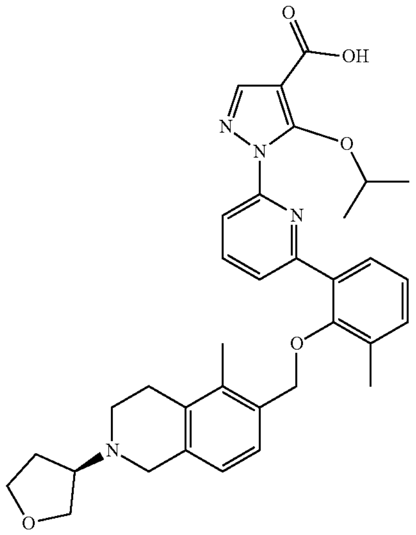 [SMILES: Cc1cccc(-c2cccc(-n3ncc(C(=O)O)c3OC(C)C)n2)c1OCc1ccc2c(c1C)CCN([C@@H]1CCOC1)C2] |
TABLE 1-continued
| Cpd No. | Structure |
|---|---|
| 124 | 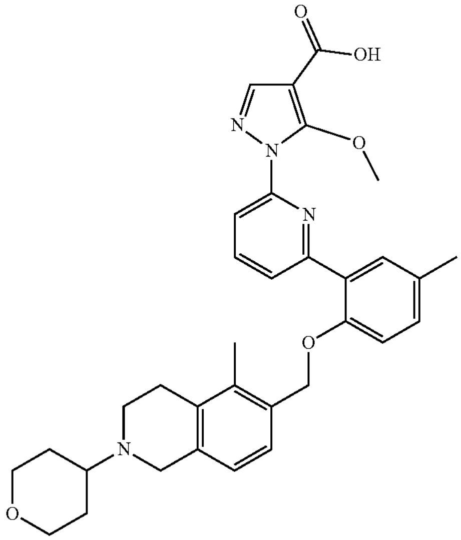 [SMILES: COc1c(C(=O)O)cnn1-c1cccc(-c2cc(C)ccc2OCc2ccc3c(c2C)CCN(C2CCOCC2)C3)n1] |
| 125 | 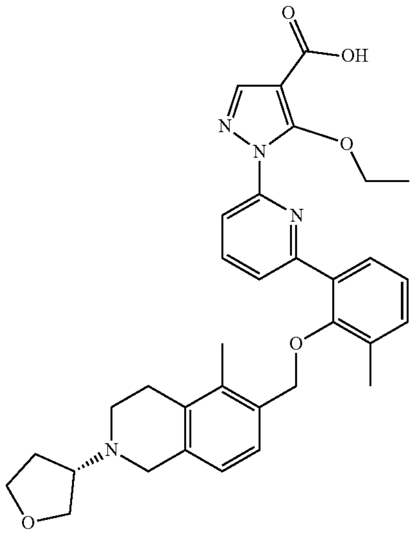 [SMILES: CCOc1c(C(=O)O)cnn1-c1cccc(-c2cccc(C)c2OCc2ccc3c(c2C)CCN([C@H]2CCOC2)C3)n1] |

TABLE 1-continued
| Cpd No. | Structure |
|---|---|
| 126 | 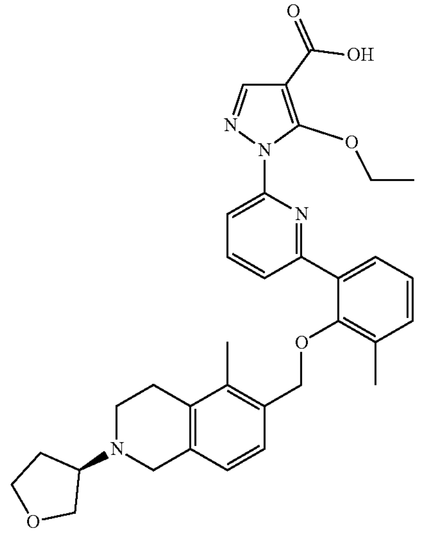 [SMILES: CCOc1c(C(=O)O)cnn1-c1cccc(-c2cccc(C)c2OCc2ccc3c(c2C)CCN([C@@H]2CCOC2)C3)n1] |
| 127 | 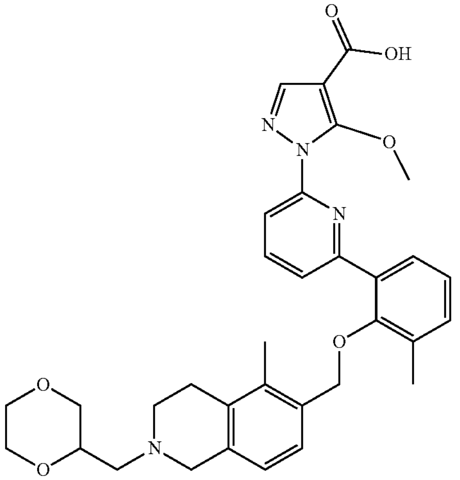 [SMILES: COc1c(C(=O)O)cnn1-c1cccc(-c2cccc(C)c2OCc2ccc3c(c2C)CCN(CC2COCCO2)C3)n1] |
| 128 | 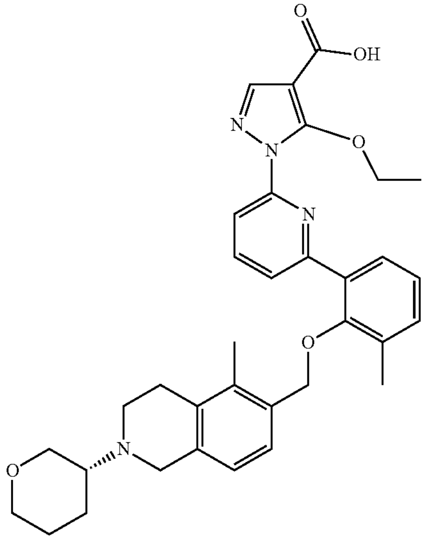 [SMILES: CCOc1c(C(=O)O)cnn1-c1cccc(-c2cccc(C)c2OCc2ccc3c(c2C)CCN([C@@H]2CCCOC2)C3)n1] |
TABLE 1-continued
| Cpd No. | Structure |
|---|---|
| 129 | 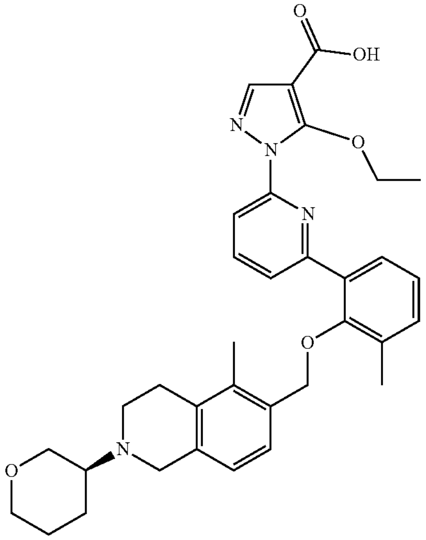 [SMILES: CCOc1c(C(=O)O)cnn1-c1cccc(-c2cccc(C)c2OCc2ccc3c(c2C)CCN([C@H]2CCCOC2)C3)n1] |
| 130 | 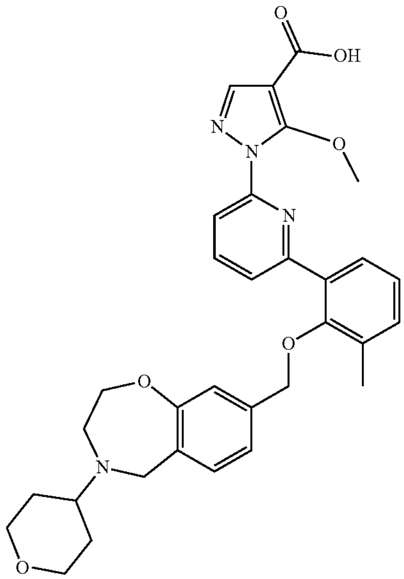 [SMILES: COc1c(C(=O)O)cnn1-c1cccc(-c2cccc(C)c2OCc2ccc3c(c2)OCCN(C2CCOCC2)C3)n1] |

TABLE 1-continued
| Cpd No. | Structure |
|---|---|
| 131 | 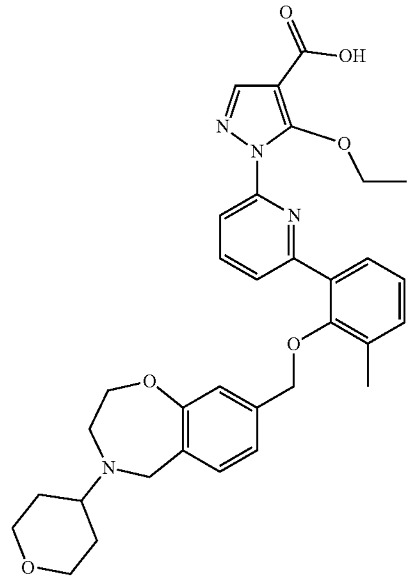 [SMILES: CCOc1c(C(=O)O)cnn1-c1cccc(-c2cccc(C)c2OCc2ccc3c(c2)OCCN(C2CCOCC2)C3)n1] |
| 132 | 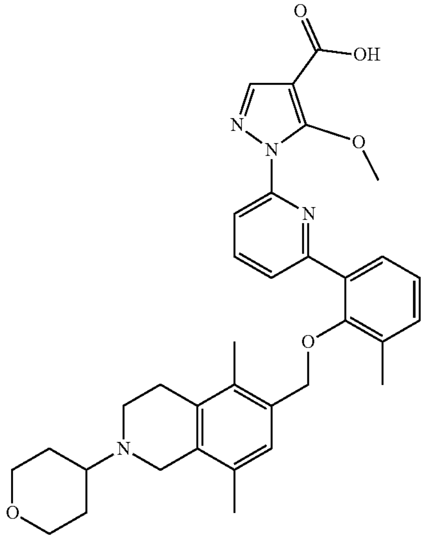 [SMILES: COc1c(C(=O)O)cnn1-c1cccc(-c2cccc(C)c2OCc2cc(C)c3c(c2C)CCN(C2CCOCC2)C3)n1] |
TABLE 1-continued
| Cpd No. | Structure |
|---|---|
| 133 | 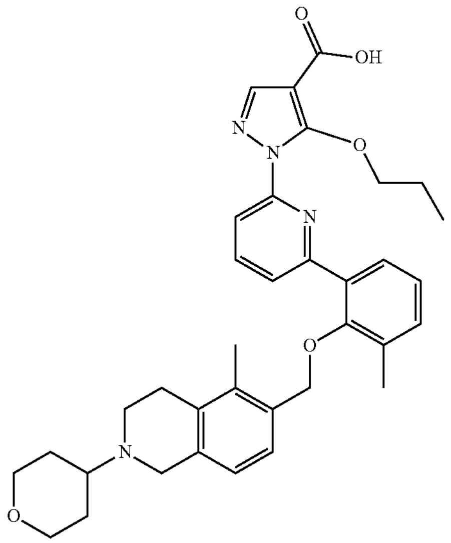 [SMILES: CCCOc1c(C(=O)O)cnn1-c1cccc(-c2cccc(C)c2OCc2ccc3c(c2C)CCN(C2CCOCC2)C3)n1] |
| 134 | 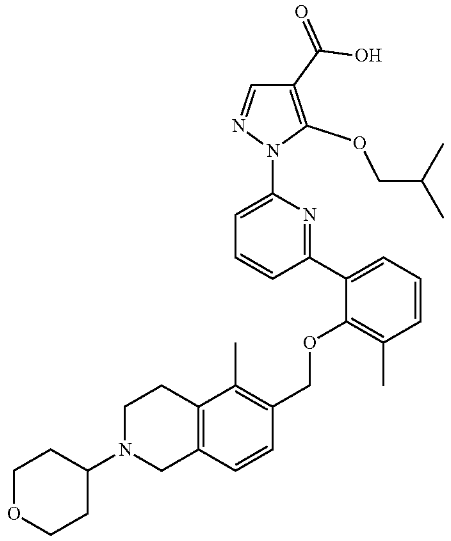 [SMILES: Cc1cccc(-c2cccc(-n3ncc(C(=O)O)c3OCC(C)C)n2)c1OCc1ccc2c(c1C)CCN(C1CCOCC1)C2] |

TABLE 1-continued
| Cpd No. | Structure |
|---|---|
| 135 | 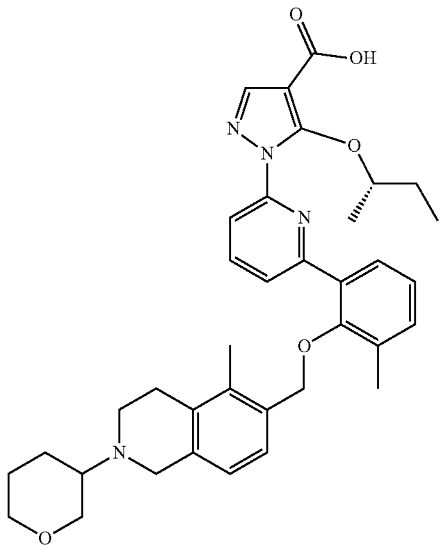 [SMILES: CC[C@H](C)Oc1c(C(=O)O)cnn1-c1cccc(-c2cccc(C)c2OCc2ccc3c(c2C)CCN(C2CCCOC2)C3)n1] |
| 136 | 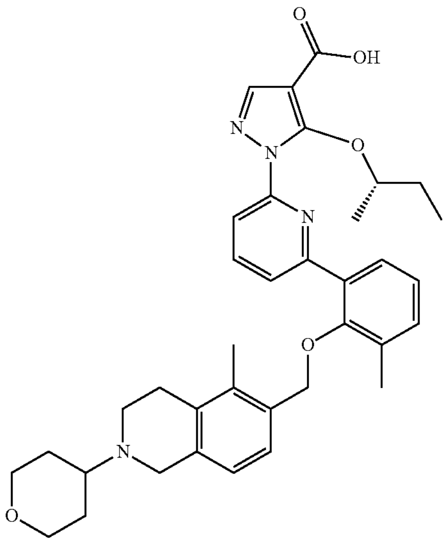 [SMILES: CC[C@H](C)Oc1c(C(=O)O)cnn1-c1cccc(-c2cccc(C)c2OCc2ccc3c(c2C)CCN(C2CCOCC2)C3)n1] |
| 137 | 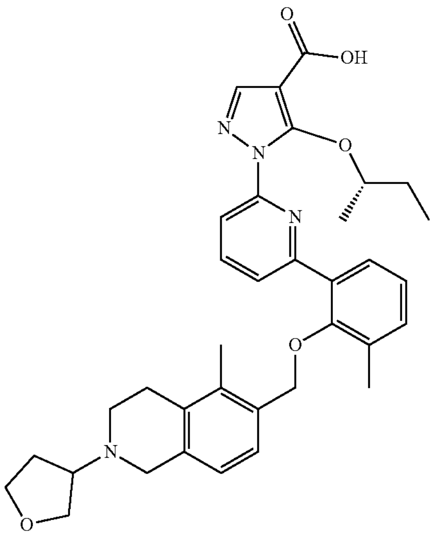 [SMILES: CC[C@H](C)Oc1c(C(=O)O)cnn1-c1cccc(-c2cccc(C)c2OCc2ccc3c(c2C)CCN(C2CCOC2)C3)n1] |
| 138 | 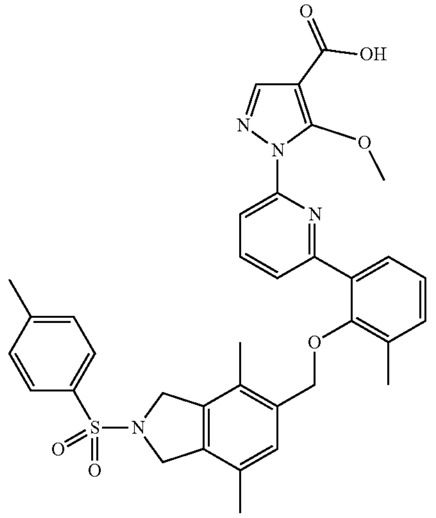 [SMILES: COc1c(C(=O)O)cnn1-c1cccc(-c2cccc(C)c2OCc2cc(C)c3c(c2C)CN(S(=O)(=O)c2ccc(C)cc2)C3)n1] |
| 139 | 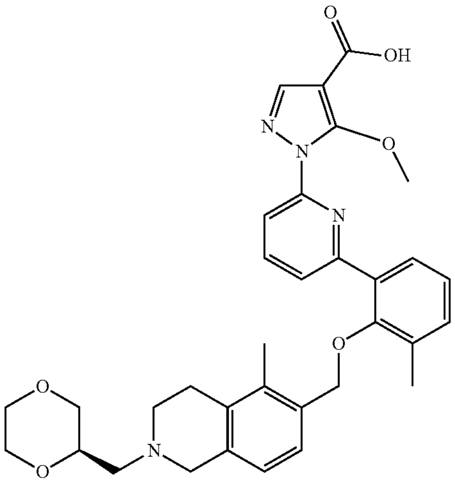 [SMILES: COc1c(C(=O)O)cnn1-c1cccc(-c2cccc(C)c2OCc2ccc3c(c2C)CCN(C[C@@H]2COCCO2)C3)n1] |

TABLE 1-continued
| Cpd No. | Structure |
| --- | --- |
| 140 | 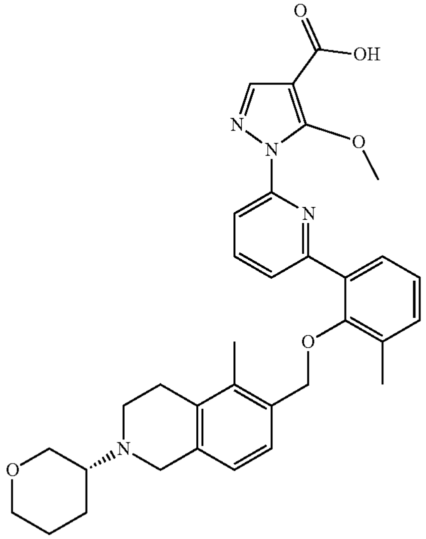 [SMILES: COc1c(C(=O)O)cnn1-c1cccc(-c2cccc(C)c2OCc2ccc3c(c2C)CCN([C@@H]2CCCOC2)C3)n1] |
| 141 | 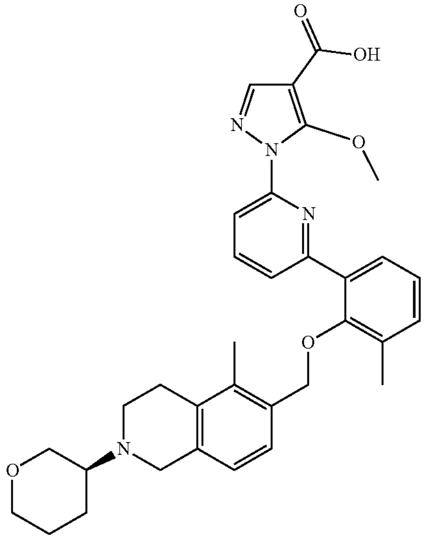 [SMILES: COc1c(C(=O)O)cnn1-c1cccc(-c2cccc(C)c2OCc2ccc3c(c2C)CCN([C@H]2CCCOC2)C3)n1] |
| 142 | 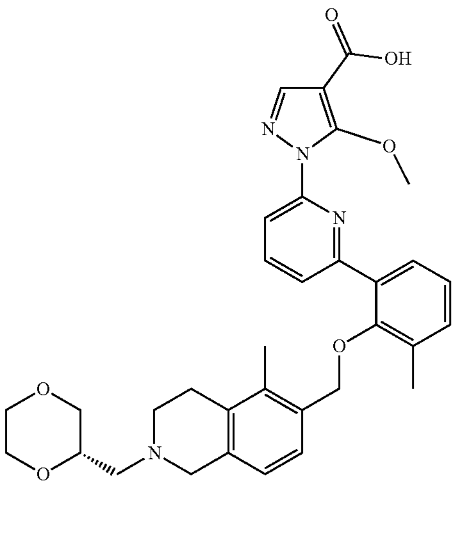 [SMILES: COc1c(C(=O)O)cnn1-c1cccc(-c2cccc(C)c2OCc2ccc3c(c2C)CCN(C[C@H]2COCCO2)C3)n1] |
TABLE 1-continued
| Cpd No. | Structure |
| --- | --- |
| 143 | 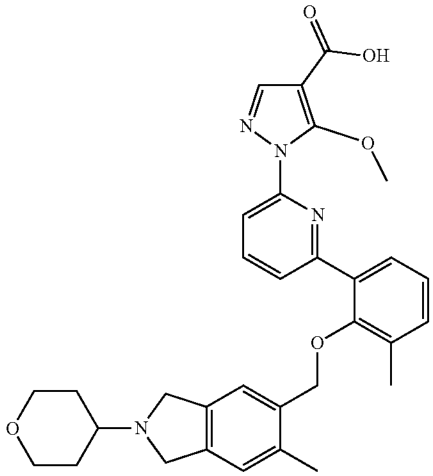 [SMILES: COc1c(C(=O)O)cnn1-c1cccc(-c2cccc(C)c2OCc2cc3c(cc2C)CN(C2CCOCC2)C3)n1] |
| 144 | 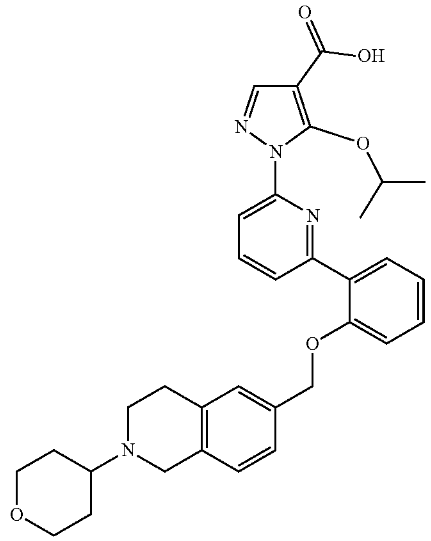 [SMILES: CC(C)Oc1c(C(=O)O)cnn1-c1cccc(-c2ccccc2OCc2ccc3c(c2)CCN(C2CCOCC2)C3)n1] |
| 145 | 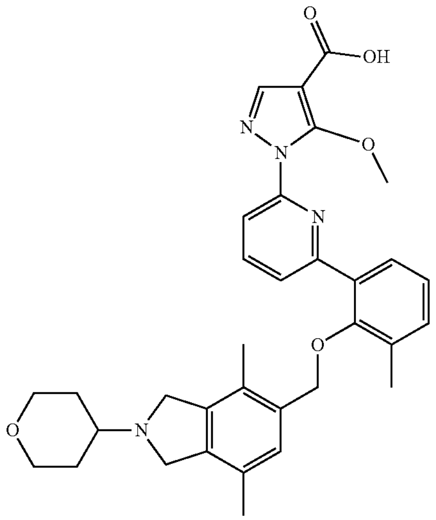 [SMILES: COc1c(C(=O)O)cnn1-c1cccc(-c2cccc(C)c2OCc2cc(C)c3c(c2C)CN(C2CCOCC2)C3)n1] |

TABLE 1-continued
| Cpd No. | Structure |
| --- | --- |
| 146 | 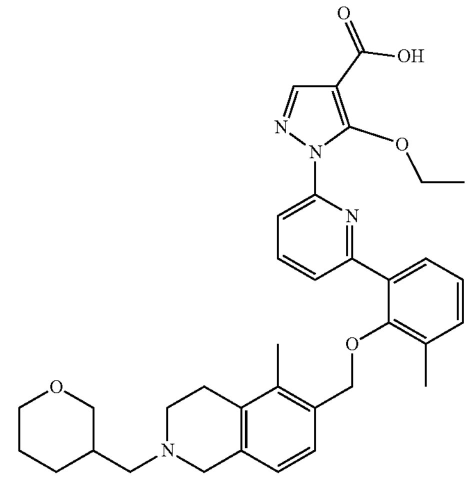 |
| 147 | 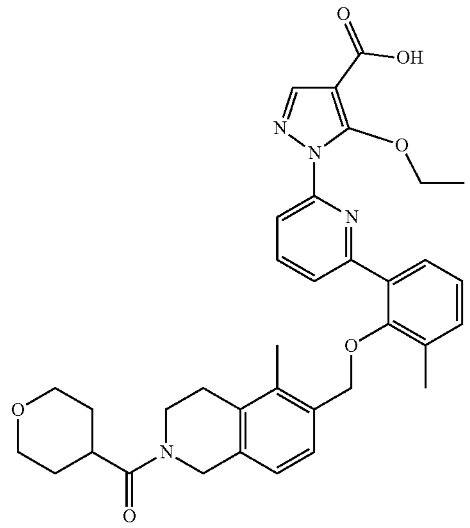 [SMILES: CCOc1c(C(=O)O)cnn1-c1cccc(-c2cccc(C)c2OCc2ccc3c(c2C)CCN(C(=O)C2CCOCC2)C3)n1] |
| 148 | 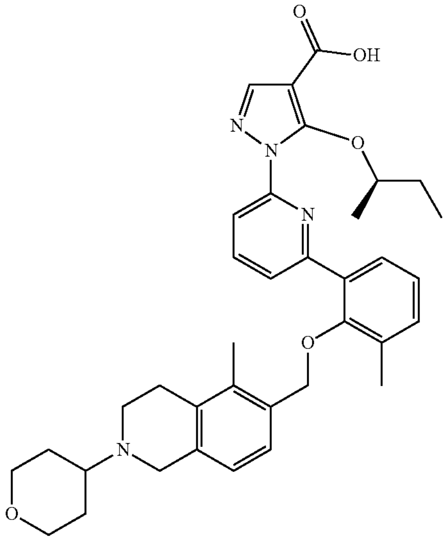 [SMILES: CC[C@@H](C)Oc1c(C(=O)O)cnn1-c1cccc(-c2cccc(C)c2OCc2ccc3c(c2C)CCN(C2CCOCC2)C3)n1] |
TABLE 1-continued
| Cpd No. | Structure |
| --- | --- |
| 149 | 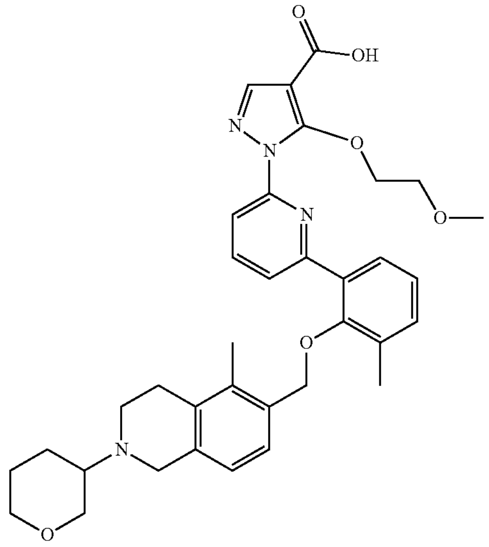 [SMILES: COCCOc1c(C(=O)O)cnn1-c1cccc(-c2cccc(C)c2OCc2ccc3c(c2C)CCN(C2CCCOC2)C3)n1] |
| 150 | 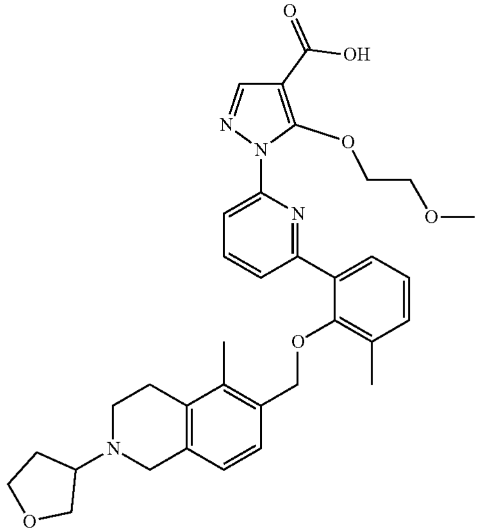 [SMILES: COCCOc1c(C(=O)O)cnn1-c1cccc(-c2cccc(C)c2OCc2ccc3c(c2C)CCN(C2CCOC2)C3)n1] |

TABLE 1-continued
| Cpd No. | Structure |
| --- | --- |
| 151 | 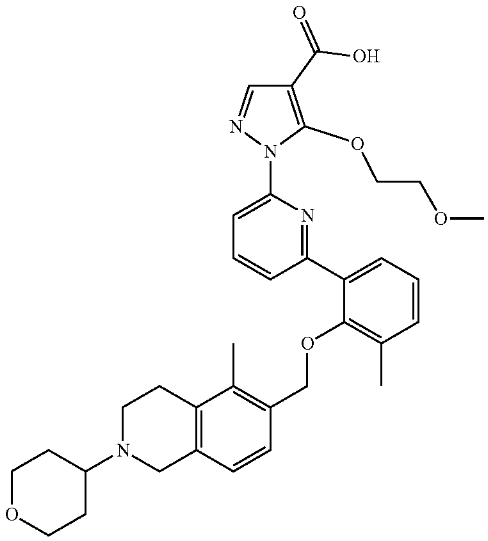 [SMILES: COCCOc1c(C(=O)O)cnn1-c1cccc(-c2cccc(C)c2OCc2ccc3c(c2C)CCN(C2CCOCC2)C3)n1] |
| 152 | 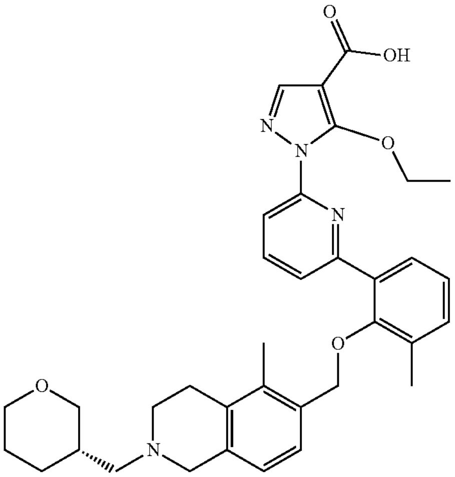 [SMILES: CCOc1c(C(=O)O)cnn1-c1cccc(-c2cccc(C)c2OCc2ccc3c(c2C)CCN(C[C@@H]2CCCOC2)C3)n1] |
| 153 | 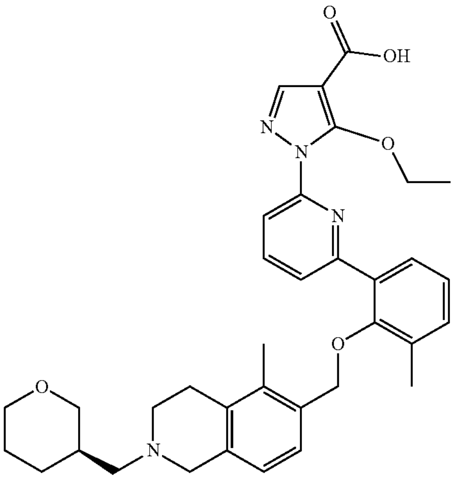 [SMILES: CCOc1c(C(=O)O)cnn1-c1cccc(-c2cccc(C)c2OCc2ccc3c(c2C)CCN(C[C@H]2CCCOC2)C3)n1] |
| 154 | 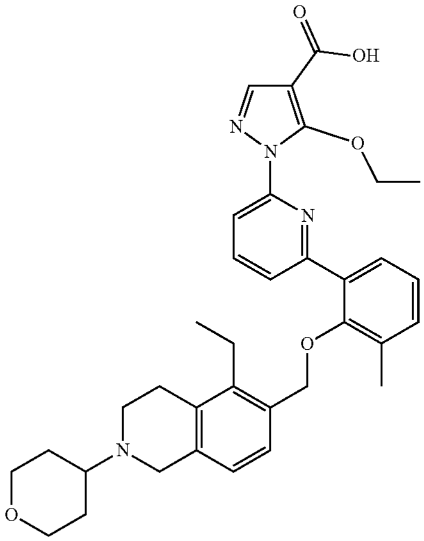 [SMILES: CCOc1c(C(=O)O)cnn1-c1cccc(-c2cccc(C)c2OCc2ccc3c(c2CC)CCN(C2CCOCC2)C3)n1] |
| 155 | 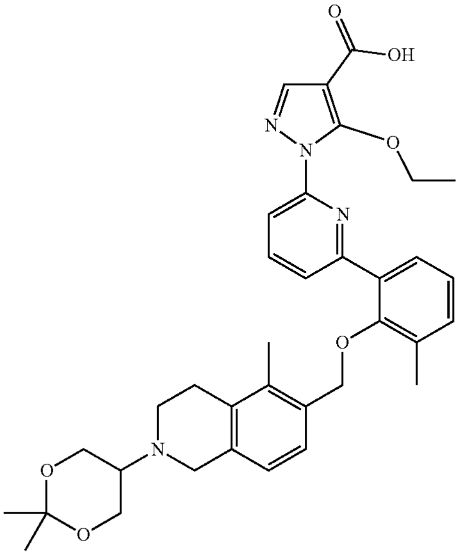 [SMILES: CCOc1c(C(=O)O)cnn1-c1cccc(-c2cccc(C)c2OCc2ccc3c(c2C)CCN(C2COC(C)(C)OC2)C3)n1] |

TABLE 1-continued
| Cpd No. | Structure |
|---|---|
| 156 | 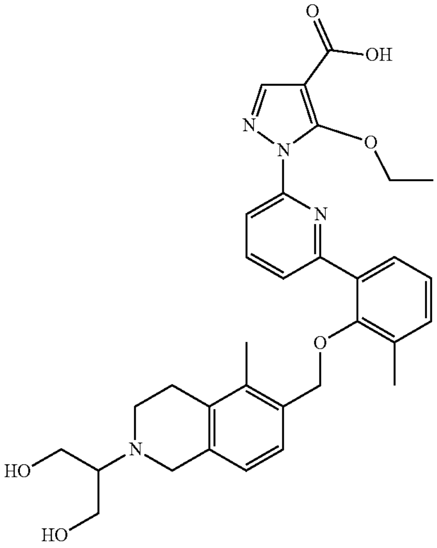 [SMILES: CCOc1c(C(=O)O)cnn1-c1cccc(-c2cccc(C)c2OCc2ccc3c(c2C)CCN(C(CO)CO)C3)n1] |
| 157 | 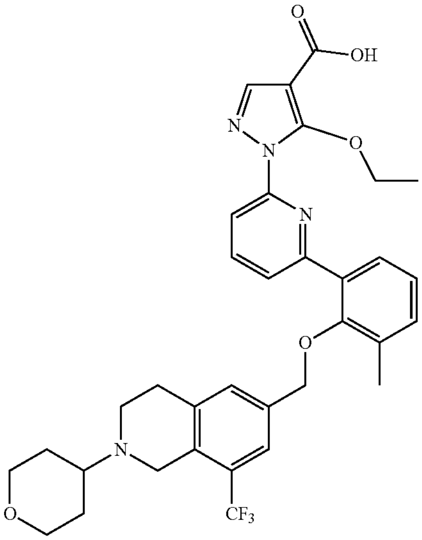 [SMILES: CCOc1c(C(=O)O)cnn1-c1cccc(-c2cccc(C)c2OCc2cc3c(c(C(F)(F)F)c2)CN(C2CCOCC2)CC3)n1] |
TABLE 1-continued
| Cpd No. | Structure |
|---|---|
| 158 | 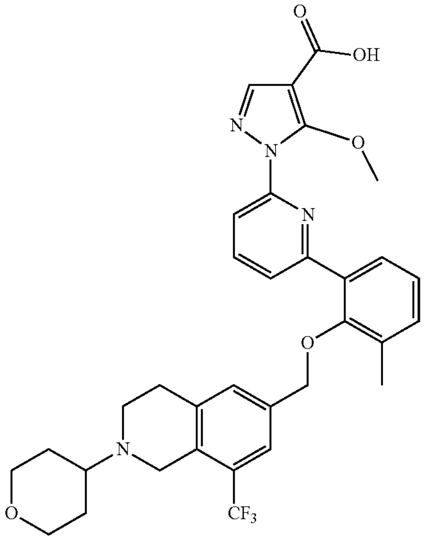 [SMILES: COc1c(C(=O)O)cnn1-c1cccc(-c2cccc(C)c2OCc2cc3c(c(C(F)(F)F)c2)CN(C2CCOCC2)CC3)n1] |
| 159 | 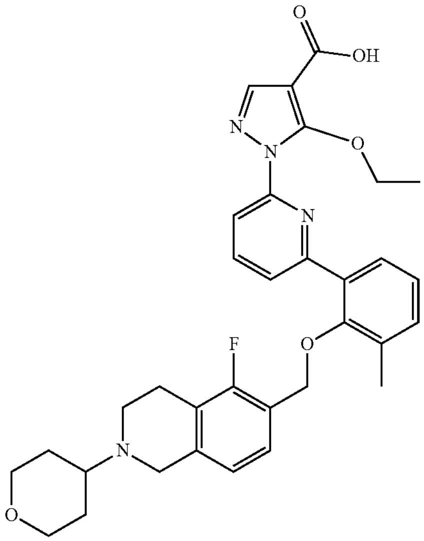 [SMILES: CCOc1c(C(=O)O)cnn1-c1cccc(-c2cccc(C)c2OCc2ccc3c(c2F)CCN(C2CCOCC2)C3)n1] |
| 160 | 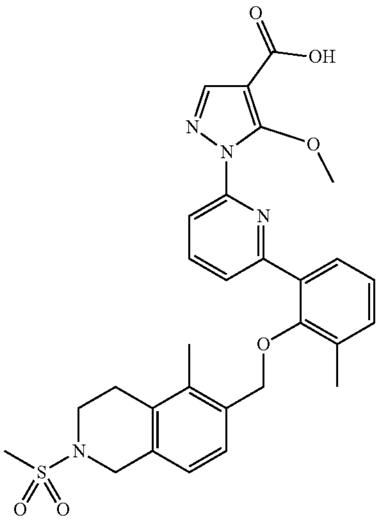 [SMILES: COc1c(C(=O)O)cnn1-c1cccc(-c2cccc(C)c2OCc2ccc3c(c2C)CCN(S(C)(=O)=O)C3)n1] |

TABLE 1-continued
| Cpd No. | Structure |
|---|---|
| 161 | 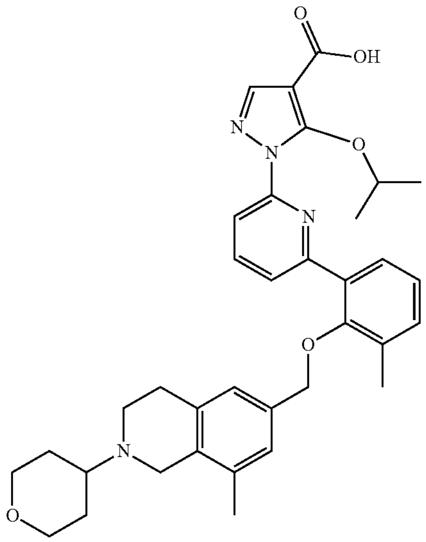 [SMILES: Cc1cc(COc2c(C)cccc2-c2cccc(-n3ncc(C(=O)O)c3OC(C)C)n2)cc2c1CN(C1CCOCC1)CC2] |
| 162 | 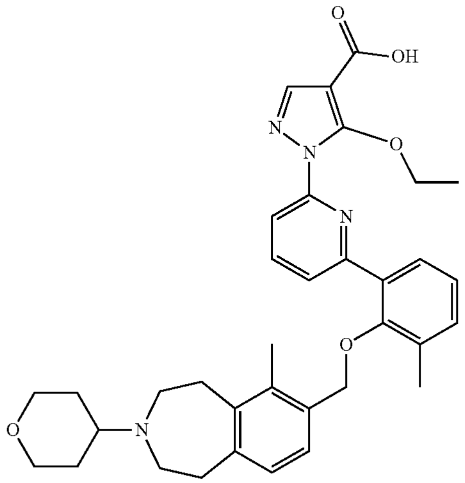 [SMILES: CCOc1c(C(=O)O)cnn1-c1cccc(-c2cccc(C)c2OCc2ccc3c(c2C)CCN(C2CCOCC2)CC3)n1] |
| 163 | 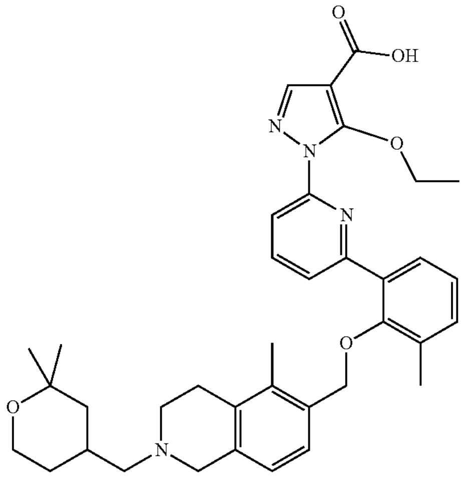 [SMILES: CCOc1c(C(=O)O)cnn1-c1cccc(-c2cccc(C)c2OCc2ccc3c(c2C)CCN(CC2CCOC(C)(C)C2)C3)n1] |
| 164 | 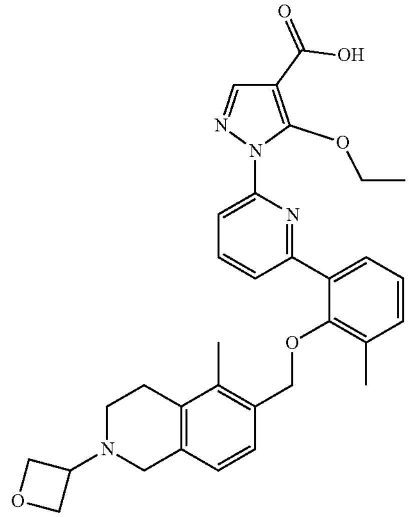 [SMILES: CCOc1c(C(=O)O)cnn1-c1cccc(-c2cccc(C)c2OCc2ccc3c(c2C)CCN(C2COC2)C3)n1] |
| 165 | 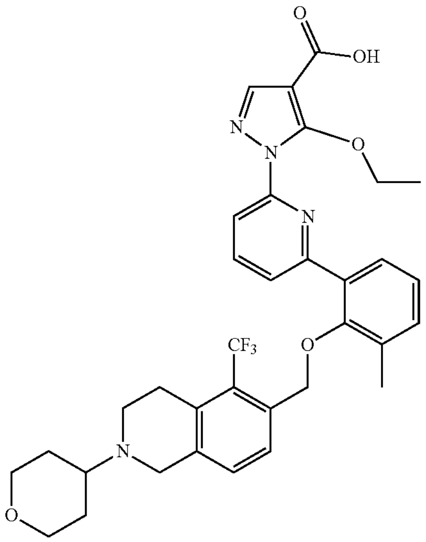 [SMILES: CCOc1c(C(=O)O)cnn1-c1cccc(-c2cccc(C)c2OCc2ccc3c(c2C(F)(F)F)CCN(C2CCOCC2)C3)n1] |
| 166 | 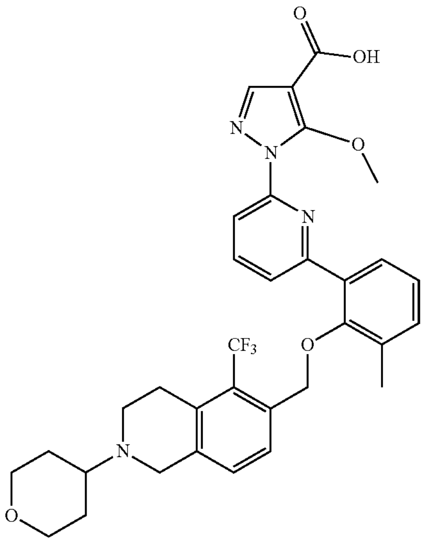 [SMILES: COc1c(C(=O)O)cnn1-c1cccc(-c2cccc(C)c2OCc2ccc3c(c2C(F)(F)F)CCN(C2CCOCC2)C3)n1] |

TABLE 1-continued
| Cpd No. | Structure |
|---|---|
| 167 | 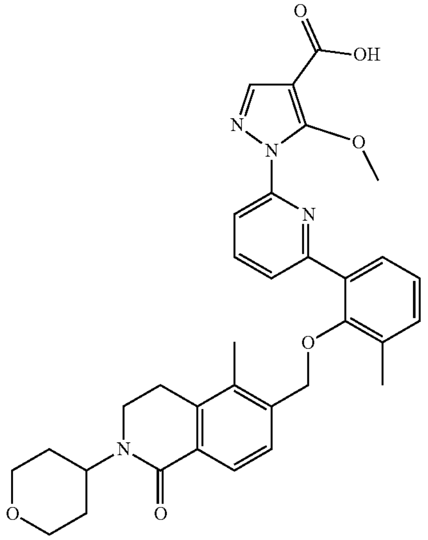 [SMILES: COc1c(C(=O)O)cnn1-c1cccc(-c2cccc(C)c2OCc2ccc3c(c2C)CCN(C2CCOCC2)C3=O)n1] |
| 168 | 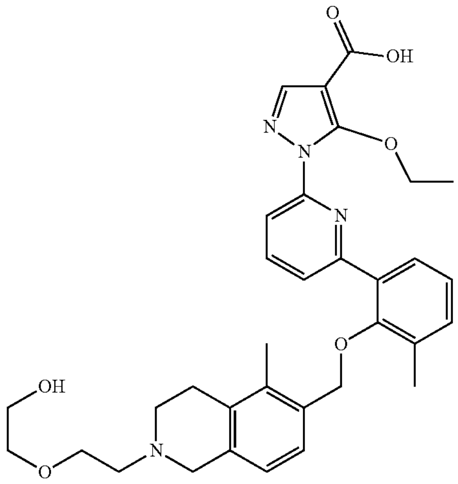 [SMILES: CCOc1c(C(=O)O)cnn1-c1cccc(-c2cccc(C)c2OCc2ccc3c(c2C)CCN(CCOCCO)C3)n1] |
| 169 | 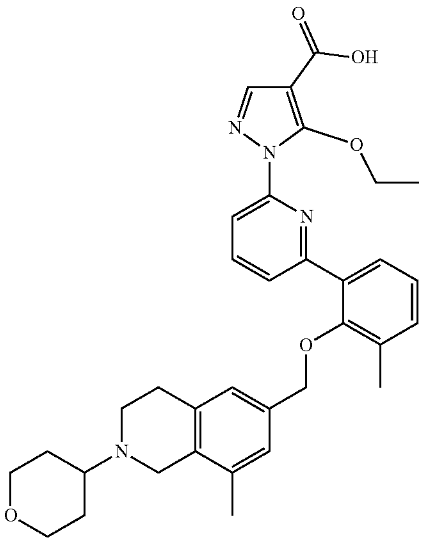 [SMILES: CCOc1c(C(=O)O)cnn1-c1cccc(-c2cccc(C)c2OCc2cc(C)c3c(c2)CCN(C2CCOCC2)C3)n1] |
TABLE 1-continued
| Cpd No. | Structure |
|---|---|
| 170 | 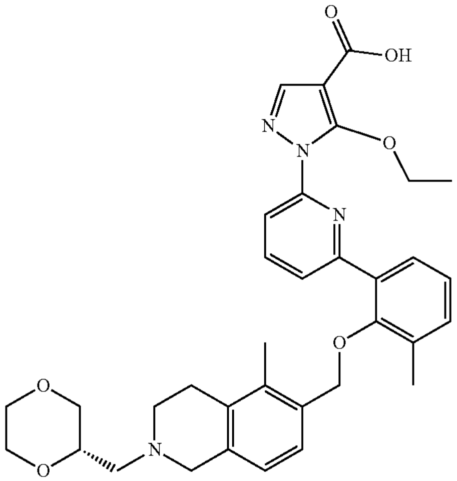 [SMILES: CCOc1c(C(=O)O)cnn1-c1cccc(-c2cccc(C)c2OCc2ccc3c(c2C)CCN(C[C@H]2COCCO2)C3)n1] |
| 171 | 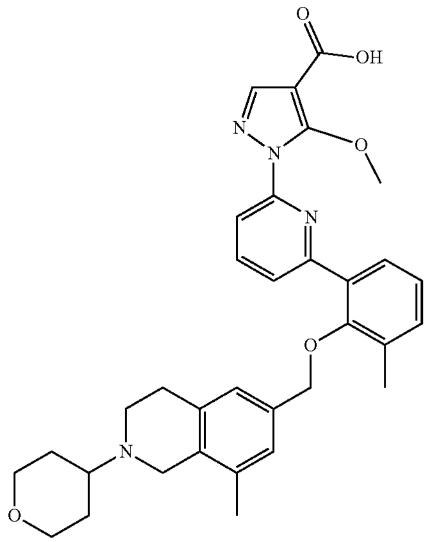 [SMILES: COc1c(C(=O)O)cnn1-c1cccc(-c2cccc(C)c2OCc2cc(C)c3c(c2)CCN(C2CCOCC2)C3)n1] |
| 172 | 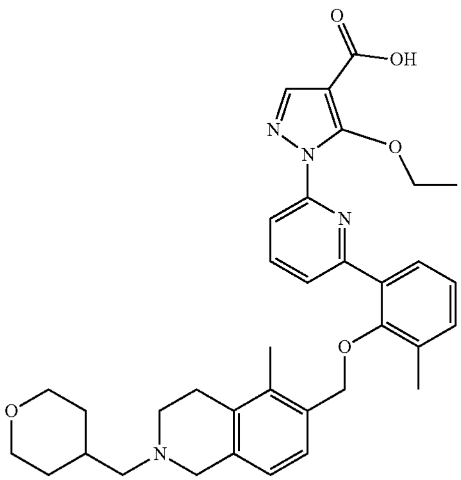 [SMILES: CCOc1c(C(=O)O)cnn1-c1cccc(-c2cccc(C)c2OCc2ccc3c(c2C)CCN(CC2CCOCC2)C3)n1] |

TABLE 1-continued
| Cpd No. | Structure |
| --- | --- |
| 173 | 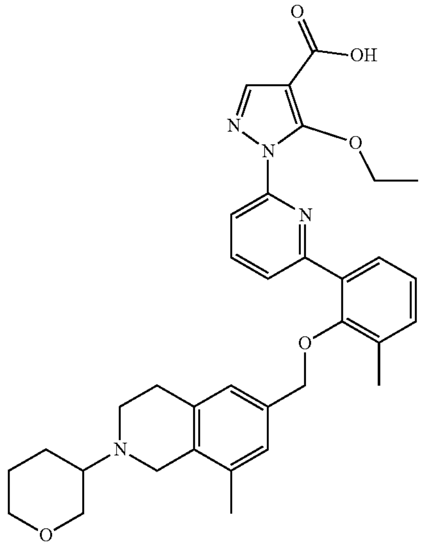 [SMILES: CCOc1c(C(=O)O)cnn1-c1cccc(-c2cccc(C)c2OCc2cc(C)c3c(c2)CCN(C2CCCOC2)C3)n1] |
| 174 | 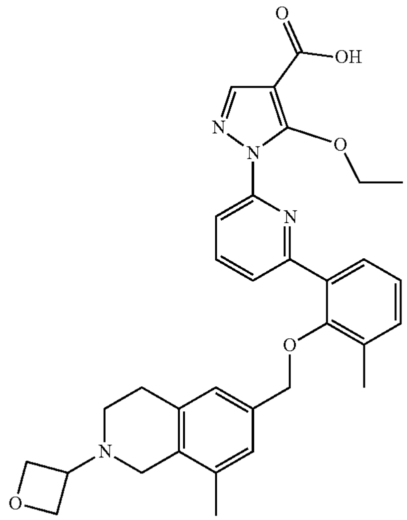 [SMILES: CCOc1c(C(=O)O)cnn1-c1cccc(-c2cccc(C)c2OCc2cc(C)c3c(c2)CCN(C2COC2)C3)n1] |
| 175 | 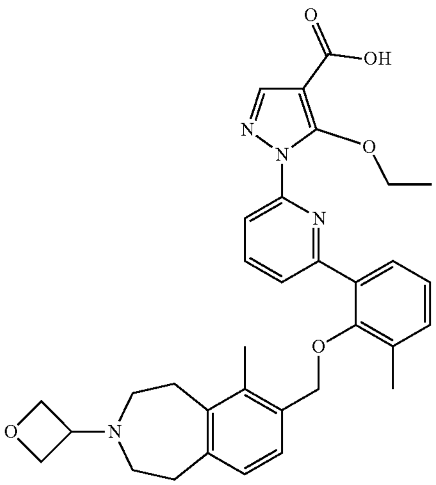 [SMILES: CCOc1c(C(=O)O)cnn1-c1cccc(-c2cccc(C)c2OCc2ccc3c(c2C)CCN(C2COC2)CC3)n1] |
TABLE 1-continued
| Cpd No. | Structure |
| --- | --- |
| 176 | 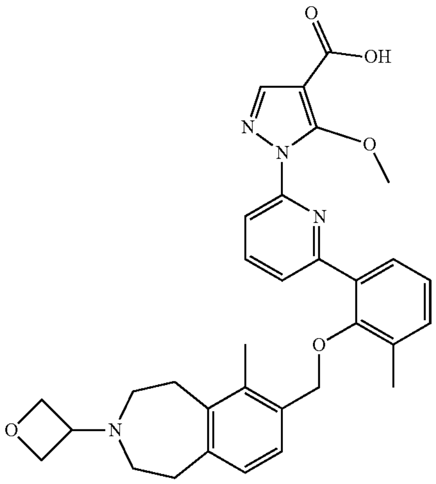 [SMILES: COc1c(C(=O)O)cnn1-c1cccc(-c2cccc(C)c2OCc2ccc3c(c2C)CCN(C2COC2)CC3)n1] |
| 177 | 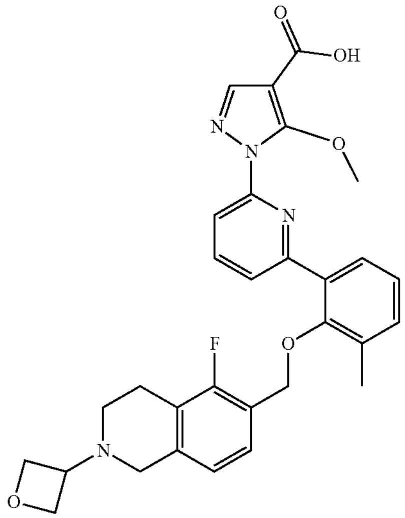 [SMILES: COc1c(C(=O)O)cnn1-c1cccc(-c2cccc(C)c2OCc2ccc3c(c2F)CCN(C2COC2)C3)n1] |
| 178 | 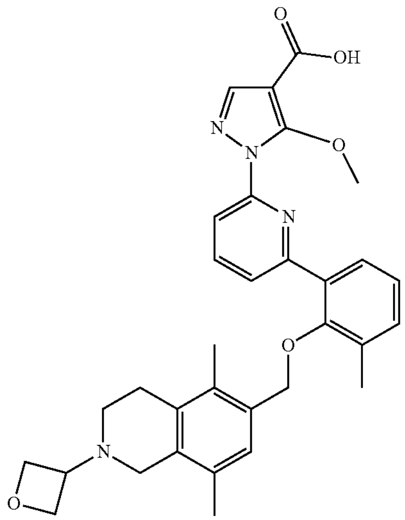 [SMILES: COc1c(C(=O)O)cnn1-c1cccc(-c2cccc(C)c2OCc2cc(C)c3c(c2C)CCN(C2COC2)C3)n1] |

TABLE 1-continued
| Cpd No. | Structure |
| --- | --- |
| 179 | 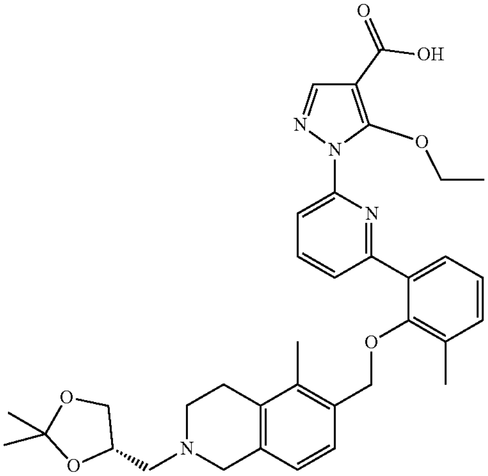 [SMILES: CCOc1c(C(=O)O)cnn1-c1cccc(-c2cccc(C)c2OCc2ccc3c(c2C)CCN(C[C@H]2COC(C)(C)O2)C3)n1] |
| 180 | 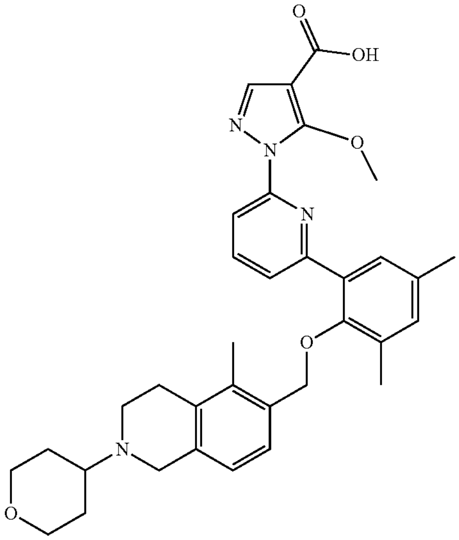 [SMILES: COc1c(C(=O)O)cnn1-c1cccc(-c2cc(C)cc(C)c2OCc2ccc3c(c2C)CCN(C2CCOCC2)C3)n1] |
| 181 | 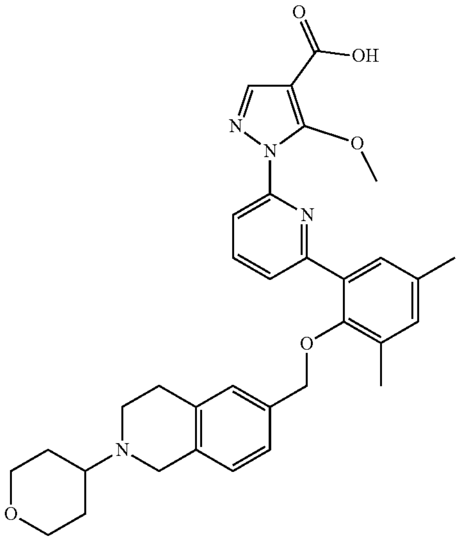 [SMILES: COc1c(C(=O)O)cnn1-c1cccc(-c2cc(C)cc(C)c2OCc2ccc3c(c2)CCN(C2CCOCC2)C3)n1] |
TABLE 1-continued
| Cpd No. | Structure |
| --- | --- |
| 182 | 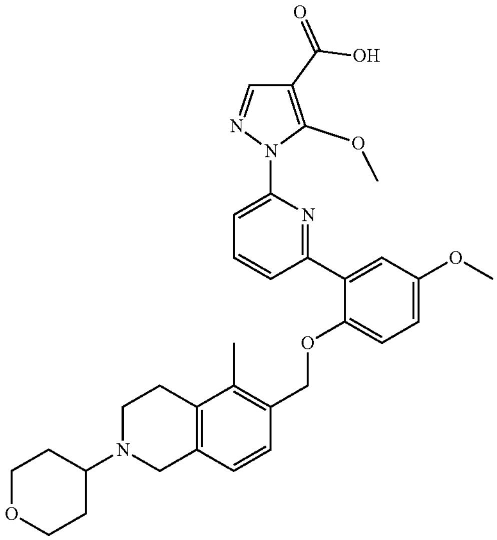 [SMILES: COc1ccc(OCc2ccc3c(c2C)CCN(C2CCOCC2)C3)c(-c2cccc(-n3ncc(C(=O)O)c3OC)n2)c1] |
| 183 | 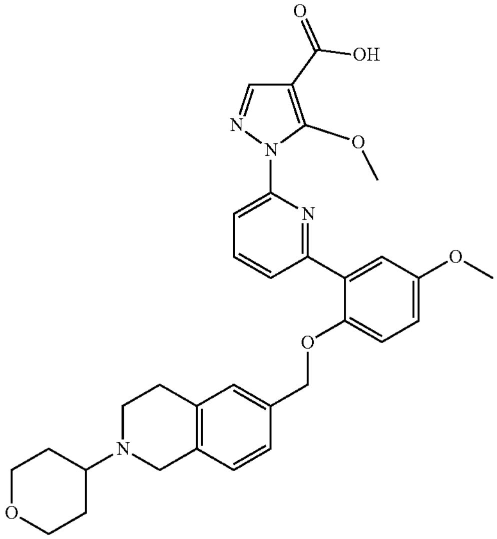 [SMILES: COc1ccc(OCc2ccc3c(c2)CCN(C2CCOCC2)C3)c(-c2cccc(-n3ncc(C(=O)O)c3OC)n2)c1] |
| 184 | 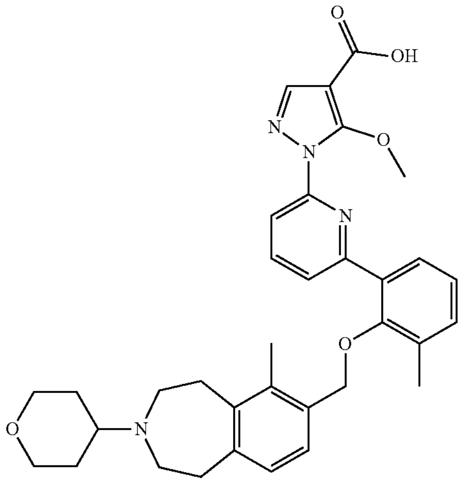 [SMILES: COc1c(C(=O)O)cnn1-c1cccc(-c2cccc(C)c2OCc2ccc3c(c2C)CCN(C2CCOCC2)CC3)n1] |

TABLE 1-continued
| Cpd No. | Structure |
| --- | --- |
| 185 | 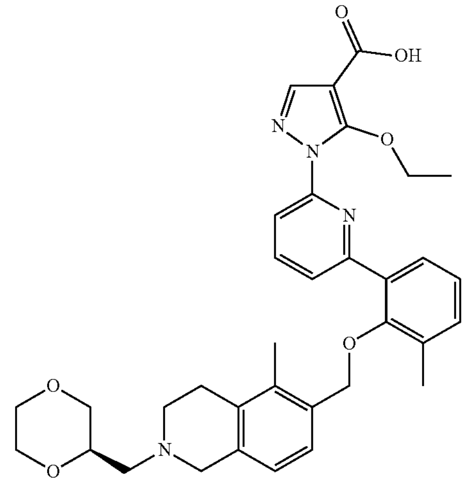 |
| 186 | 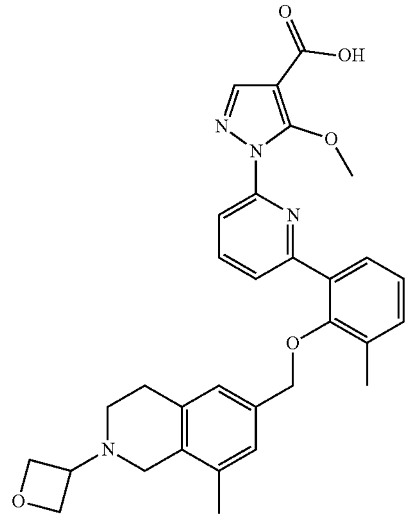 [SMILES: COc1c(C(=O)O)cnn1-c1cccc(-c2cccc(C)c2OCc2cc(C)c3c(c2)CCN(C2COC2)C3)n1] |
| 187 | 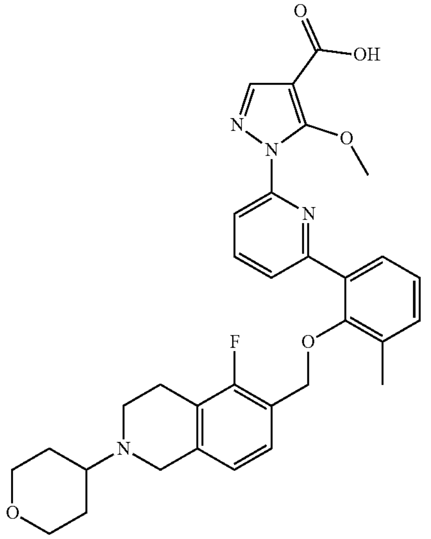 [SMILES: COc1c(C(=O)O)cnn1-c1cccc(-c2cccc(C)c2OCc2ccc3c(c2F)CCN(C2CCOCC2)C3)n1] |
TABLE 1-continued
| Cpd No. | Structure |
| --- | --- |
| 188 | 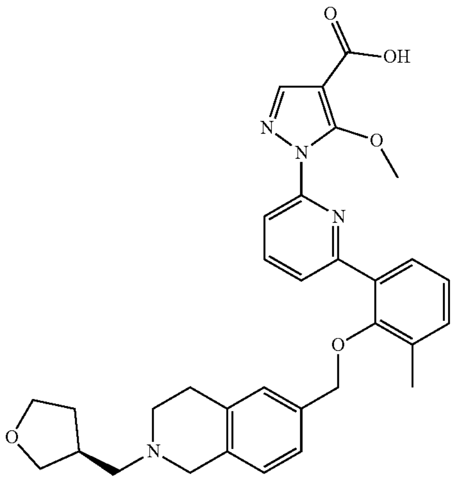 [SMILES: COc1c(C(=O)O)cnn1-c1cccc(-c2cccc(C)c2OCc2ccc3c(c2)CCN(C[C@@H]2CCOC2)C3)n1] |
| 189 | 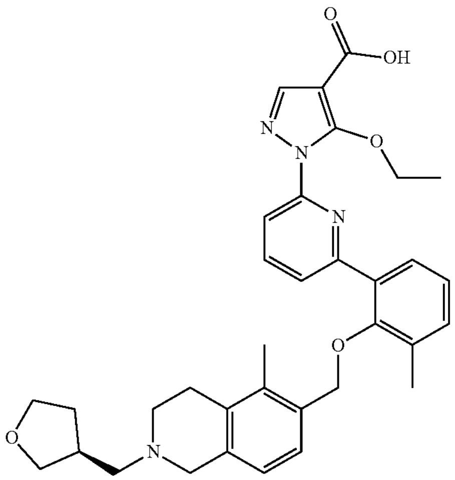 [SMILES: CCOc1c(C(=O)O)cnn1-c1cccc(-c2cccc(C)c2OCc2ccc3c(c2C)CCN(C[C@@H]2CCOC2)C3)n1] |
| 190 | 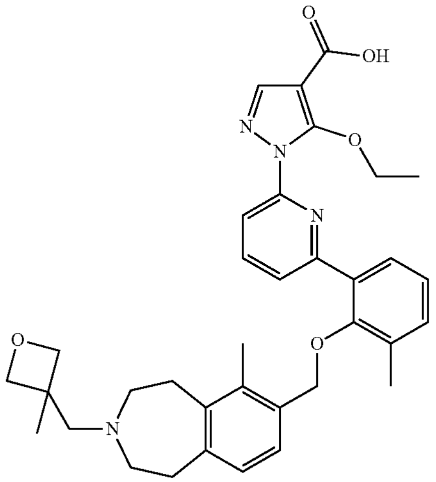 [SMILES: CCOc1c(C(=O)O)cnn1-c1cccc(-c2cccc(C)c2OCc2ccc3c(c2C)CCN(CC2(C)COC2)CC3)n1] |

TABLE 1-continued
| Cpd No. | Structure |
|---|---|
| 191 | 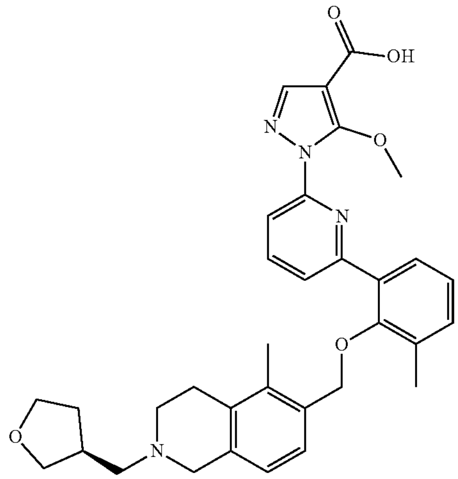 [SMILES: COc1c(C(=O)O)cnn1-c1cccc(-c2cccc(C)c2OCc2ccc3c(c2C)CCN(C[C@@H]2CCOC2)C3)n1] |
| 192 | 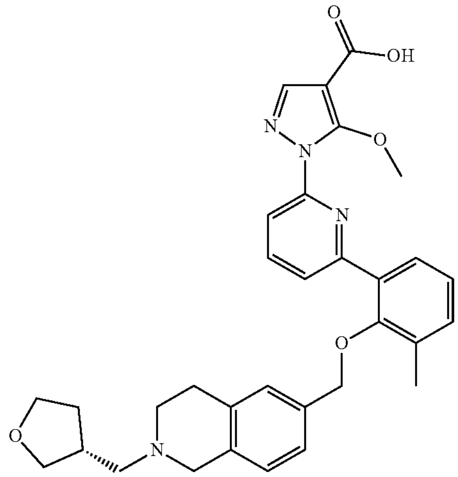 [SMILES: COc1c(C(=O)O)cnn1-c1cccc(-c2cccc(C)c2OCc2ccc3c(c2)CCN(C[C@H]2CCOC2)C3)n1] |
| 193 | 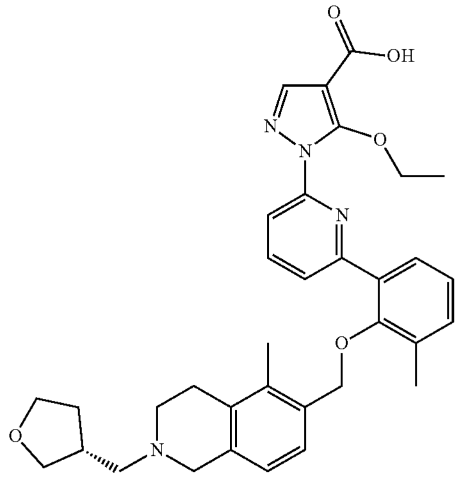 [SMILES: CCOc1c(C(=O)O)cnn1-c1cccc(-c2cccc(C)c2OCc2ccc3c(c2C)CCN(C[C@H]2CCOC2)C3)n1] |
TABLE 1-continued
| Cpd No. | Structure |
|---|---|
| 194 | 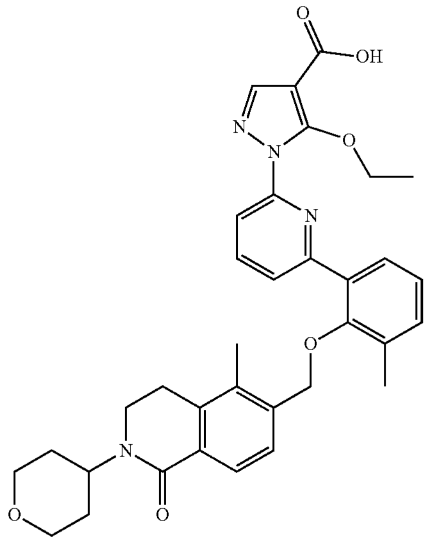 [SMILES: CCOc1c(C(=O)O)cnn1-c1cccc(-c2cccc(C)c2OCc2ccc3c(c2C)CCN(C2CCOCC2)C3=O)n1] |
| 195 | 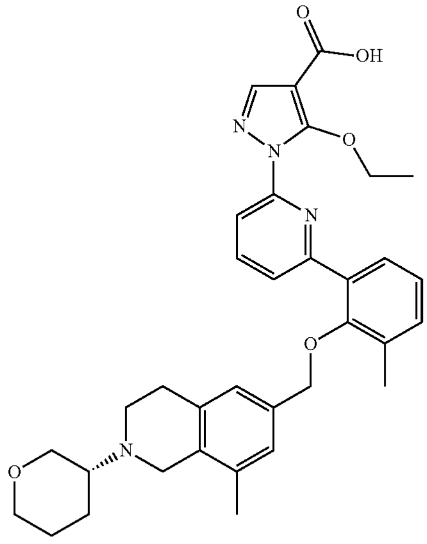 [SMILES: CCOc1c(C(=O)O)cnn1-c1cccc(-c2cccc(C)c2OCc2cc(C)c3c(c2)CCN([C@@H]2CCCOC2)C3)n1] |
| 196 | 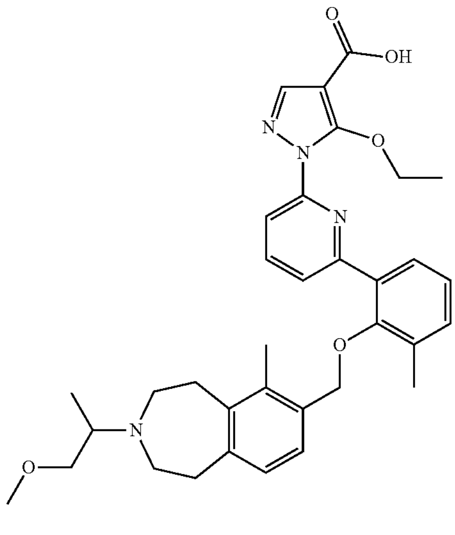 [SMILES: CCOc1c(C(=O)O)cnn1-c1cccc(-c2cccc(C)c2OCc2ccc3c(c2C)CCN(C(C)COC)CC3)n1] |

TABLE 1-continued
| Cpd No. | Structure |
| --- | --- |
| 197 | 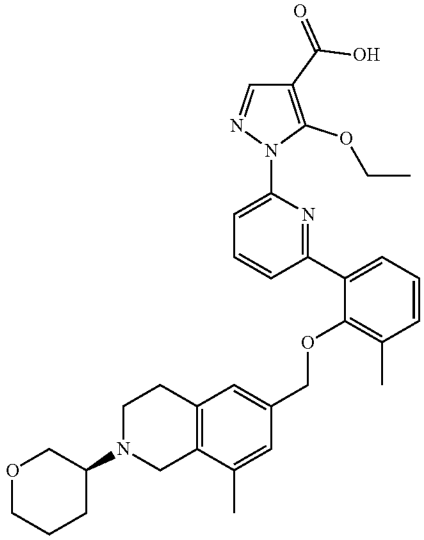 [SMILES: CCOc1c(C(=O)O)cnn1-c1cccc(-c2cccc(C)c2OCc2cc(C)c3c(c2)CCN([C@H]2CCCOC2)C3)n1] |
| 198 | 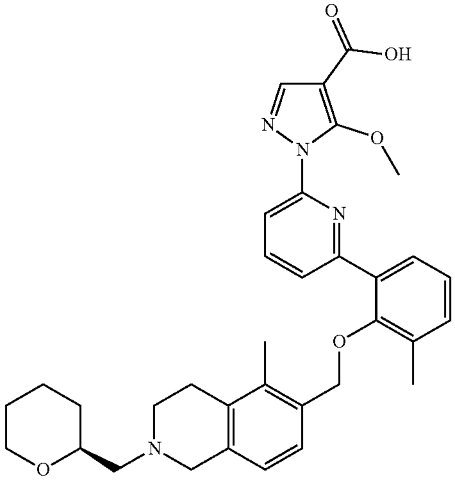 [SMILES: COc1c(C(=O)O)cnn1-c1cccc(-c2cccc(C)c2OCc2ccc3c(c2C)CCN(C[C@@H]2CCCCO2)C3)n1] |
| 199 | 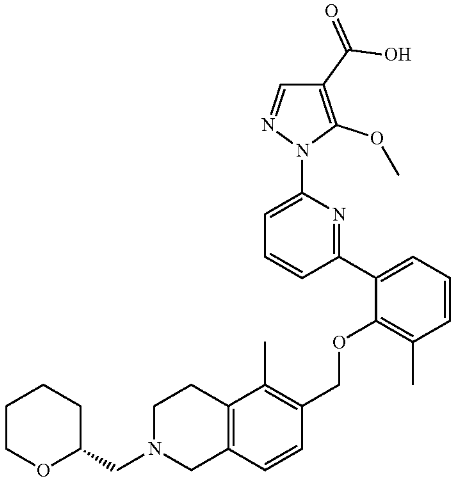 [SMILES: COc1c(C(=O)O)cnn1-c1cccc(-c2cccc(C)c2OCc2ccc3c(c2C)CCN(C[C@H]2CCCCO2)C3)n1] |
TABLE 1-continued
| Cpd No. | Structure |
| --- | --- |
| 200 | 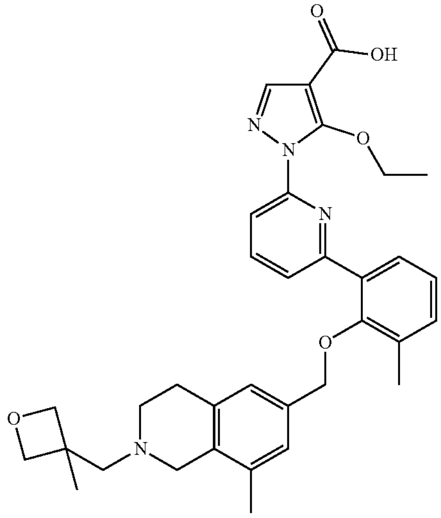 [SMILES: CCOc1c(C(=O)O)cnn1-c1cccc(-c2cccc(C)c2OCc2cc(C)c3c(c2)CCN(CC2(C)COC2)C3)n1] |
| 201 | 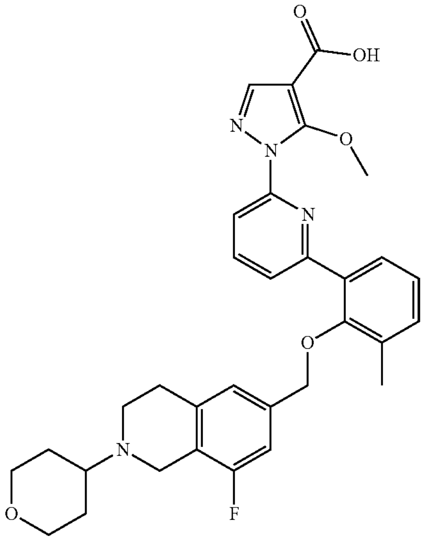 [SMILES: COc1c(C(=O)O)cnn1-c1cccc(-c2cccc(C)c2OCc2cc(F)c3c(c2)CCN(C2CCOCC2)C3)n1] |
| 202 | 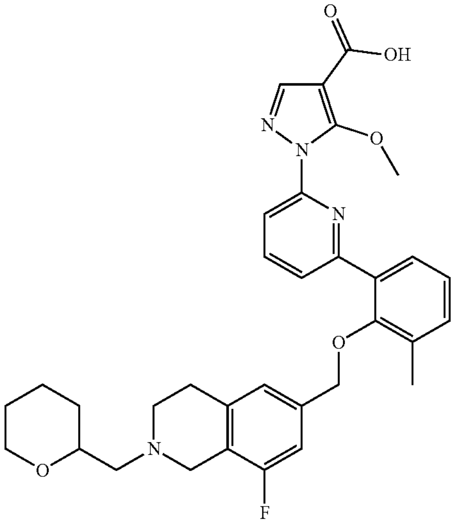 |

TABLE 1-continued
| Cpd No. | Structure |
|---|---|
| 203 | 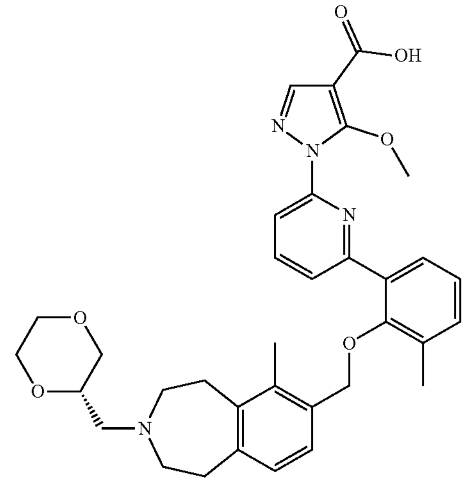 [SMILES: COc1c(C(=O)O)cnn1-c1cccc(-c2cccc(C)c2OCc2ccc3c(c2C)CCN(C[C@H]2COCCO2)CC3)n1] |
| 204 | 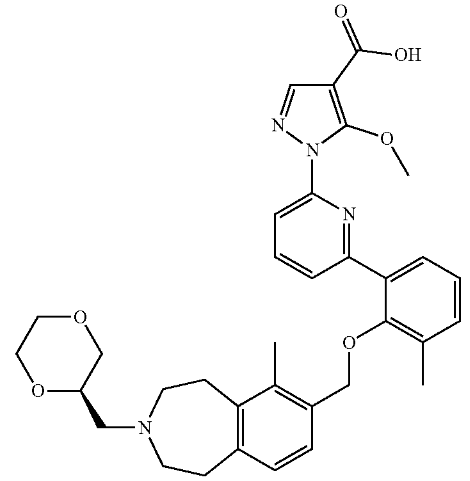 [SMILES: COc1c(C(=O)O)cnn1-c1cccc(-c2cccc(C)c2OCc2ccc3c(c2C)CCN(C[C@@H]2COCCO2)CC3)n1] |
| 205 | 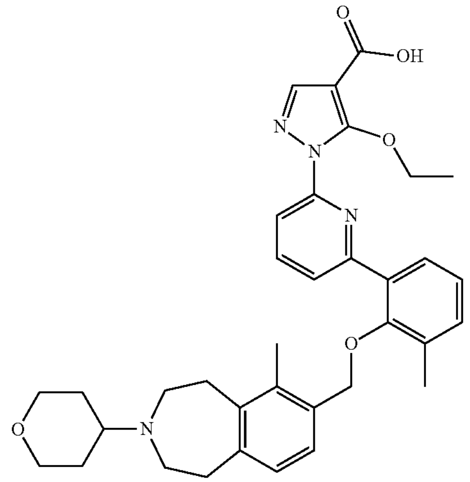 [SMILES: CCOc1c(C(=O)O)cnn1-c1cccc(-c2cccc(C)c2OCc2ccc3c(c2C)CCN(C2CCOCC2)CC3)n1] |
TABLE 1-continued
| Cpd No. | Structure |
|---|---|
| 206 | 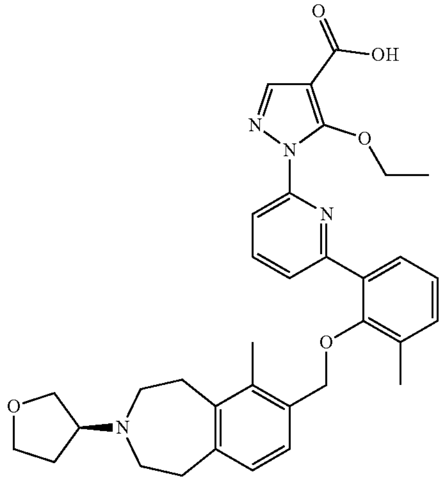 [SMILES: CCOc1c(C(=O)O)cnn1-c1cccc(-c2cccc(C)c2OCc2ccc3c(c2C)CCN([C@H]2CCOC2)CC3)n1] |
| 207 | 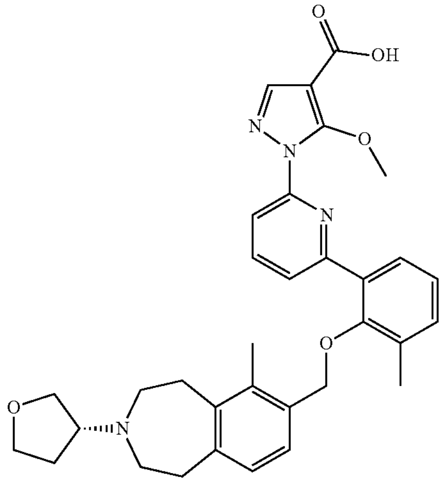 [SMILES: COc1c(C(=O)O)cnn1-c1cccc(-c2cccc(C)c2OCc2ccc3c(c2C)CCN([C@@H]2CCOC2)CC3)n1] |
| 208 | 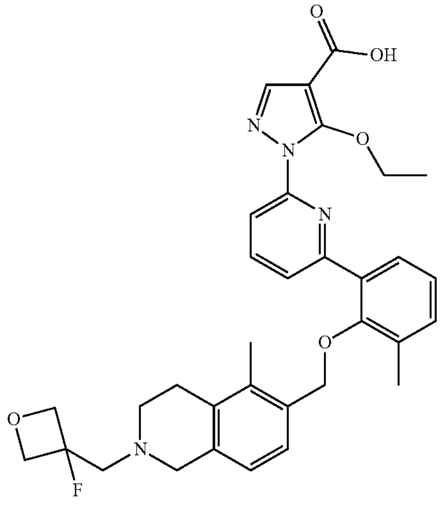 [SMILES: CCOc1c(C(=O)O)cnn1-c1cccc(-c2cccc(C)c2OCc2ccc3c(c2C)CCN(CC2(F)COC2)C3)n1] |

TABLE 1-continued
| Cpd No. | Structure |
|---|---|
| 209 | 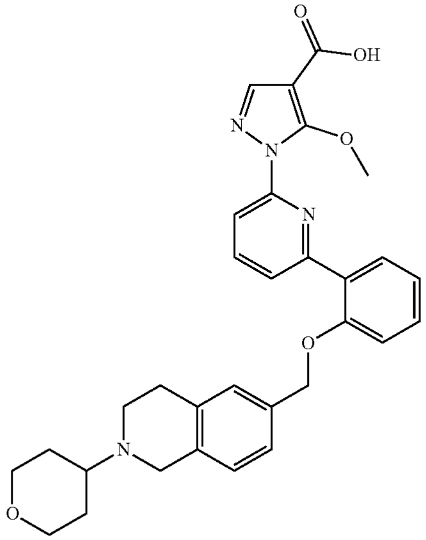 [SMILES: COc1c(C(=O)O)cnn1-c1cccc(-c2ccccc2OCc2ccc3c(c2)CCN(C2CCOCC2)C3)n1] |
| 210 | 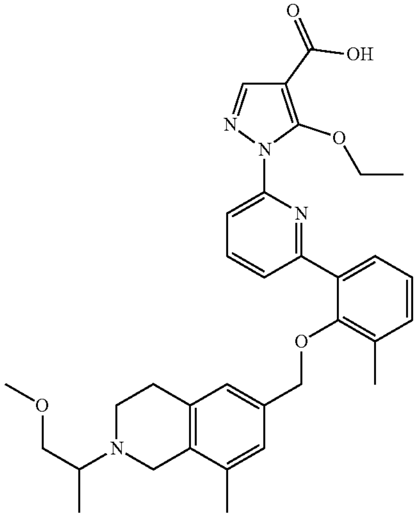 [SMILES: CCOc1c(C(=O)O)cnn1-c1cccc(-c2cccc(C)c2OCc2cc(C)c3c(c2)CCN(C(C)COC)C3)n1] |
| 211 | 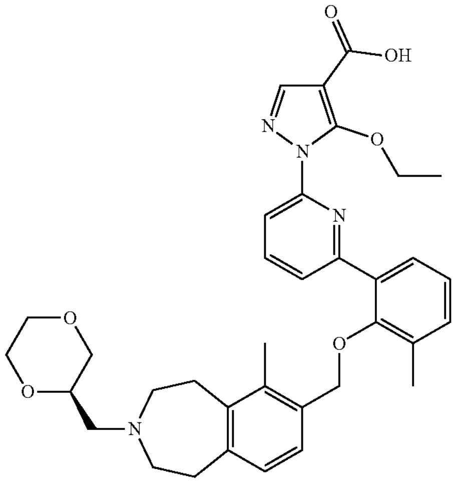 [SMILES: CCOc1c(C(=O)O)cnn1-c1cccc(-c2cccc(C)c2OCc2ccc3c(c2C)CCN(C[C@@H]2COCCO2)CC3)n1] |
TABLE 1-continued
| Cpd No. | Structure |
|---|---|
| 212 | 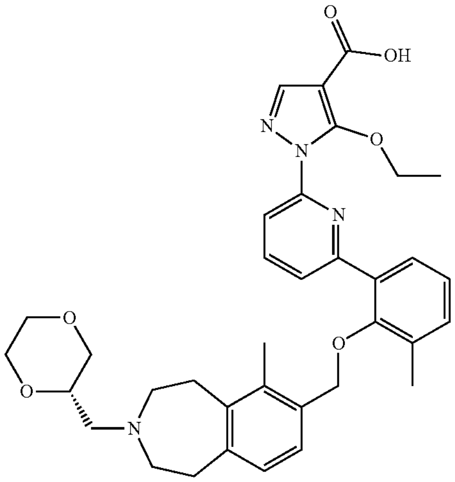 [SMILES: CCOc1c(C(=O)O)cnn1-c1cccc(-c2cccc(C)c2OCc2ccc3c(c2C)CCN(C[C@H]2COCCO2)CC3)n1] |
| 213 | 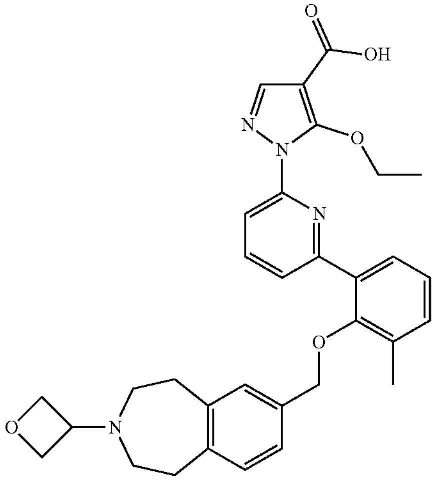 [SMILES: CCOc1c(C(=O)O)cnn1-c1cccc(-c2cccc(C)c2OCc2ccc3c(c2)CCN(C2COC2)CC3)n1] |
| 214 | 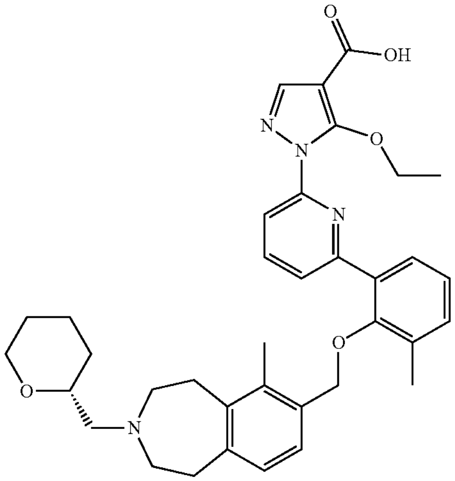 [SMILES: CCOc1c(C(=O)O)cnn1-c1cccc(-c2cccc(C)c2OCc2ccc3c(c2C)CCN(C[C@H]2CCCCO2)CC3)n1] |

TABLE 1-continued
| Cpd No. | Structure |
|---|---|
| 215 | 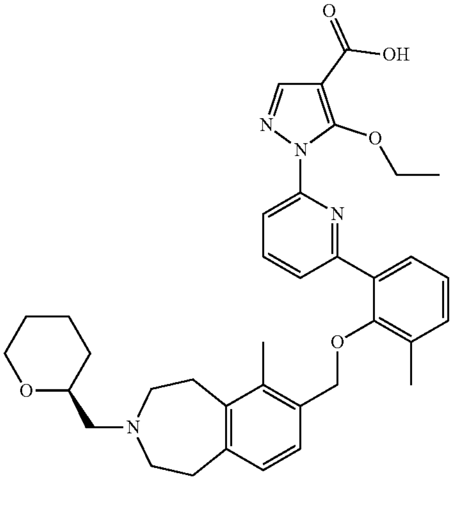 [SMILES: CCOc1c(C(=O)O)cnn1-c1cccc(-c2cccc(C)c2OCc2ccc3c(c2C)CCN(C[C@@H]2CCCCO2)CC3)n1] |
| 216 | 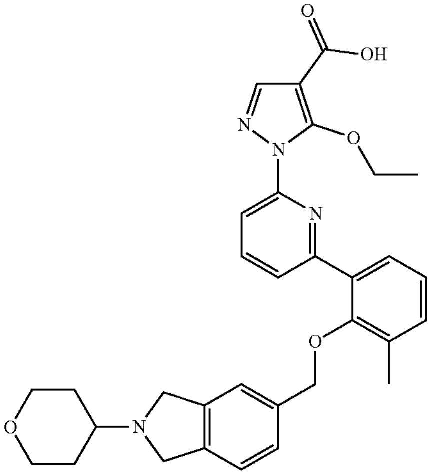 [SMILES: CCOc1c(C(=O)O)cnn1-c1cccc(-c2cccc(C)c2OCc2ccc3c(c2)CN(C2CCOCC2)C3)n1] |
| 217 | 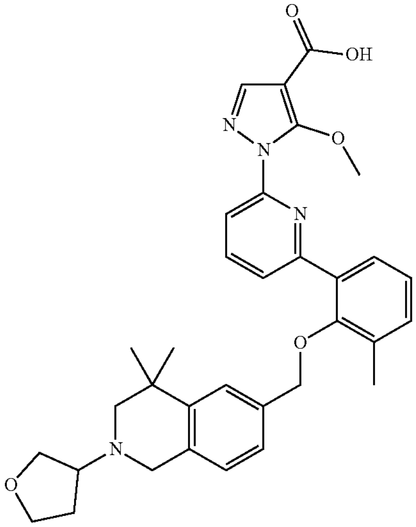 [SMILES: COc1c(C(=O)O)cnn1-c1cccc(-c2cccc(C)c2OCc2ccc3c(c2)C(C)(C)CN(C2CCOC2)C3)n1] |
| 218 | 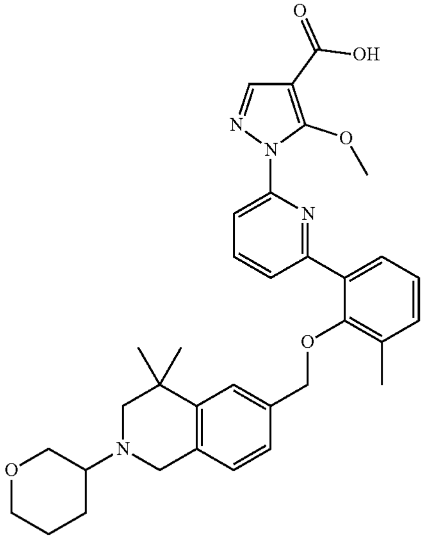 [SMILES: COc1c(C(=O)O)cnn1-c1cccc(-c2cccc(C)c2OCc2ccc3c(c2)C(C)(C)CN(C2CCCOC2)C3)n1] |
| 219 | 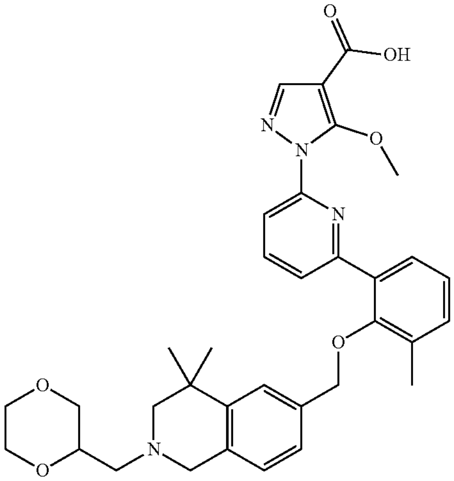 [SMILES: COc1c(C(=O)O)cnn1-c1cccc(-c2cccc(C)c2OCc2ccc3c(c2)C(C)(C)CN(CC2COCCO2)C3)n1] |
| 220 | 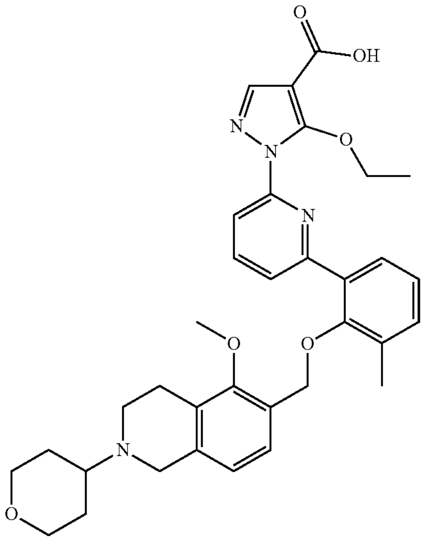 [SMILES: CCOc1c(C(=O)O)cnn1-c1cccc(-c2cccc(C)c2OCc2ccc3c(c2OC)CCN(C2CCOCC2)C3)n1] |

TABLE 1-continued
| Cpd No. | Structure |
| --- | --- |
| 221 | 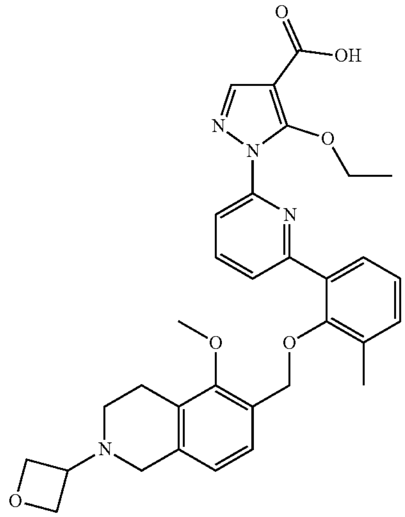 [SMILES: CCOc1c(C(=O)O)cnn1-c1cccc(-c2cccc(C)c2OCc2ccc3c(c2OC)CCN(C2COC2)C3)n1] |
| 222 | 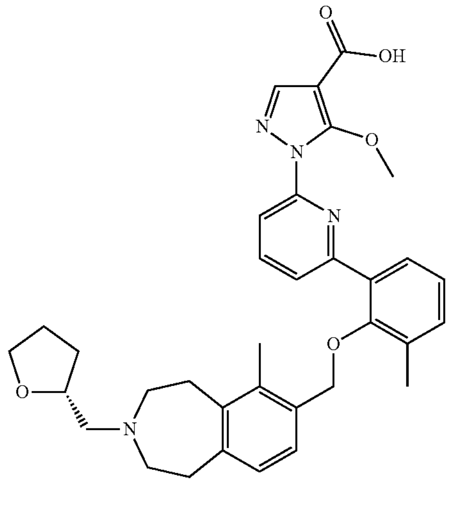 [SMILES: COc1c(C(=O)O)cnn1-c1cccc(-c2cccc(C)c2OCc2ccc3c(c2C)CCN(C[C@H]2CCCO2)CC3)n1] |
| 223 | 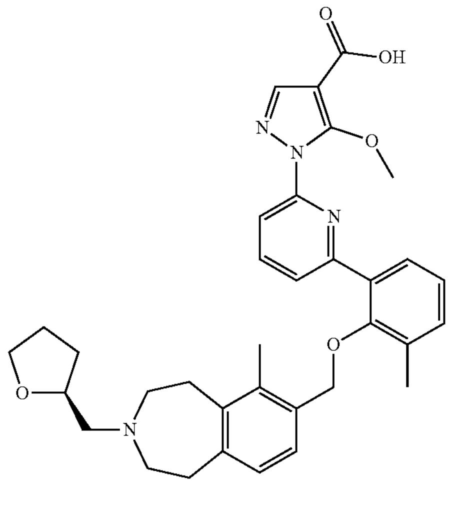 [SMILES: COc1c(C(=O)O)cnn1-c1cccc(-c2cccc(C)c2OCc2ccc3c(c2C)CCN(C[C@@H]2CCCO2)CC3)n1] |
TABLE 1-continued
| Cpd No. | Structure |
| --- | --- |
| 224 | 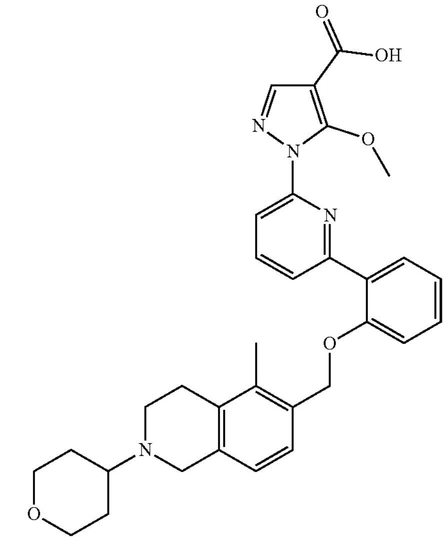 [SMILES: COc1c(C(=O)O)cnn1-c1cccc(-c2ccccc2OCc2ccc3c(c2C)CCN(C2CCOCC2)C3)n1] |
| 225 | 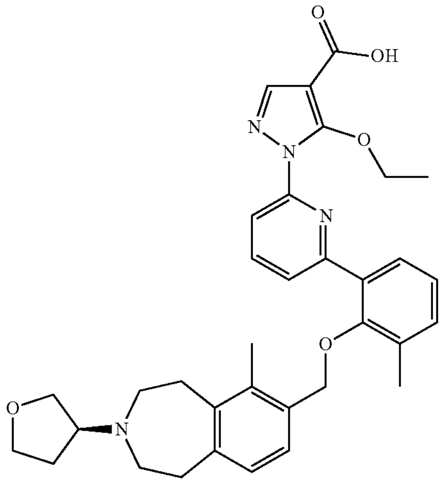 [SMILES: CCOc1c(C(=O)O)cnn1-c1cccc(-c2cccc(C)c2OCc2ccc3c(c2C)CCN([C@H]2CCOC2)CC3)n1] |
| 226 | 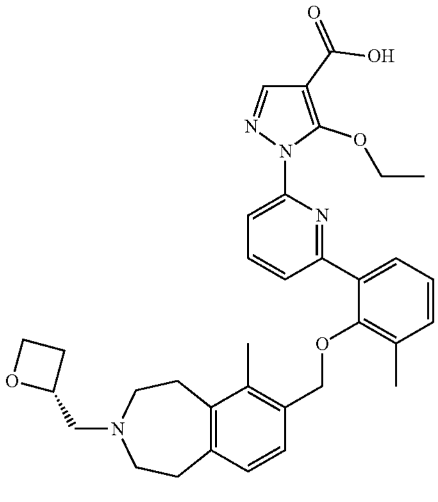 [SMILES: CCOc1c(C(=O)O)cnn1-c1cccc(-c2cccc(C)c2OCc2ccc3c(c2C)CCN(C[C@H]2CCO2)CC3)n1] |

TABLE 1-continued
| Cpd No. | Structure |
|---|---|
| 227 | 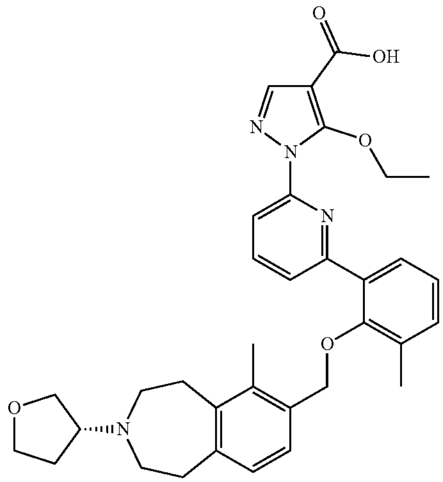 [SMILES: CCOc1c(C(=O)O)cnn1-c1cccc(-c2cccc(C)c2OCc2ccc3c(c2C)CCN([C@@H]2CCOC2)CC3)n1] |
| 228 | 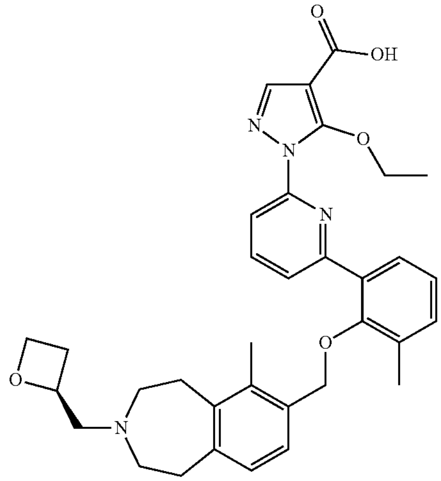 [SMILES: CCOc1c(C(=O)O)cnn1-c1cccc(-c2cccc(C)c2OCc2ccc3c(c2C)CCN(C[C@@H]2CCO2)CC3)n1] |
| 229 | 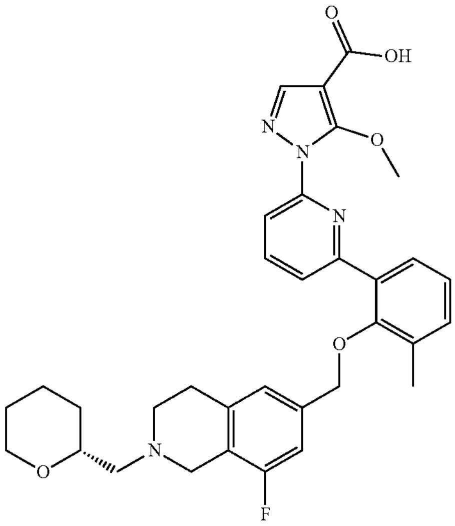 |
TABLE 1-continued
| Cpd No. | Structure |
|---|---|
| 230 | 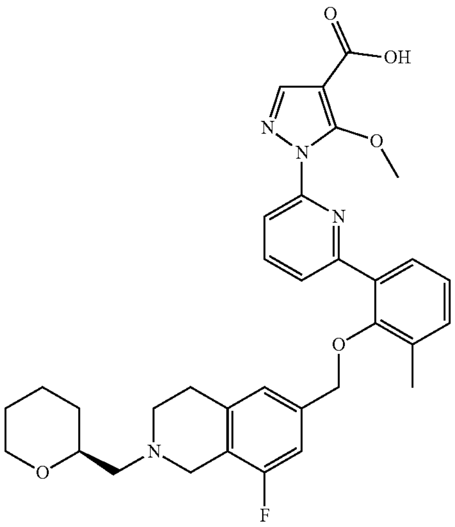 [SMILES: COc1c(C(=O)O)cnn1-c1cccc(-c2cccc(C)c2OCc2cc(F)c3c(c2)CCN(C[C@@H]2CCCCO2)C3)n1] |
| 231 | 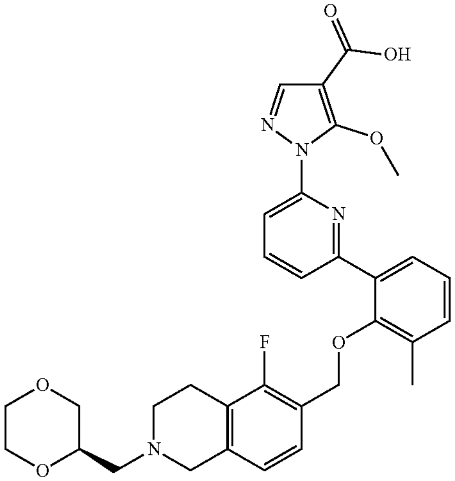 [SMILES: COc1c(C(=O)O)cnn1-c1cccc(-c2cccc(C)c2OCc2ccc3c(c2F)CCN(C[C@@H]2COCCO2)C3)n1] |
| 232 | 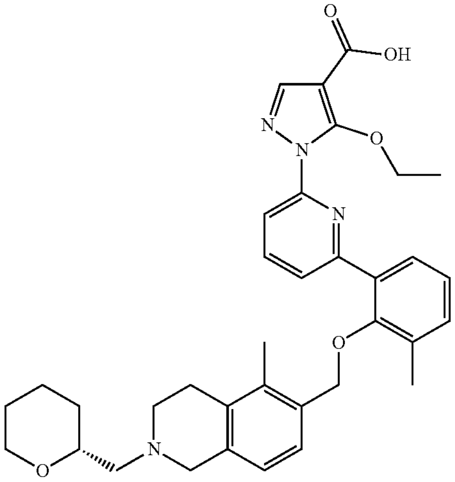 [SMILES: CCOc1c(C(=O)O)cnn1-c1cccc(-c2cccc(C)c2OCc2ccc3c(c2C)CCN(C[C@H]2CCCCO2)C3)n1] |

TABLE 1-continued
| Cpd No. | Structure |
|---|---|
| 233 | 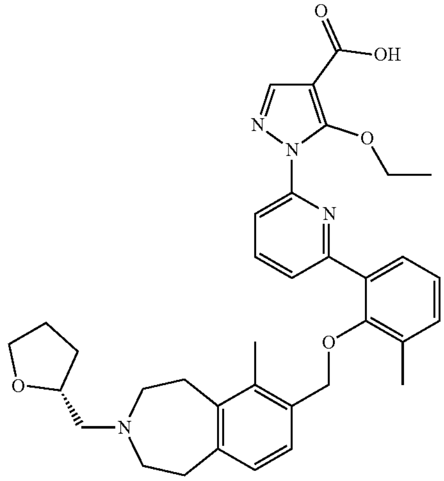 [SMILES: CCOc1c(C(=O)O)cnn1-c1cccc(-c2cccc(C)c2OCc2ccc3c(c2C)CCN(C[C@H]2CCCO2)CC3)n1] |
| 234 | 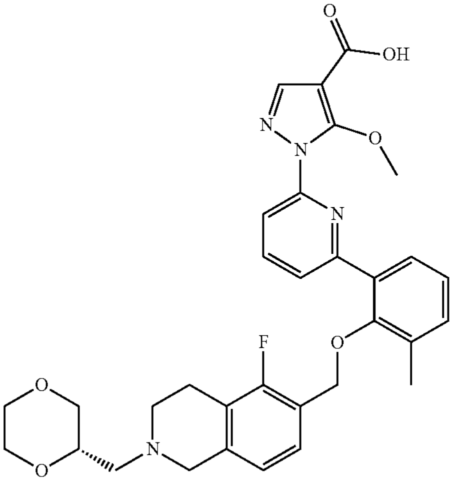 [SMILES: COc1c(C(=O)O)cnn1-c1cccc(-c2cccc(C)c2OCc2ccc3c(c2F)CCN(C[C@H]2COCCO2)C3)n1] |
| 235 | 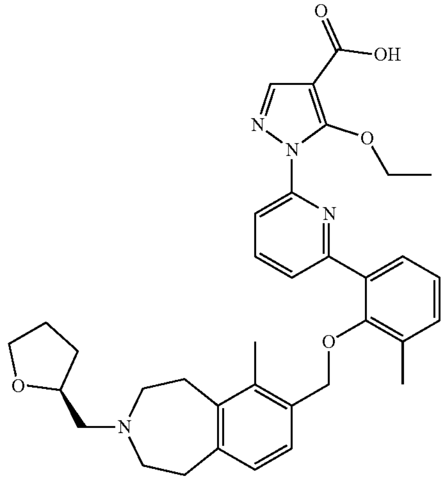 [SMILES: CCOc1c(C(=O)O)cnn1-c1cccc(-c2cccc(C)c2OCc2ccc3c(c2C)CCN(C[C@@H]2CCCO2)CC3)n1] |
TABLE 1-continued
| Cpd No. | Structure |
|---|---|
| 236 | 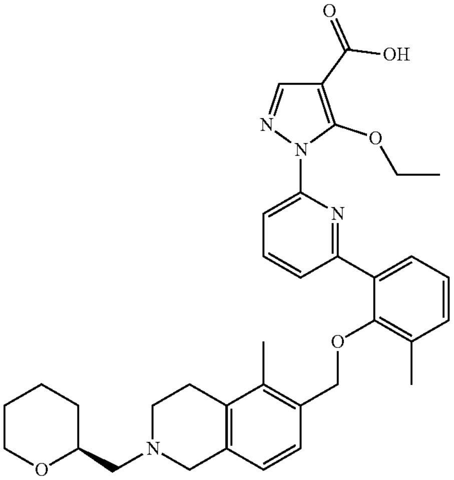 [SMILES: CCOc1c(C(=O)O)cnn1-c1cccc(-c2cccc(C)c2OCc2ccc3c(c2C)CCN(C[C@@H]2CCCCO2)C3)n1] |
| 237 | 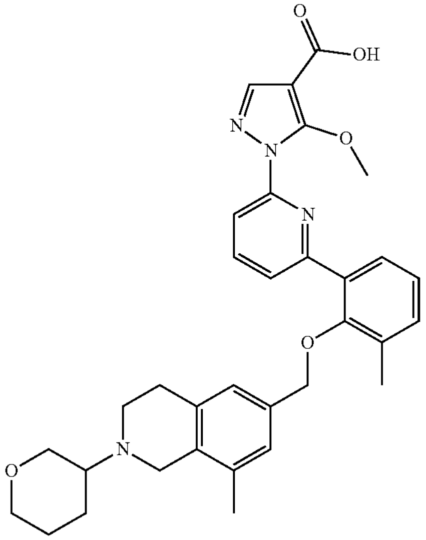 [SMILES: COc1c(C(=O)O)cnn1-c1cccc(-c2cccc(C)c2OCc2cc(C)c3c(c2)CCN(C2CCCOC2)C3)n1] |
| 238 | 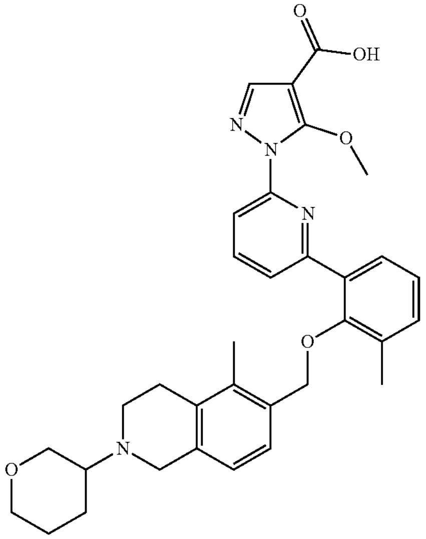 [SMILES: COc1c(C(=O)O)cnn1-c1cccc(-c2cccc(C)c2OCc2ccc3c(c2C)CCN(C2CCCOC2)C3)n1] |

TABLE 1-continued
| Cpd No. | Structure |
|---|---|
| 239 | 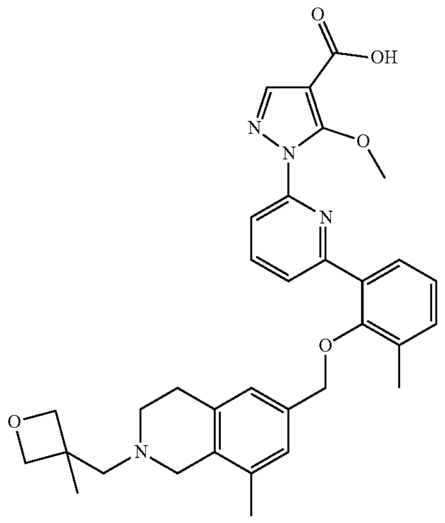 [SMILES: COc1c(C(=O)O)cnn1-c1cccc(-c2cccc(C)c2OCc2cc(C)c3c(c2)CCN(CC2(C)COC2)C3)n1] |
| 240 | 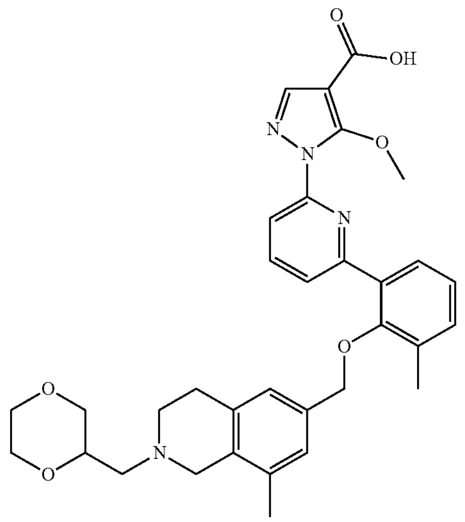 [SMILES: COc1c(C(=O)O)cnn1-c1cccc(-c2cccc(C)c2OCc2cc(C)c3c(c2)CCN(CC2COCCO2)C3)n1] |
| 241 | 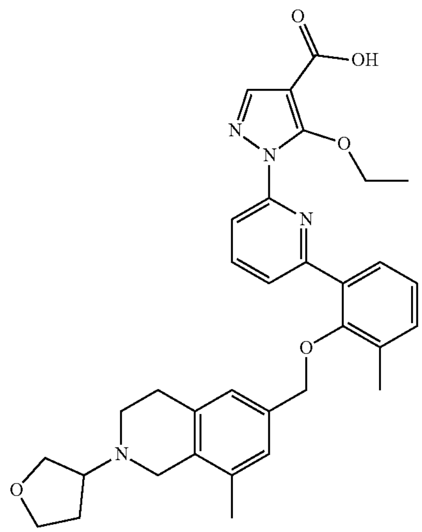 [SMILES: CCOc1c(C(=O)O)cnn1-c1cccc(-c2cccc(C)c2OCc2cc(C)c3c(c2)CCN(C2CCOC2)C3)n1] |
TABLE 1-continued
| Cpd No. | Structure |
|---|---|
| 242 | 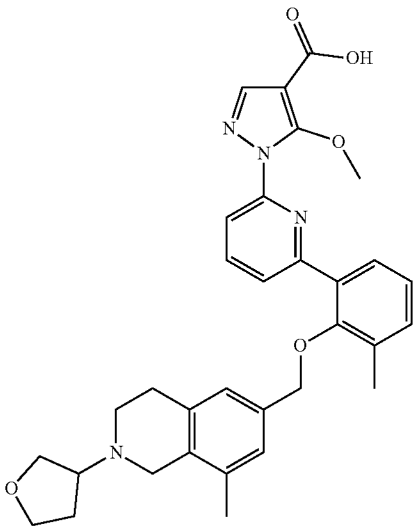 [SMILES: COc1c(C(=O)O)cnn1-c1cccc(-c2cccc(C)c2OCc2cc(C)c3c(c2)CCN(C2CCOC2)C3)n1] |
| 243 | 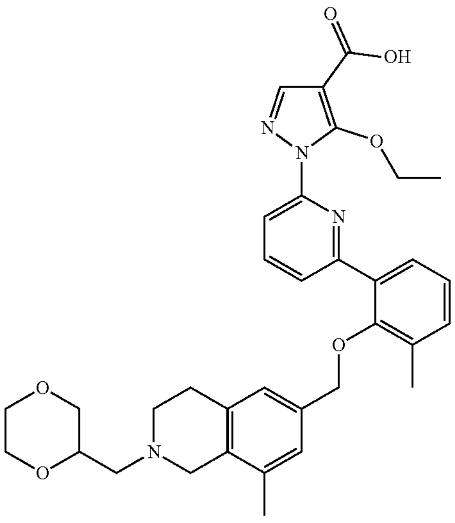 [SMILES: CCOc1c(C(=O)O)cnn1-c1cccc(-c2cccc(C)c2OCc2cc(C)c3c(c2)CCN(CC2COCCO2)C3)n1] |
| 244 | 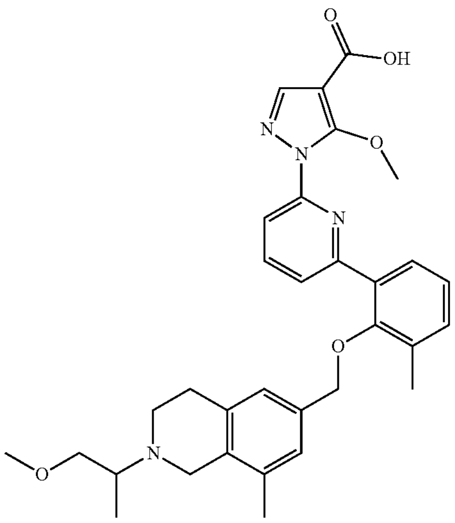 [SMILES: COCC(C)N1CCc2cc(COc3c(C)cccc3-c3cccc(-n4ncc(C(=O)O)c4OC)n3)cc(C)c2C1] |

TABLE 1-continued
| Cpd No. | Structure |
| --- | --- |
| 245 | 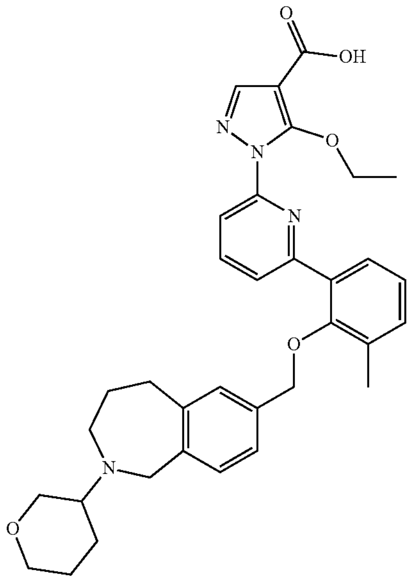 [SMILES: CCOc1c(C(=O)O)cnn1-c1cccc(-c2cccc(C)c2OCc2ccc3c(c2)CCCN(C2CCCOC2)C3)n1] |
| 246 | 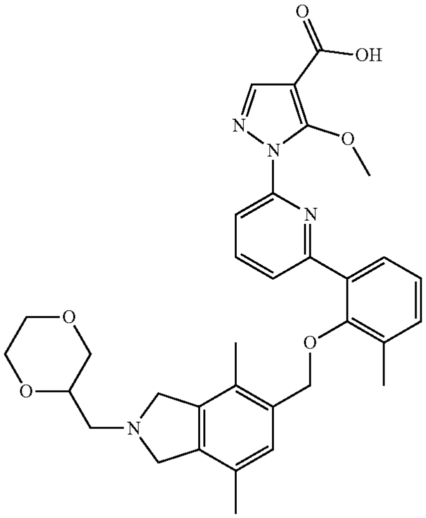 [SMILES: COc1c(C(=O)O)cnn1-c1cccc(-c2cccc(C)c2OCc2cc(C)c3c(c2C)CN(CC2COCCO2)C3)n1] |
| 247 | 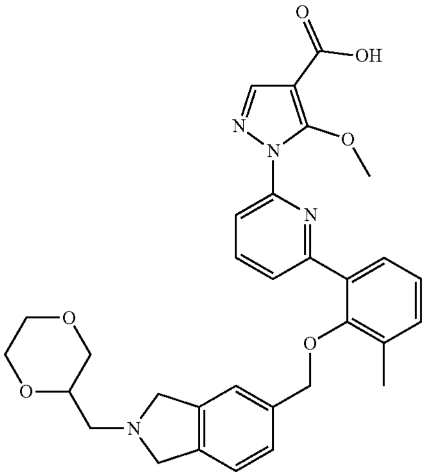 [SMILES: COc1c(C(=O)O)cnn1-c1cccc(-c2cccc(C)c2OCc2ccc3c(c2)CN(CC2COCCO2)C3)n1] |
| 248 | 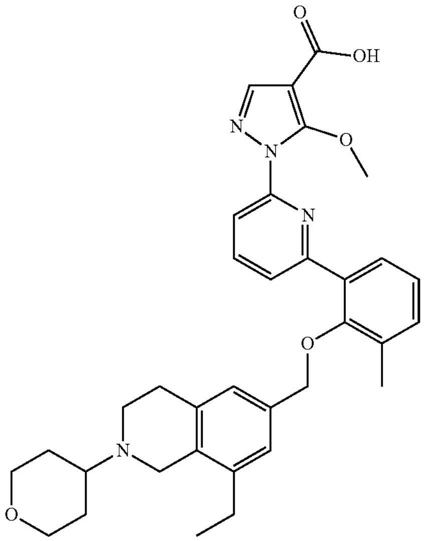 [SMILES: CCc1cc(COc2c(C)cccc2-c2cccc(-n3ncc(C(=O)O)c3OC)n2)cc2c1CN(C1CCOCC1)CC2] |
| 249 | 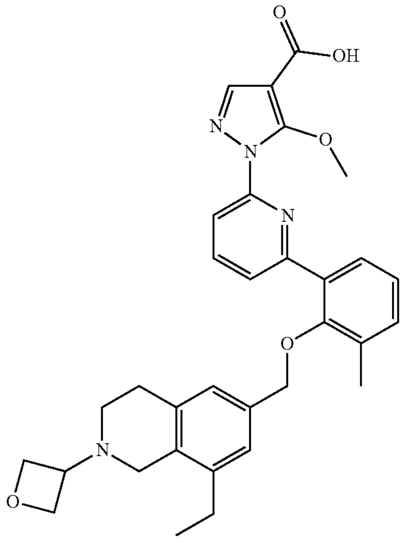 [SMILES: CCc1cc(COc2c(C)cccc2-c2cccc(-n3ncc(C(=O)O)c3OC)n2)cc2c1CN(C1COC1)CC2] |

TABLE 1-continued
| Cpd No. | Structure |
|---|---|
| 250 | 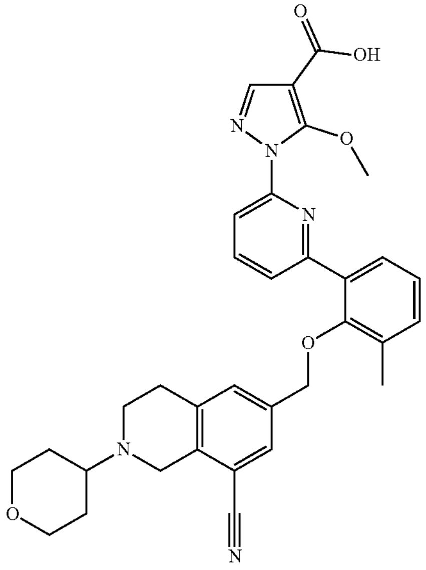 [SMILES: COc1c(C(=O)O)cnn1-c1cccc(-c2cccc(C)c2OCc2cc(C#N)c3c(c2)CCN(C2CCOCC2)C3)n1] |
| 251 | 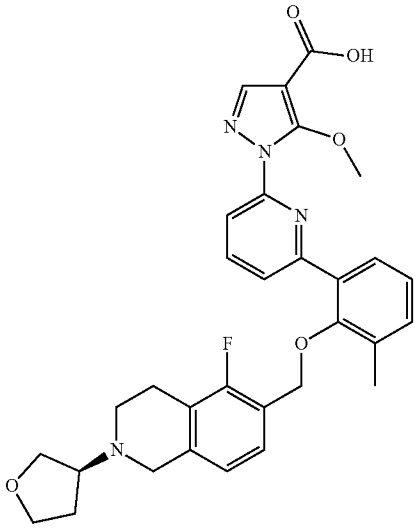 [SMILES: COc1c(C(=O)O)cnn1-c1cccc(-c2cccc(C)c2OCc2ccc3c(c2F)CCN([C@H]2CCOC2)C3)n1] |
| 252 | 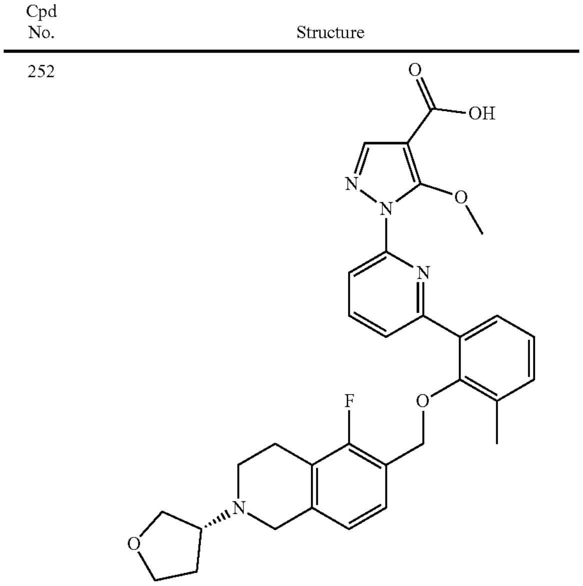 |
| 253 | 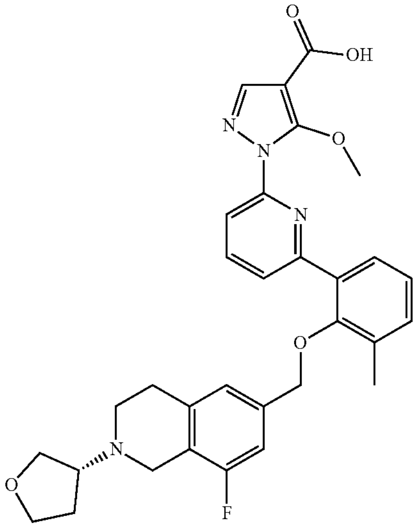 [SMILES: COc1c(C(=O)O)cnn1-c1cccc(-c2cccc(C)c2OCc2cc(F)c3c(c2)CCN([C@@H]2CCOC2)C3)n1] |
| 254 | 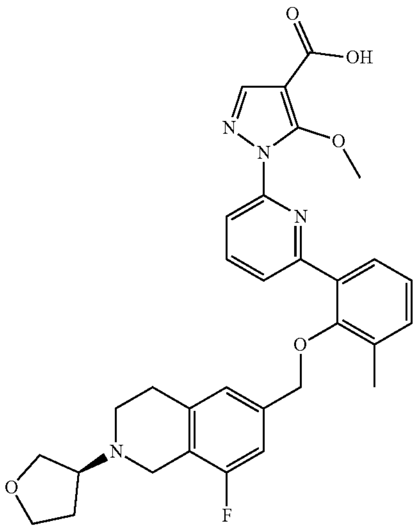 [SMILES: COc1c(C(=O)O)cnn1-c1cccc(-c2cccc(C)c2OCc2cc(F)c3c(c2)CCN([C@H]2CCOC2)C3)n1] |

TABLE 1-continued

| Cpd No. | Structure |
|---|---|
| 255 | 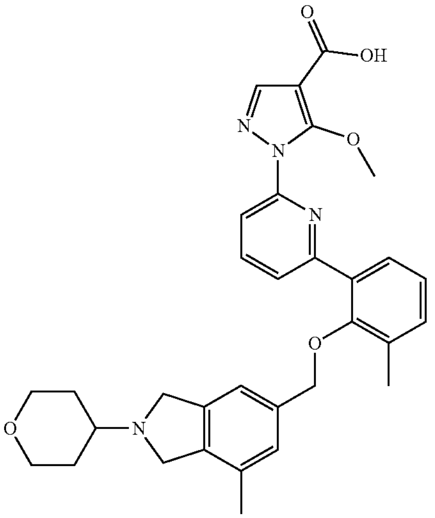 [SMILES: COc1c(C(=O)O)cnn1-c1cccc(-c2cccc(C)c2OCc2cc(C)c3c(c2)CN(C2CCOCC2)C3)n1] |
| 256 | 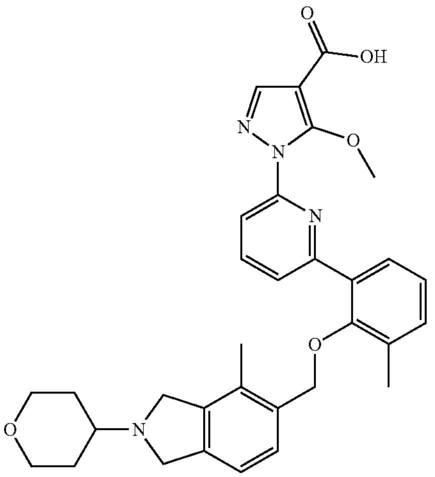 [SMILES: COc1c(C(=O)O)cnn1-c1cccc(-c2cccc(C)c2OCc2ccc3c(c2C)CN(C2CCOCC2)C3)n1] |
| 257 | 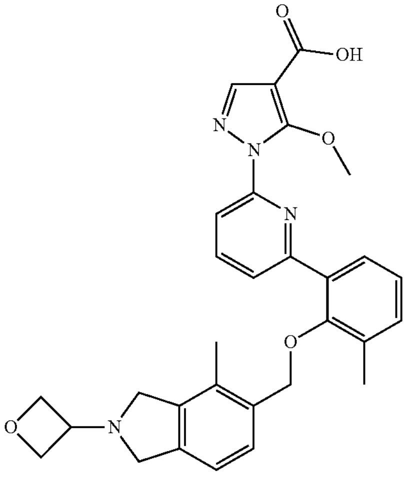 [SMILES: COc1c(C(=O)O)cnn1-c1cccc(-c2cccc(C)c2OCc2ccc3c(c2C)CN(C2COC2)C3)n1] |

TABLE 1-continued

| Cpd No. | Structure |
|---|---|
| 258 | 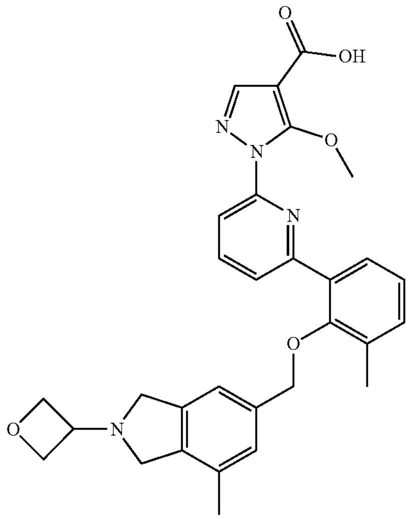 [SMILES: COc1c(C(=O)O)cnn1-c1cccc(-c2cccc(C)c2OCc2cc(C)c3c(c2)CN(C2COC2)C3)n1] |

In one embodiment, the sGC activator used in the methods of the invention is selected from any of compounds depicted in Table 1 above, and the pharmaceutically acceptable salts thereof.

In another embodiment, the sGC activator used in the methods of the invention is selected from the group consisting of compound number 1, 2, 3, 4, 5, 7, 8, 9, 12, 15, 16, 18, 21, 27, 28, 30, 31, 35, 36, 39, 41, 42, 44, 45, 46, 47, 48, 57, 59, 62, 68, 77, 78, 79, 80, 82, 83, 84, 85, 86, 88, 92, 93, and 94, and the pharmaceutically acceptable salts thereof, as such compounds are depicted in Table 1.

In another embodiment, the sGC activator used in the methods of the invention is selected from the group consisting of compound number 95, 97, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 136, 137, 139, 140, 141, 142, 145, 146, 152, 153, 154, 155, 157, 158, 159, 161, 162, 163, 164, 165, 166, 167, 169, 170, 171, 172, 173, 174, 175, 176, 177, 178, 179, 180, 181, 184, 185, 186, 187, 188, 189, 191, 193, 194, 195, 196, 197, 198, 199, 201, 202, 203, 204, 205, 206, 207, 208, 210, 211, 212, 213, 214, 215, 216, 220, 222, 223, 224, 225, 227, 229, 230, 231, 232, 233, 234, 235, 236, 237, 238, 239, 240, 241, 242, 243, 244, 246, 247, 248, 249, 250, 251, 252, 253, 254, 255, 256, 257, and the pharmaceutically acceptable salts thereof, as such compounds are depicted in Table 1.

In one embodiment, the sGC activator used in the methods of the invention is compound number 114.

BRIEF DESCRIPTION OF THE SEVERAL VIEW OF THE DRAWINGS

In the figures, "Ex 114" refers to Compound 114; "Ninte" or "Nin" refer to nintedanib; "bleo" refers to bleomycin; and "EX637" or "EX 76637" refers to riociguat.

Figure 3A:
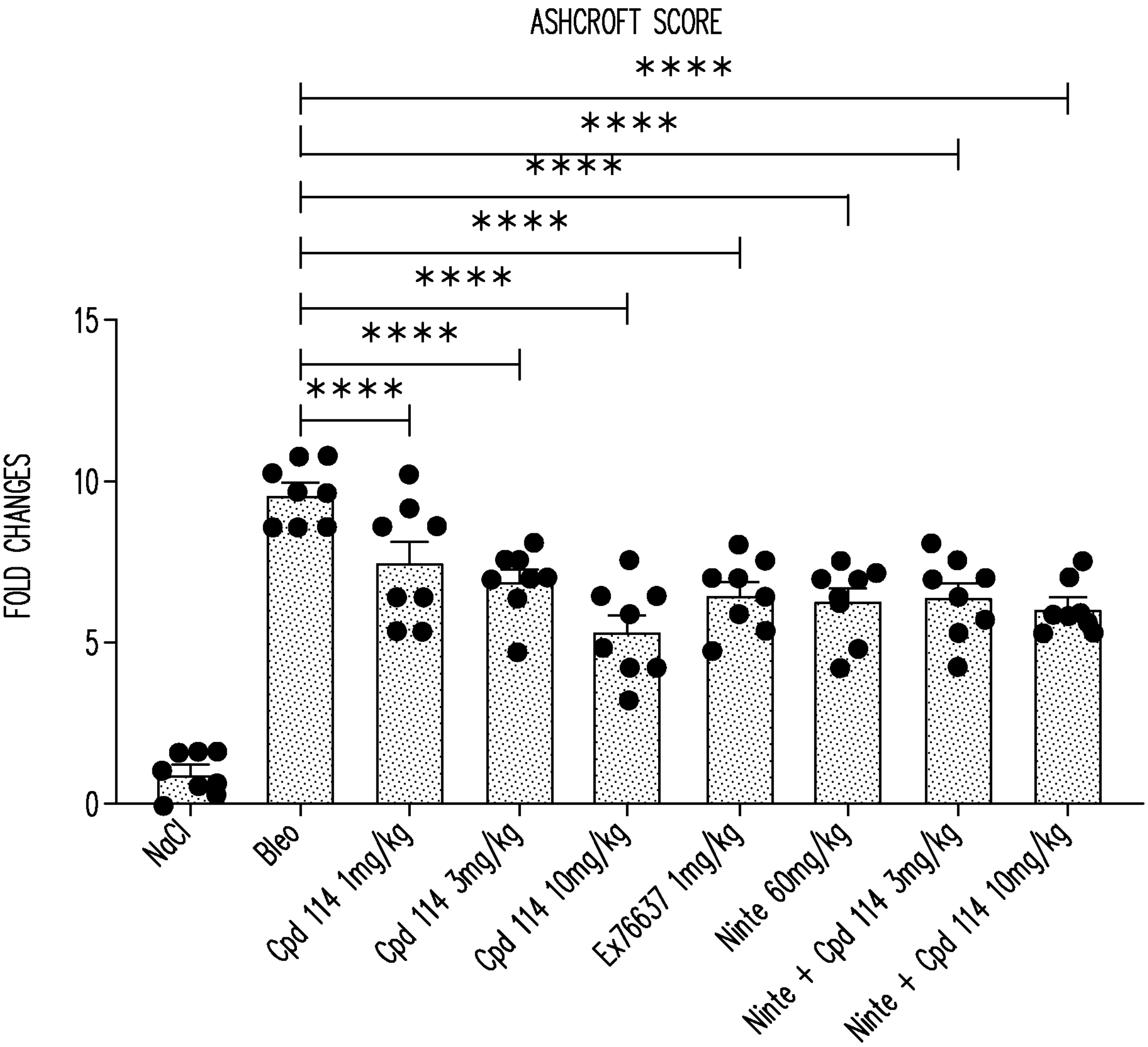
Figure 3B:
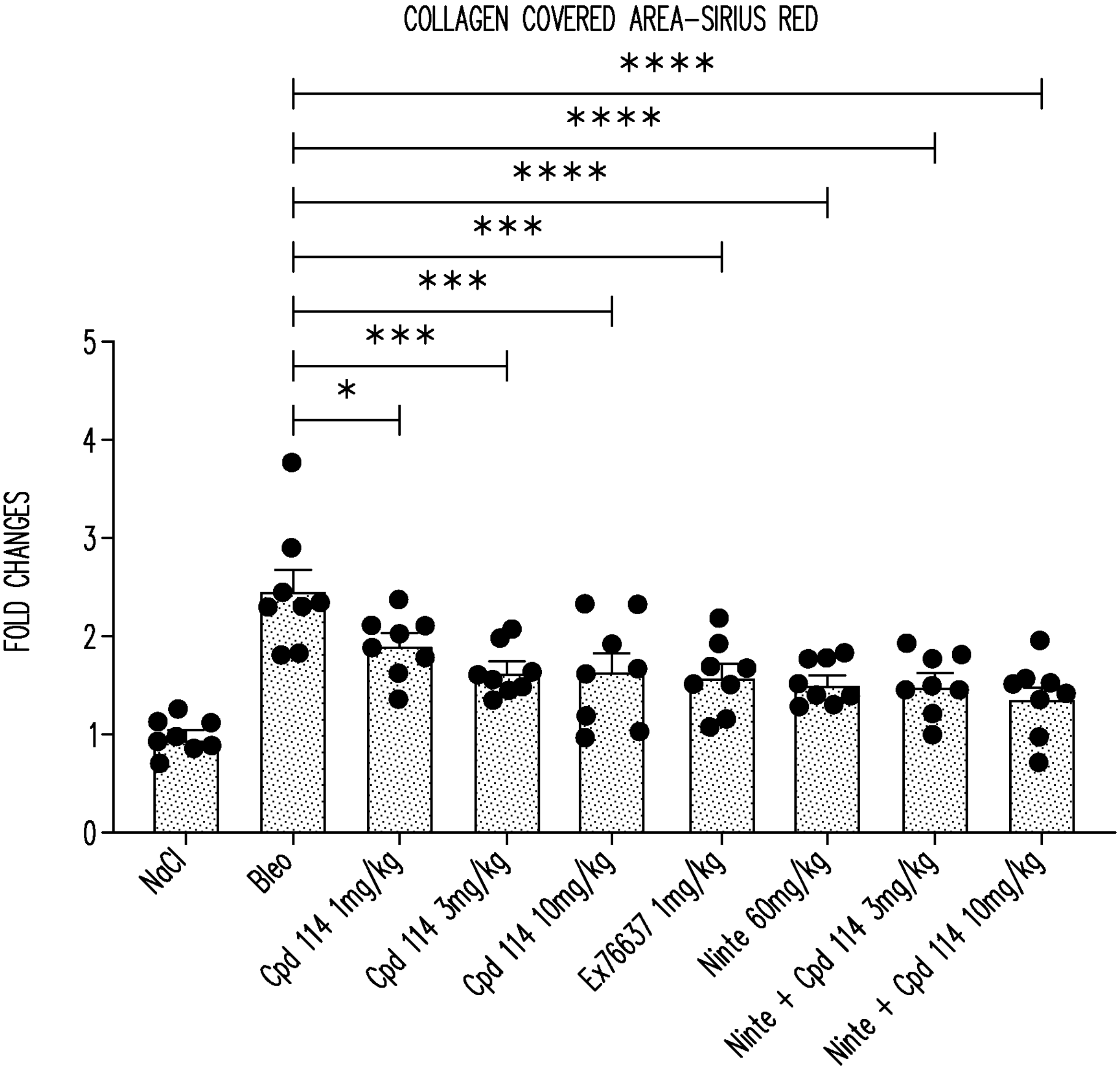
Figure 3C:
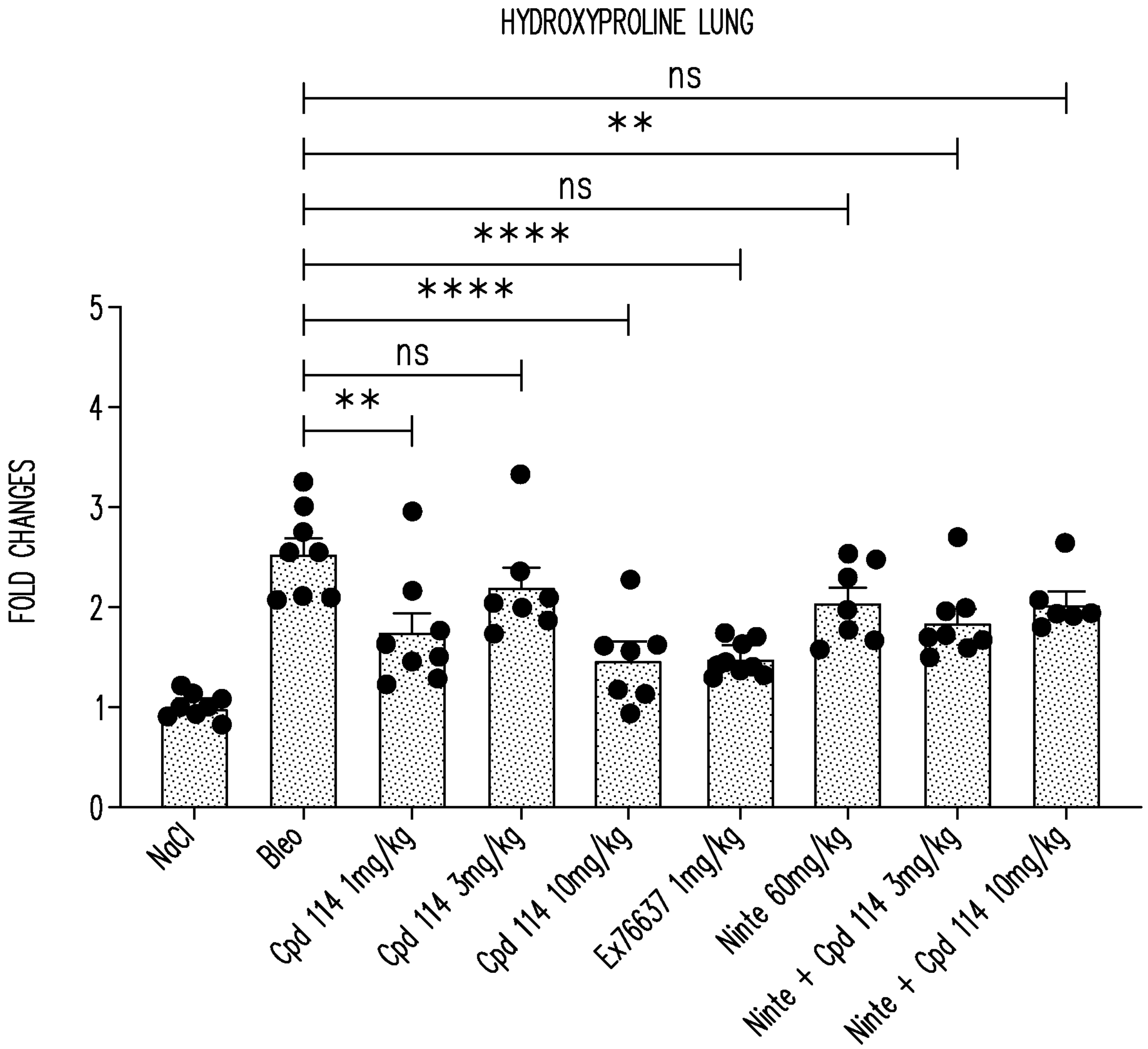

FIGS. 3A-3C show the effect of bleomycin-induced pulmonary fibrosis on Ashcroft scores (FIG. 3A), the collagen-covered area (FIG. 3B) and the hydroxyproline content (FIG. 3C). P-values of less than 0.05 are considered as statistically significant; p-values are expressed as follows: 0.05>p>0.01 as *; 0.01>p>0.001 as , 0.001>p>0.0001 as * and p<0.0001 as ****; non-significant differences are marked as ns.

Figure 4:
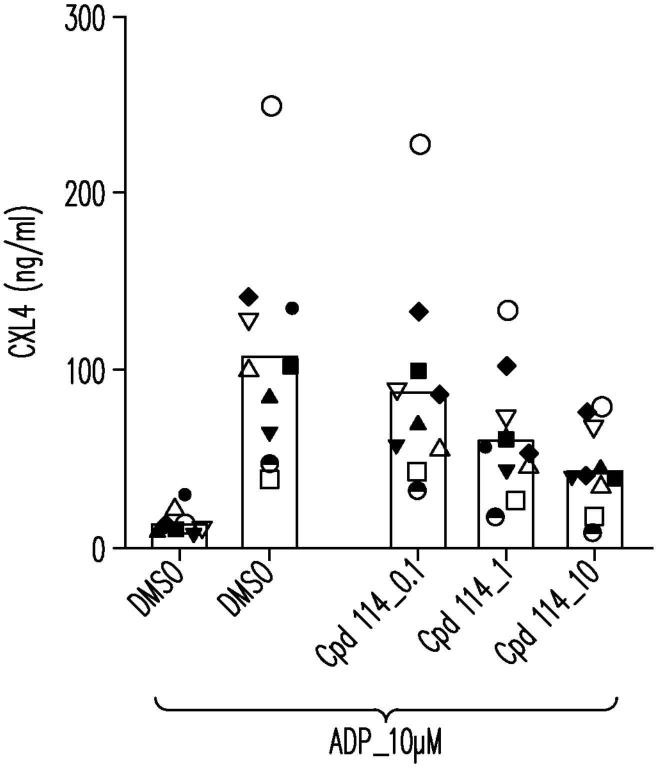

FIG. 4 shows that ADP-induced CXCL4 secretion is reduced by Compound 114 (Ex 114).

Figure 5:
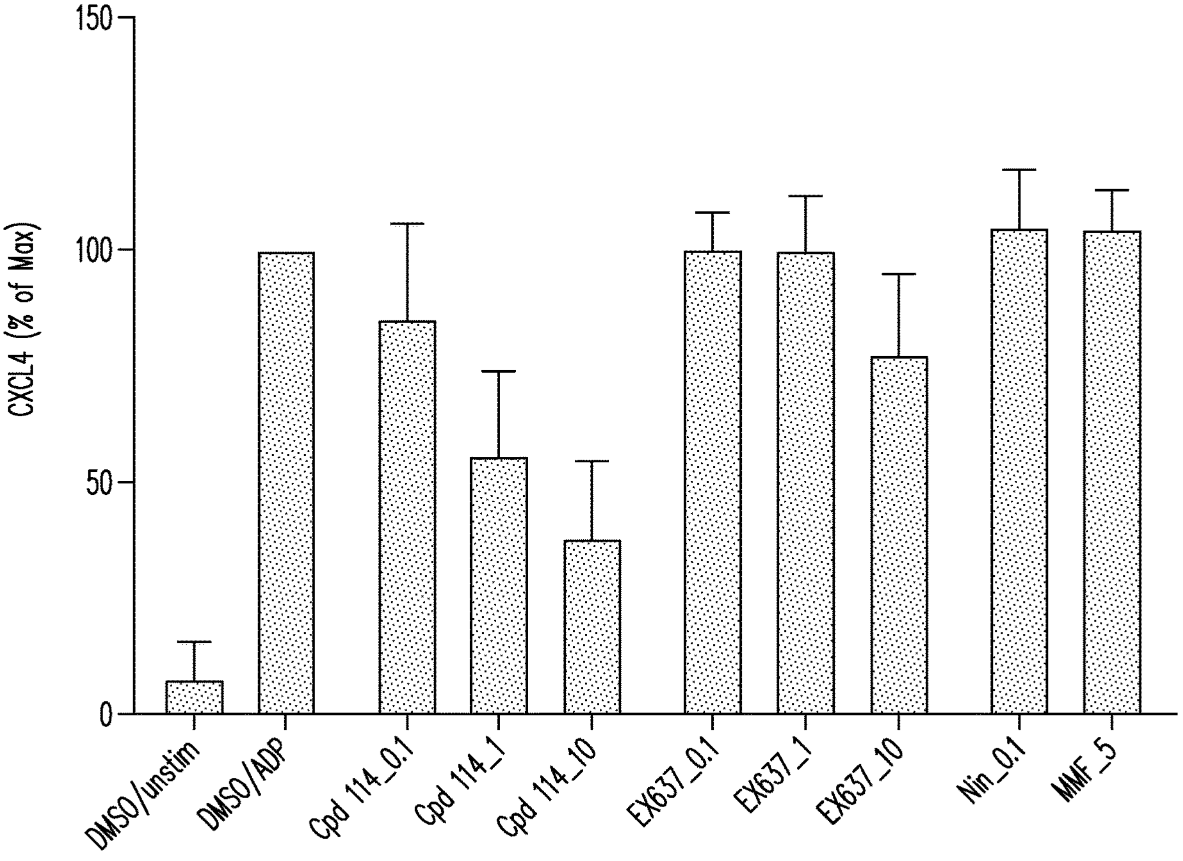

FIG. 5 shows that sGC activator Compound 114 (Ex 114) significantly reduced ADP-induced CXCL4 production in a dose-dependent manner. FIG. 5 also shows that Compound 114 is more potent/more efficacious than nintedanib (Ni, mycophenolate (MMF) and riociguat (EX637).

Figure 6:
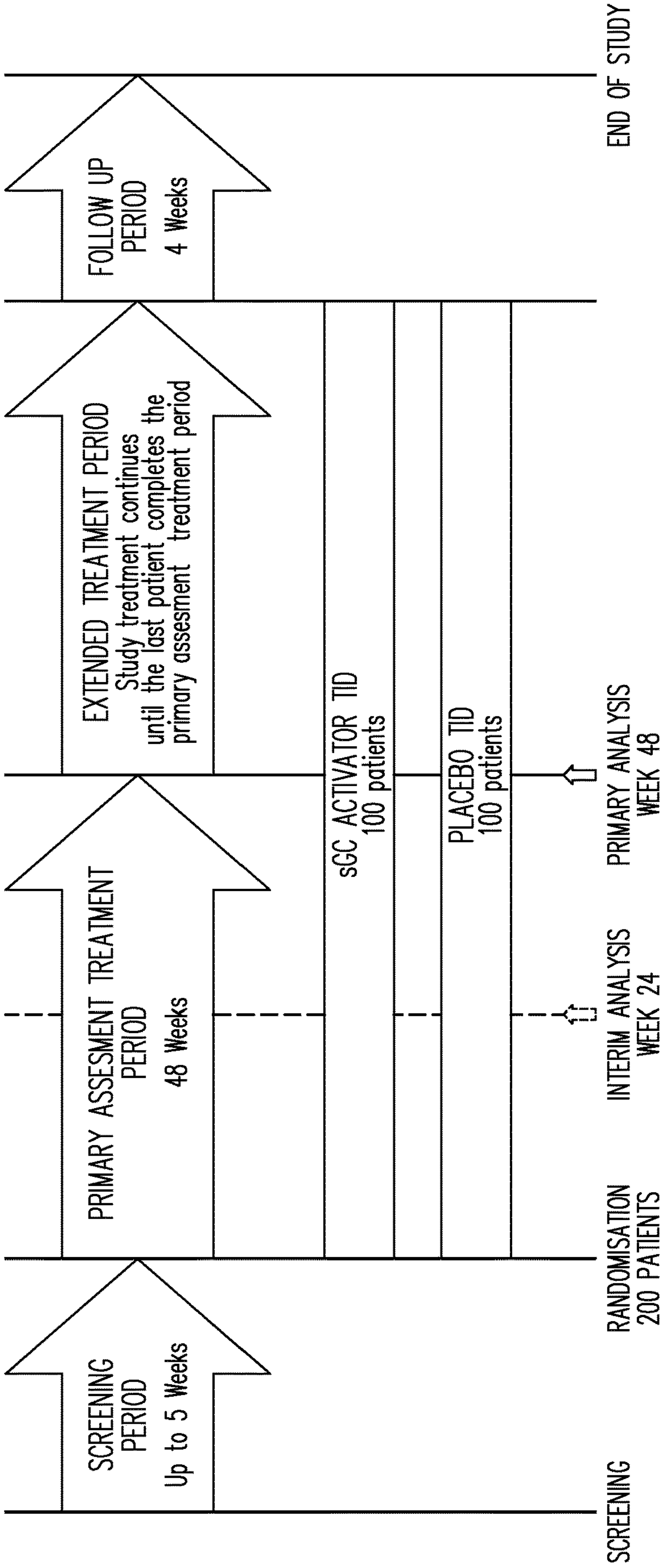

FIG. 6 shows the overall trial design comprising a randomised, placebo-controlled, double-blind, parallel-group efficacy and safety comparison of two groups (treatment and placebo) over 48 weeks.

DETAILED DESCRIPTION OF THE INVENTION

TABLE 2

| Abbreviations. | |
|---|---|
| ACE | Angiotensin converting enzyme |
| ACR-CRISS | American College of Rheumatology Composite Response Index in Systemic Sclerosis |
| ACR/EULAR | American College of Rheumatology/European Alliance of Associations for Rheumatology |
| AE | Adverse event |
| ALP | Alkaline phosphatase |
| αSMA | α-Smooth muscle actin |
| ATS/ERS | American Thoracic Society/European Respiratory Society |
| AUC | Area under the curve |
| $AUC_{t1-t2}$ | Area under the concentration-time curve of the analyte in plasma over the time interval t1 to t2 |
| BID | Bis in die (two times a day) |
| BPM | Beats per minute |
| BSA | Bovine serum albumin |
| C3M | Type 3 collagen |
| C6M | Type 6 collagen |
| CCL18 | CC chemokine ligand 18 |
| CGA | Clinician Global Assessment |
| CGI | Clinical Global Impressions scale |
| cGMP | Cyclic guanosine monophosphate |
| CKD-EPI | Chronic Kidney Disease Epidemiology |
| Cmax | Maximum plasma concentration |
| CRA | Clinical Research Associate |
| CRF | Case Report Form, paper or electronic (sometimes referred to as "eCRF") |
| CRISS | Composite Response Index in Systemic Sclerosis |
| CRP | C-reactive protein |
| CTGF | Connective tissue growth factor |
| CXCL4 | Chemokine (C-X-C motif) ligand 4 |
| CXCL9 | Chemokine (C-X-C motif) ligand 9 |
| CXCL10 | Chemokine (C-X-C motif) ligand 10 |
| CYP3A4 | Cytochrome P450 3A4 |
| DAVIX © | Digital Artery Volume Index |
| dcSSC | Diffuse cutaneous systemic sclerosis |
| DLCO | Diffusing capacity for carbon monoxide |
| DMC | Data Monitoring Committee |
| DMSO | Dimethyl sulfoxide |
| DU | Digital ulcers |
| eCFR | Electronic Case Report Form |
| ECG | Electrocardiogram |
| eGFR | Estimated glomerular filtration rate |
| EOS | End of Study |
| EOT | End of Treatment |
| EQ-5D-5L | European Quality of Life 5 Dimension |
| EuroQol Group | European Quality of Life Group |
| ESR | Erythrocyte Sedimentation Rate |
| FACIT | Functional Assessment of Chronic Illness Therapy |
| FBS | Fetal bovine serum |
| FEV1 | Forced expiratory volume in one second |
| FVC | Forced vital capacity |
| GCP | Good clinical practice |
| GGT | Gamma-glutamyl transferase |
| GRCS | Global Rank Composite Score |
| HAQ-DI | Health Assessment Questionnaire - Disability Index |
| HEPES | N-2-Hydroxyethylpiperazine-N'-2-ethanesulfonic acid |
| HIV | Human immunodeficiency virus |
| HRQOL | Health Related Quality of Life |

TABLE 2-continued

| Abbreviations. | |
|---|---|
| 8-Hydroxy dG | 8-hydroxy-2'-deoxyguanosine |
| ICH | International Council for the Harmonization of Technical Requirement for Pharmaceuticals for Human Use |
| ILD | Interstitial lung disease |
| IR | Immediate release |
| IRT | Interactive response technology |
| ISF | Investigator Site File |
| K-EDTA | Potassium ethylenediaminetetra-acetic acid |
| KL-6 | Krebs von den Lungen 6 |
| MRA | Magnetic resonance angiography |
| MRI | Magnetic resonance imaging |
| mRSS | Modified Rodnan Skin Score |
| ms | Milliseconds |
| MSD | Meso Scale Discovery |
| MTX | Methotrexate |
| NO | Nitric oxide |
| NO-sGC-cGMP | Nitric oxide soluble guanylate cyclase cyclic guanosine monophosphate |
| NRS | Numeric Rating Scale |
| NSAID | Non-steroidal anti-inflammatory drug |
| OATP | Organic anion-transporting polypeptide |
| ODQ | 2,2-Diethyl-1-nitroso-oxyhydrazine (DEA/NO) and 1H-[1,2,4]oxadiazolo-[4,3-a]quinoxalin-1-one |
| PAH | Pulmonary arterial hypertension |
| PD | Pharmacodynamic |
| PDE5 | Phosphodiesterase 5 |
| PFT | Pulmonary function testing |
| PGA | Patient Global Assessment |
| PGIC | Patient Global Impression of Change |
| PK | Pharmacokinetics |
| P.O. | Per os (by the mouth; taken orally) |
| PRO | Patient reported outcome |
| ProC3 | N-terminal pro-peptide of type III collagen |
| ProC6 | N-terminal pro-peptide of type VI collagen |
| QD | Quaque die (once a day) |
| QTcF | QT corrected for heart rate by Fridericia's cube root formula |
| RCS | Raynaud's Condition Score |
| RP | Raynaud phenomenon |
| SARS-CoV-2 | Severe acute respiratory syndrome coronavirus 2 |
| sGC | Soluble guanylate cyclase |
| SHAQ | Scleroderma Health Assessment Questionnaire |
| SICAM-1 | Soluble intercellular adhesion molecule-1 |
| SOC | Standard of care |
| SOP | Standard Operating Procedure |
| $SPO_2$ | Oxygen saturation (assessed via pulse oximetry) |
| SSc | Systemic sclerosis (systemic scleroderma) |
| SSc ILD | Systemic sclerosis-associated interstitial lung disease |
| SSPRO | Scleroderma Skin Patient Reported Outcome |
| SUSAR | Suspected Unexpected Serious Adverse Reactions |
| TdP | Torsades de pointes |
| TGFβ2 | Transforming growth factor beta-2 |
| TID | Ter in die (three times a day) |
| $t_{max}$ | Timepoint of maximum plasma concentration |
| TSAP | Trial statistical analysis plan |
| UGT | Uridine 5'-diphospho-glucuronosyltransferases |
| ULN | Upper limit of normal |
| VAS | Visual Analog Scale |
| WBC | White blood cell |
| WOCBP | Woman of childbearing potential |

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g., trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed herein above in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $—(CH_2)—$, $—(CH_2—CH_2)—$, $—(CH(CH_3))—$, $—(CH_2—CH_2—CH_2)—$, $—(C(CH_3)_2)—$, $—(CH(CH_2CH_3))—$, $—(CH(CH_3)—CH_2)—$, $—(CH_2—CH(CH_3))—$, $—(CH_2—CH_2—CH_2—CH_2)—$, $—(CH_2—CH_2—CH(CH_3))—$, $—(CH(CH_3)—CH_2—CH_2)—$, $—(CH_2—CH(CH_3)—CH_2)—$, $—(CH_2—C(CH_3)_2)—$, $—(C(CH_3)_2—CH_2)—$, $—(CH(CH_3)—CH(CH_3))—$, $—(CH_2—CH(CH_2CH_3))—$, $—(CH(CH_2CH_3)—CH_2)—$, $—(CH(CH_2CH_2CH_3))—$, $—(CHCH(CH_3)_2)—$ and $—C(CH_3)(CH_2CH_3)—$.

The term "$C_{3-n}$-cycloalkyl", wherein n is an integer 4 to n, either alone or in combination with another radical denotes a cyclic, saturated, unbranched hydrocarbon radical with 3 to n C atoms. For example, the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be $—CH_2CHF_2$, $—CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an $—S—C_{1-6}$ alkyl radical, unless otherwise specified, this shall be understood to include $—S(O)—C_{1-6}$ alkyl and $—S(O)_2—C_{1-6}$ alkyl, likewise, $—S—R_a$ may be represented as phenyl-S$(O)_m$— when $R_a$ is phenyl and where m is 0, 1 or 2.

General Synthetic Methods

The compounds of formula (I) used in the methods of the invention may be prepared by the methods and examples described in WO 2014/039434.

Methods of Therapeutic Use

For therapeutic use, the compounds of formula (I) may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compound of formula (I) may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

As mentioned above, dosage forms of the compound of formula (I) of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Specific dosage and treatment regimens will depend on factors such as the patient's general health profile, the severity and course of the patient's disorder or disposition thereto, and the judgment of the treating physician.

In this context, "combination" or "combined" within the meaning of this invention may include, without being limited, fixed and non-fixed (e.g. free) forms (including kits, or other administration, application or dosage forms) and uses, such as e.g. the simultaneous, sequential or separate use of the sGC activator and a further therapeutic agent or concomitant therapies as described herein.

The combined administration or application of this invention may take place by administering the therapeutic components together, such as e.g. by administering them simultaneously in one single or in two separate formulations. Alternatively, the administration may take place by administering the therapeutic components sequentially, such as e.g. successively in two separate formulations.

For the combination therapy of this invention the therapeutic components may be administered separately (which implies that they are formulated separately) or formulated altogether (which implies that they are formulated in the same preparation). Hence, the administration of one element of the combination of the present invention may be prior to, concurrent to, or subsequent to the administration of the other element of the combination.

Nonlimiting examples of a further therapeutic agent include cyclophosphamide, mycophenolate mofetil, tocilizumab, nintedanib and prednisone.

In one embodiment, the methods of the invention comprise administering to the patient a daily amount of from 0.1 mg to about 50 mg of a SGC activator of the invention, or a pharmaceutically acceptable salt thereof.

In another embodiment, the methods of the invention comprise administering to the patient a daily amount of from 1 mg to about 30 mg of a SGC activator of the invention, or a pharmaceutically acceptable salt thereof.

In another embodiment, the sGC activator of the invention, or a pharmaceutically acceptable salt thereof, is administered to the patient in a daily amount of from 0.1 to 100 mg; or 1 to 25 mg; or 1 to 10 mg; or 2 to 5 mg, or a pharmaceutically acceptable salt thereof.

In another embodiment, the sGC activator of the invention, or a pharmaceutically acceptable salt thereof, is administered to the patient in an amount selected from the group consisting of 1 mg, 1.5 mg, 2 mg, 2.5 mg, 3 mg, 3.5 mg, 4, mg, 4.5 mg, 5 mg, 5.5 mg, 6 mg, 6.5 mg, 7 mg, 7.5 mg, 8 mg, 8.5 mg, 9 mg, 9.5 mg, and 10 mg.

In another embodiment, the SGC activator of the invention, or a pharmaceutically acceptable salt thereof, is administered to the patient in an amount selected from the group consisting of 1, 2, 3, 4, 5, 6, 7, 8, 9 or 10 mg.

In another embodiment, the methods of the invention comprise administering to the patient up to 3 mg of a SGC activator of the invention, or a pharmaceutically acceptable salt thereof.

In another embodiment, the methods of the invention comprise administering to the patient 1 mg of a SGC activator of the invention, or a pharmaceutically acceptable salt thereof.

In another embodiment, the methods of the invention comprise administering to the patient 2 mg of a SGC activator of the invention, or a pharmaceutically acceptable salt thereof.

In another embodiment, the methods of the invention comprise administering to the patient 3 mg of a SGC activator of the invention, or a pharmaceutically acceptable salt thereof.

The vasodilatation of the sGC activator may lead to orthostatic dysregulation and hypotensive episodes. Titration of the sGC activator may allow the total daily exposure of sGC activator to be further increased while high peak concentrations are avoided.

In one embodiment, the invention relates to a method for preventing or reducing the severity of orthostatic dysregulation caused by, due to, or related to administration of a sGC activator, or a pharmaceutically acceptable salt thereof, the method comprising administering the daily dose of the sGC activator to the patient QD, BID, or TID.

In another embodiment, the sGC activator is administered to the patient QD.

In another embodiment, the sGC activator is administered to the patient BID.

In another embodiment, the sGC activator is administered to the patient TID.

In another embodiment, the methods of the invention comprise a twice daily administration to a patient of up to 3 mg of a SGC activator of the invention, or a pharmaceutically acceptable salt thereof.

In another embodiment, the methods of the invention comprise a twice daily administration to a patient of 3 mg of a SGC activator of the invention, or a pharmaceutically acceptable salt thereof, to provide a total daily amount of 6 mg of sGC activator.

In another embodiment, the methods of the invention comprise a twice daily administration to a patient of 2 mg of a SGC activator of the invention, or a pharmaceutically acceptable salt thereof, to provide a total daily amount of 4 mg of sGC activator.

In another embodiment, the methods of the invention comprise a twice daily administration to a patient of 1 mg of a SGC activator of the invention, or a pharmaceutically acceptable salt thereof, to provide a total daily amount of 2 mg of sGC activator.

In another embodiment, the methods of the invention comprise a TID dosing to a patient of up to 3 mg of a SGC activator of the invention, or a pharmaceutically acceptable salt thereof.

In another embodiment, the methods of the invention comprise TID dosing to a patient of 3 mg of a SGC activator of the invention, or a pharmaceutically acceptable salt thereof, to provide a total daily amount of 9 mg of sGC activator.

In another embodiment, the methods of the invention comprise TID dosing to a patient of 2 mg of a SGC activator of the invention, or a pharmaceutically acceptable salt thereof, to provide a total daily amount of 6 mg of sGC activator.

In another embodiment, the methods of the invention comprise TID dosing to a patient of 1 mg of a SGC activator of the invention, or a pharmaceutically acceptable salt thereof, to provide a total daily amount of 3 mg of sGC activator.

In another embodiment, the invention relates to methods for initiating treatment of the patients with an sGC activator. A nonlimiting example of initial treatment comprising uptitrating the patients from a small dose to the target dose.

In one embodiment, the initial treatment of the patient comprises:

administering the sGC activator of the invention for two weeks (weeks one and two of treatment) at a dose of 1 mg TID, administering the sGC activator for two weeks (weeks three and four) at a dose of 2 mg TID, and administering the sGC activator after week four at a dose of 3 mg TID.

In another embodiment, the invention relates to methods for treating patients with systemic sclerosis, including patients with diffuse cutaneous systemic sclerosis (dcSSc) and vasculopathy, wherein the treatment produces an improvement in:

rate of decline in FVC (mL) over 48 weeks over placebo, change from baseline in mRSS at Week 48, revised CRISS score at Week 48 (Achievement of ≥20% improvement from baseline to Week 48 in at least 3 of the 5 core set measures, except ≥5% in FVCpercent predicted), change from baseline in HAQ-DI score at Week 48, change from baseline in the PGA VAS score at Week 48, change from baseline in the CGA VAS score at Week 48, composite measure of RP activity at Week 48, change from baseline in DU net burden at Week 48, an/or time to treatment failure, defined as the time to one of the following events (whichever occurs first) occurring over the 48-week and extended treatment period selected from the group consisting of:

death, absolute decline in percent-predicted FVC>10% relative to baseline,

≥25% increase in mRSS and an increase in mRSS of >5 points, and initiation or dose change of immunomodulating/immunosuppressive therapy for clinically significant deterioration of dcSSc.

In another embodiment, the invention relates to methods for treating patients with systemic sclerosis, including patients with diffuse cutaneous systemic sclerosis (dcSSc) and vasculopathy, wherein the treatment produces an improvement in:

- absolute change from baseline in the FACIT—Fatigue Scale score at Week 48,
- absolute change from baseline in SSPRO score at Week 48,
- absolute change from baseline in EQ-5D-5L score at Week 48,
- absolute change from baseline in Worst Pain NRS at Week 48,
- absolute change from baseline in the six individual SHAQ domain scores (pain, intestinal
- problems, respiratory problems, RP, finger ulcers, disease severity) at Week 48, PGIC score at Week 48,
- change from baseline in DLCO in percent predicted at Week 48,
- Global Rank Composite Score (GRCS) at the end of the extended treatment period or at the end of the 48-week primary assessment treatment period versus patients who do not participate in the extended treatment period,
- annual rate of decline in FVC (mL) over the Primary Assessment Treatment Period and extended treatment period
- change from baseline in presence or absence tendon friction rubs at Week 48,
- change from baseline in joint involvement (tender and swollen joint count—28) at Week 48, and/or
- absolute change from baseline in RCS at Week 48.

Patients being treated with the sGC activator of the invention may be treated with one or more additional therapeutic agents. Nonlimiting examples of such one or more additional therapeutic agents include cyclophosphamide, mycophenolate mofetil, tocilizumab, nintedanib and prednisone.

Clinical Trial Protocol

Clinical Trial

The below describes a clinical trial protocol directed to treatment of patients with early progressive dcSSc and vasculopathy. The trial will assess the efficacy, safety, and tolerability of the compounds of the invention compared with placebo on a background of local standard of care (SOC) therapy in adult patients with early progressive dcSSc and vasculopathy.

Diffuse cutaneous systemic sclerosis (dcSSc) is a subtype of systemic scleroderma (systemic sclerosis) and is characterized by skin hardening (fibrosis) and problems in many organs of the body. Symptoms include Raynaud's phenomenon; skin fibrosis beginning on the fingers and face that rapidly becomes generalized; "spider veins" (telangiectasias) on the thorax, face, lips, tongue, and fingers; gastroesophageal reflux; and difficulty eating (dysphagia) along with weight loss, vomiting, diarrhea or constipation. Dry mouth and dental involvement can occur. Joint pain (arthralgias), muscular pain, weakness, cramps, and destruction of the tips of the fingers or toes (acroosteolysis) are frequent. More serious problems involving the lung and kidneys may also occur. The exact cause of the condition is unknown.

Trial Objectives and Endpoints

Main objectives: This trial will assess the efficacy, safety, and tolerability of Compound 114 3 mg TID compared with placebo on a background of local SOC therapy in adult patients with early progressive dcSSc and vasculopathy.

The primary objective is to demonstrate superiority of Compound 114 at a target dose of 3 mg TID over placebo based on the mean difference in annual rate of decline in FVC over 48 weeks. The treatment effect of primary interest will be based on all randomised patients including the effects of any changes of treatment, i.e., a treatment policy strategy will be used.

Secondary objectives are to demonstrate superiority of Compound 114 over placebo for absolute change from baseline in mRSS, FVC (% predicted), patient and physician global assessment, HAQ-DI, RP activity), and DU net burden at Week 48, the ACR-CRISS, revised CRISS and for time to treatment failure. Additional objectives are to evaluate safety, PK, PD, and exploratory biomarkers.

Primary endpoint: The primary endpoint is the rate of decline in FVC (mL) over 48 weeks.

Key secondary endpoints include:

- Absolute change from baseline in mRSS at Week 48
- Revised CRISS score at Week 48 (Achievement of ≥20% improvement from
- baseline to Week 48 in at least 3 of the 5 core set measures, except ≥5% in FVCpercent predicted)
- Absolute change from baseline in HAQ-DI score at Week 48

Secondary endpoints as follows:

- ACR-CRISS score at Week 48
- Absolute change from baseline in FVC (% predicted) at Week 48
- Absolute change from baseline in the PGA VAS score at Week 48
- Absolute change from baseline in the CGA VAS score at Week 48
- Composite measure of RP activity at Week 48
- Absolute change from baseline in DU net burden at Week 48
- Time to treatment failure, defined as the time to one of the following events (whichever occurs first) occurring over the 48-week and extended treatment period:
  - death,
  - absolute decline in percent-predicted FVC≥10% relative to baseline,
  - ≥25% increase in mRSS and an increase in mRSS of >5 points,
  - initiation or dose change of immunomodulating/immunosuppressive therapy for clinically significant deterioration of dcSSc as outlined herein.

Further Objectives and Further Endpoints

Further objectives: Further objectives include the efficacy, PK and changes in biomarkers after 48 weeks of treatment with Compound 114 compared with placebo in adults with early dcSSc.

Further endpoints: Further endpoints are as follows:

Efficacy:

- Absolute change from baseline in the FACIT—Fatigue Scale score at Week 48
- Absolute change from baseline in SSPRO score at Week 48
- Absolute change from baseline in EQ-5D-5L score at Week 48
- Absolute change from baseline in Worst Pain NRS at Week 48

- Absolute change from baseline in the six individual SHAQ domain scores (pain, intestinal problems, respiratory problems, RP, finger ulcers, disease severity) at Week 48
- PGIC score at Week 48
- Absolute change from baseline in DLCO in percent predicted at Week 48
- The Global Rank Composite Score (GRCS) at the end of the extended treatment period or at the end of the 48-week primary assessment treatment period for patients who do not participate in the extended treatment period
- Proportions of patients who have a treatment failure (as defined above) or discontinue treatment (non-responders) over the 48-week and extended treatment period
- Annual rate of decline in FVC (mL) over the Primary Assessment Treatment Period and extended treatment period
- Change from baseline in presence or absence tendon friction rubs at Week 48
- Change from baseline in joint involvement (tender and swollen joint count—28) at Week 48
- Absolute change from baseline in RCS at Week 48

Pharmacokinetics:

Further PK parameters will be calculated through Week 36 as feasible and may include, but are not limited to:

- Cmax (maximum measured concentration of the analyte in plasma)
- tmax (time from dosing to maximum measured concentration of the analyte in plasma)
- AUCt1-t2 (area under the concentration-time curve of the analyte in plasma over the time interval t1 to t2)

Biomarkers:

- Change in blood biomarkers including but not limited to KL-6, CRP, CCL18, ProC3, C3M, ProC6, C6M, CXCL4, 8 isoprostane, 8 hydroxy dG, sICAM-1, endothelin-1, endostatin, connective tissue growth factor (CTGF), CXCL9, CXCL10 from baseline up to Week 48.
- Changes of gene expression in skin biopsies and blood from baseline up to Week 48 (see RNA gene expression sub-study, Section 5.4.1).
- Changes in numbers of a SMA-positive fibroblasts, skin thickness and other histopathological parameters based on immunohistochemistry analysis in skin biopsies from baseline up to Week 48 (see RNA gene expression sub study, Section 5.4.1).
- Change in Digital Artery Volume Index (DAVIX©), a novel quantitative MRI-based score for the assessment of the blood flow in the arteries, from baseline up to Week 48 (see MRA sub-study, Section 5.4.1).

More details and additional further endpoints may be defined in the trial statistical analysis plan (TSAP).

Description of Design and Trial Population

Overall Trial Design

This is a multi-center, multi-national, prospective, randomised, placebo-controlled, double blind, parallel-group, Phase II clinical trial to investigate the efficacy and safety of oral Compound 114 at a target dose of 3 mg TID, in adult patients with early progressive dcSSc and vasculopathy.

Patients will be enrolled in the trial and screened for eligibility once they have signed the informed consent. The screening period has a maximum of 5 weeks. Eligible patients will proceed to the 48-week treatment period. Compound 114 versus placebo use will be established in a 1:1 randomization after the screening period.

The treatment period includes a 4-week up-titration of Compound 114 from 1 mg to 3 mg TID: Compound 114 1 mg will be given TID for 2 weeks. If tolerated, Compound 114 2 mg TID will be given for 2 weeks and then escalated to 3 mg TID. If the patient develops symptomatic orthostatic hypotension on 2 mg TID, then they have to stop trial medication and contact the site for dose adjustment. The same procedure will be followed after escalation from 2 mg to 3 mg TID. Every dose adjustment will require a patient visit at the site. It is anticipated that approximately 10% of patients may not be able to fully titrate up to the 3 mg TID dose.

The main efficacy analysis will be assessed at Week 48. After completing the first 48 weeks of treatment, patients may continue to receive their assigned trial treatment in the extended treatment period, until the last patient has completed the treatment period. Patients will then enter a 4 week follow up period that does not include trial treatment, for ongoing safety and efficacy data collection. The patient's trial participation is complete when they have completed the last planned visit (i.e., EOS, 4 weeks after EOT).

A summary of the overall trial design is shown in FIG. 6.

Compound 114 will be in IR formulation and will be up-titrated during the primary assessment treatment period as tolerated, from 1 mg TID to 2 mg TID after two weeks, and then from 2 mg TID to 3 mg TID after an additional two weeks. It is anticipated that approximately 10% of patients may not be able to fully titrate up to the 3 mg TID dose.

Discussion of Trial Design, Including the Choice of Control Group(s)

This will be a randomised, placebo controlled, double-blind trial. The rationale for a blinded placebo control arm is that patients with SSc may have waxing and waning symptoms and signs. Thus, the benefit of an experimental treatment must be judged against the apparent response (or lack thereof) in a placebo population. To minimize bias, the patients must be randomly assigned to either placebo or investigational drug and neither the patient nor study personnel should be aware of the assignment. With the exceptions noted herein, individuals involved in data capture, cleaning, programming and analysis will remain blinded to treatment assignment until all patients have completed the trial.

One of the most difficult aspects of studying SSc is the paucity of validated end points. Various endpoints have been used in previous clinical trials, including decrease in skin thickness utilizing the mRSS, slowing of lung function decline as demonstrated by FVC, and composite endpoints including mRSS, FVC, patient and physician global assessments and the HAQ-DI. None of these have been successfully used to register a product for the broad indication of SSc, although changes in lung function have been used to register products for the treatment of interstitial lung disease in patients with SSc.

Based on this, FVC is chosen as the primary endpoint, with the understanding that it will be important to also show efficacy in non-pulmonary endpoints (secondary endpoints). In the absence of a reliable composite endpoint, we propose to include multiple secondary endpoints including, but not limited to, RCS, reduction in the number of digital ulcers (net ulcer burden), assessment of skin thickening (mRSS) and patient and clinician global assessments, as well as patient reported outcomes, such as the HAQ-DI, FACIT, and SSPRO. These endpoints were selected based on publications demonstrating their ability to detect meaningful changes in patients with SSc.

In addition, the trial will use the currently available composite endpoints, including the ACR-CRISS, the revised CRISS, and the GRCS. (See, e.g., D Khanna et al., "The American College of Rheumatology provisional composite response index for clinical trials in early diffuse cutaneous systemic sclerosis," Arthritis Rheumatol 2016; 68(2):299-311; D. Khanna et al., "New composite endpoint in early diffuse cutaneous systemic sclerosis: revisiting the provisional American College of Rheumatology Composite Response Index in Systemic Sclerosis," Ann Rheum Dis 2021; 80:641-650; and K. M. Sullivan et al., "Myeloablative autologous stem-cell transplantation for severe scleroderma," N Engl J Med 2018; 378(1):35-47.)

The 48-week primary assessment treatment period duration is selected to allow for time to titrate to 3 mg TID and to allow evaluation of the efficacy, safety, and tolerability of Compound 114 3 mg TID compared with placebo on a background of local SOC therapy in adult patients with early progressive dcSSc and vasculopathy. The extended treatment period was included to provide trial patients with continued treatment and assessment, and to collect further efficacy and safety evaluation.

Data cleaning, central medical review, and quality review of the data and report planning will be performed in a blinded manner.

The trial will include an external DMC to review blinded and unblinded safety data quarterly throughout the duration of the trial, at interim analysis and final analysis.

Selection of Trial Population

A total of approximately 200 patients with early progressive diffuse cutaneous systemic sclerosis will be entered into the trial. Approximately 150 sites are planned across approximately 30 countries. Approximately one to two patients will be randomised at each site. If enrolment is delayed, additional sites may be recruited.

Screening of patients for this trial is competitive, i.e. screening for the trial will stop at all sites at the same time once a sufficient number of patients has been screened. Investigators will be notified about screening completion and will then not be allowed to screen additional patients. Patients already in screening at this time will be allowed to continue to randomization if eligible.

Re-testing during the screening period is allowed once (e.g. if the Investigator believes an ineligible laboratory test is the result of an error or extenuating circumstances, the test can be repeated once without the patient having to be re-screened).

Re-screening is also allowed once provided that the reasons for screen failure were reversible and have been resolved, based on Investigator judgment. A patient is considered a "re screener" if they were not eligible for the trial initially and is subsequently re-screened, going through the informed consent process for a second time, receiving a new unique patient number and repeating the screening period assessments.

A log of all patients enrolled into the trial (i.e. who have signed informed consent) will be maintained in the ISF irrespective of whether they have been treated with investigational drug or not.

If retrospectively it is found that a patient has been randomised in error (=did not meet all inclusion criteria or met one or more exclusion criteria), the sponsor or delegate should be contacted immediately. Based on an individual benefit-risk assessment a decision will be made as to whether continued trial participation is possible or not.

Main Diagnosis for Trial Entry

The main diagnosis for trial entry is SSc (according to American College of Rheumatology/European Alliance of Associations for Rheumatology [ACR/EULAR] Criteria, 2013), the subtype diffuse cutaneous as defined by LeRoy et al., "Scleroderma (systemic sclerosis): classification, subsets and pathogenesis," J Rheumatol 1988; 15(2):202-205.

The trial population should be enriched with patients who have earlier, more progressive disease. This will be accomplished by using criteria historically associated with "active disease" by both clinical (criterion #6) and biomarker (criterion #7) inclusion criteria. In addition to the standard biomarkers associated with active inflammation, such as CRP and ESR, the biomarker criteria have been enhanced by the addition of KL-6. Elevated KL-6 (>1000 U/mL) has been associated with active, progressive ILD in several studies. See M. Kawana et al., "Elevated serum Krebs von den Lungen-6 in early disease predicts subsequent deterioration of pulmonary function in patients with systemic sclerosis and interstitial lung disease," J Rheumatol 2016; 43(10):1825-1831; G. A. Salazar et al., "KL-6 but not CCL-18 is a predictor of early progression in systemic sclerosis-related interstitial lung disease" Journal of Rheumatology, Published online Jul. 1, 2018, doi: 10.3899/jrheum.170518; 2018. p. 1153-1158; and H. Satoh et al., "Increased levels of KL-6 and subsequent mortality in patients with interstitial lung diseases," J Intern Med 2006; 260:429-434.

Inclusion Criteria

- Signed and dated written informed consent in accordance with ICH-GCP and local legislation prior to admission to the trial
- Male or female patients aged? 18 years at time of consent (or above legal age, e.g. UK≥16 years).
- Patients must fulfil the 2013 ACR/EULAR classification criteria for SSc.
- Patients must be diagnosed with diffuse cutaneous SSc (widespread skin fibrosis with skin involvement proximal to elbows and/or knees) as defined by LeRoy et al., "Scleroderma (systemic sclerosis): classification, subsets and pathogenesis," J Rheumatol 1988; 15(2):202-205.
- SSc disease onset (defined by first non-RP symptom) must be within 5 years of Visit 1.
- Evidence of active disease, defined as having at least one of the following:
  - New onset of SSc within the last 2 years of Visit 1 OR
  - New skin involvement or worsening of two new body areas within 6 months of Visit 1 (out of the 17 body areas defined by mRSS assessment, documented in clinical files) OR
  - New involvement or worsening of one new body area if either chest or abdomen within 6 months of Visit 1 OR
  - Worsening of skin thickening (≥2 mRSS points) within 6 months of Visit 1 OR
  - ≥1 tendon friction rub.
- Elevated biomarkers on Visit 1 (screening) defined as at least one of the following:
  - CRP≥6 mg/L (≥0.6 mg/dL), OR
  - Erythrocyte sedimentation rate (ESR)≥28 mm/h, OR
  - KL-6≥1000 U/mL.
- Evidence of significant vasculopathy, defined as:
  - Active DU(s) on Visit 1 OR
  - Documented history of DU(s), OR
  - Previous treatment of RP with prostacyclin analogs or ≥1 other medications, including Nitrates, NO donors in any form, including topical; phosphodiesterase 5

(PDE5) inhibitors (e.g. sildenafil, tadalafil, vardenafil); nonspecific PDE5 inhibitors (theophylline, dipyridamole) OR
RP with elevated CRP≥6 mg/L
If none of the four criteria above are met, the patient can be entered if the diagnosis of ILD has been confirmed
Evidence of early fibrosis at Visit 1, defined as a mRSS of ≥10 points, AND
FVC≥50% of predicted normal.
If patients receive concomitant treatments for dcSSc, these need to be on stable doses as follows:
Mycophenolate mofetil/sodium: stable dose for at least 4 months prior to randomization
Methotrexate: stable dose and route of administration for at least 4 months prior to randomization; folic acid supplementation according to local SOC should be taken before randomization and during the trial
Azathioprine: stable dose for at least 4 months prior to randomization
Oral corticosteroids (≤10 mg/day of prednisone or equivalent): stable dose for at least 2 weeks prior to randomization
NSAIDs: stable dose for at least 2 weeks prior to randomization
ACE inhibitors: stable dose for at least 2 weeks prior to randomization
Calcium channel blockers: stable dose for at least 2 weeks prior to randomization
Male patients able to father a child must be willing to use condoms if their sexual partner is a woman of childbearing potential (WOCBP). WOCBP must be ready and able to use highly effective methods of birth control per ICH M3 (R2). Such methods should be used throughout the trial. A list of contraceptive methods meeting these criteria is provided in the patient information and in Section 4.2.2.3.

Exclusion Criteria

Any known form of pulmonary hypertension.
Pulmonary disease with FVC<50% of predicted.
Limited cutaneous SSc at screening. Other autoimmune connective tissue diseases, except for fibromyalgia, scleroderma-associated myopathy and secondary Sjogren syndrome.
Diffusing capacity for carbon monoxide (DLCO) (haemoglobin corrected)<40% of predicted at screening.
Any history of scleroderma renal crisis.
Estimated glomerular filtration rate (eGFR)<30 mL/min/1.73 m2 (CKD-EPI formula) or on dialysis at screening.
Cirrhosis of any Child-Pugh class (A, B or C) (Appendix 10.9).
Cholestasis at present, or ALP>4×ULN, or ALP>2×ULN and GGT>3×ULN at Screening.
Known, severe gastric antral telangiectasias (watermelon stomach).
Any history of bronchial artery embolization or massive hemoptysis. (Massive hemoptysis is defined as acute bleeding >240 mL in a 24 hour period or recurrent bleeding >100 mL/day over consecutive days).
Active hemoptysis or pulmonary hemorrhage, including events managed by bronchial artery embolization.
Unstable cardiovascular, pulmonary (other than trial indication) or other disease within 6 months prior to Visit 1 and/or during the screening period (e.g. acute coronary artery disease, heart failure, and pulmonary embolism).
Systolic blood pressure <100 mm Hg or known history of moderate or severe symptomatic orthostatic dysregulation as judged by the Investigator before start of trial treatment.
Sitting heart rate <50 bpm at the Screening Visit.
Laboratory values: haemoglobin <9.0 g/dL, white blood cell (WBC) count <3000/mm3 (<3 ×109/L), platelet count <100,000/mm3 (<100×109/L)
Known heart failure with left ventricular ejection fraction <40% prior to screening.
A marked baseline prolongation of QT/QTc interval by a repeated demonstration in at least 2 ECG measurements within the triplicate or in 2 triplicates of a QTc interval (>450 ms in male and >470 ms in female patients). A history of additional risk factors for Torsades de pointes (TdP) (e.g., heart failure, hypokalemia, family history of Long QT Syndrome).
Use of following treatments and therapies:
Nitrates or NO donors (e.g., amyl nitrate) in any form, including topical; phosphodiesterase (PDE) 5 (PDE5) inhibitors (e.g., sildenafil, tadalafil, vardenafil); and nonspecific PDE5 inhibitors (theophylline, dipyridamole) within 2 weeks prior to randomization
Prostacyclin analogs (oral beraprost for digital ulcers/Raynaud's disease and short-term/intermittent therapy of up to 21 days with intravenous prostacyclin analogs for digital/vascular lesions is allowed) within 2 weeks prior to randomization
Nintedanib, pirfenidone, erguride, tyrosine-kinase inhibitors (e.g., imatinib, nilotinib, dasatinib), janus-kinase inhibitors within 2 weeks prior to randomization
sGC-stimulators/activators (other than Compound 114) within 4 weeks prior to randomization
Treatment with clinically relevant OATP1B1/3 inhibitors and clinically relevant UGT inhibitors/inducers within 4 weeks prior to randomization
Drugs with known risk of Torsade de Pointes within 5 half-lives prior to randomization
Other investigational drugs within 1 month or 5 half-lives (whichever is greater) prior to randomization
Ultraviolet phototherapy within 6 weeks prior to randomization
Use of the following immunomodulating/immunosuppressive treatments and corticosteroids:
Anakinra within 1 week prior to randomization
Etanercept within 2 weeks prior to randomization
Cyclophosphamide, cyclosporine A, hydroxychloroquine, tacrolimus, sirolimus, colchicine, D-penicillamine, mizoribine and intravenous immunoglobulin within 4 weeks prior to randomization
Infliximab, certolizumab, golimumab, adalimumab, abatacept, tocilizumab, brodalumab and leflunomide within 8 weeks prior to randomization
Rituximab or other anti-CD20 antibodies within 6 months prior to randomization
Non-investigational or investigational cell-depleting therapies, including but not limited to alemtuzumab, anti-CD4, anti-CD5, anti-CD3, anti-CD19 within 18 months prior to randomization
Previous treatment with chlorambucil, bone marrow transplantation, total lymphoid irradiation, thalidomide, antithymocyte globulin, plasmapheresis, or extracorporeal photopheresis
Oral prednisone>10 mg/day or equivalent, intravenous and intramuscular corticosteroids within 2 weeks prior to randomization Local background standard of care must not be terminated for the patient to be eligible to participate in the study.

Relevant chronic or acute infections including but not limited to human immunodeficiency virus (HIV) and viral hepatitis. The corresponding laboratory tests will be performed during screening. A patient can be re-screened if the patient was treated and is cured from the acute infection.

The patient has an active infection with SARS-CoV-2 (or is known to have a positive test) from screening until randomization.

Major surgery (major according to the Investigator's assessment) planned during the trial.

Any documented active or suspected malignancy or history of malignancy within 5 years prior to screening, except appropriately treated basal cell carcinoma of the skin or in situ carcinoma of uterine cervix.

History of clinically relevant allergy/hypersensitivity that would interfere with trial participation including allergy to investigational product/placebo or its excipients.

Any other medical condition that in the Investigator's opinion poses a safety risk for the patient or may interfere with the trial objectives.

Patients not expected to comply with the protocol requirements or not expected to complete the trial as scheduled (e.g. chronic alcohol or drug abuse or any other condition that, in the Investigator's opinion, makes the patient an unreliable trial participant).

Previous randomization/treatment in this trial.

Currently enrolled in another investigational device or drug trial, or less than 1 month or 5 half-lives (whichever is greater) since ending another investigational device or drug trial(s) or receiving other investigational treatment(s) prior to randomization.

Women who are pregnant, nursing, or who plan to become pregnant while in the trial.

MRA sub-study: Contraindication to MRI or inability to undergo MRI (e.g. implanted medical devices that are contraindicated for MRI and cannot be removed (e.g. cardiac pacemaker, neurostimulation systems), severe claustrophobia).

Patients who are legally institutionalized according to national law.

Treatments

The investigational medicinal product in the trial is the sGC activator formulated as an immediate release (IR) formulation.

Method of Assigning Patients to Treatment Groups:

After the assessment of all in- and exclusion criteria, each eligible patient will be randomised to a treatment group according to a randomization plan in a 1:1 ratio at Visit 2. Randomization codes will be generated through a validated software and kept blinded to the trial team, sites and patients. An interactive response technology (IRT) system will be used to screen patients, perform drug assignment, manage initial/re-supply ordering of drug supplies and handle emergency un-blinding.

The Investigator will receive all necessary instructions from the sponsor to access the IRT. Detailed IRT functions and procedures will be documented in the User Requirement Specifications mutually agreed by the sponsor and the IRT vendor. Note that the medication number is different from the patient number (the latter is generated during screening via the IRT System).

Drug Assignment and Administration of Doses for Each Patient:

Patients will be randomised to enter either the active treatment group or the placebo control group (Table 3). The dose will be uptitrated from 1 mg TID to 3 mg TID or matching placebo. All patients will start on a dose of 1 mg TID of Compound 114 or matching placebo. Up titration will occur after 14 days and after 28 days. Patients who do not tolerate an up titration, e.g. due to orthostatic dysregulation, should follow the guidance described herein. These patients will continue receiving 2 mg or 1 mg (or placebo).

TABLE 3

Treatment assignments and dose regimen

| | Weeks 1 & 2 | Weeks 3 & 4 | Weeks 5 to 48 | Weeks 48 to EOT |
|---|---|---|---|---|
| Randomization Allocation | Dispensed at Visit 2 | Dispensed at Visit 3 | Dispensed at Visits 4 through 11 | Dispensed at Visits 12 through visit prior to EOT |
| Active Treatment Group | 1 mg Compound 114 TID | 2 mg Compound 114 TID | 3 mg Compound 114 or highest tolerated dose TID | 3 mg Compound 114 or highest tolerated dose TID |
| Placebo Control Group | matching placebo TID | matching placebo TID | matching placebo TID | matching placebo TID |

It is recommended that the first daily dose is taken in the morning, the middle dose around lunchtime, and the third dose in the evening (one tablet at each time point). There must be at least four hours in between trial treatment intake. If a dose is missed this should not be rectified by taking two doses at the next time point.

The trial treatment should be taken with a glass of water and can be taken with or without food. For facilitation of swallowing, the tablets may be broken or crushed. The crushed tablets may be suspended in tap water. Crushed or suspended tablets must be used within two hours after crushing. It must be ascertained that the complete dose is taken. The last dose of trial treatment will be administered in the evening of the day before the EOT Visit.

All trial treatment assignments including up/down-titrations and replacement kits will be managed through the IRT system. Patients will be informed that the medication could either be active trial treatment or placebo.

During a coronavirus disease 2019 or similar pandemic, physical visits to the sites may need to be restricted to ensure patient safety. Based on a thorough assessment of the benefits and risks, the Investigator may still decide to continue the trial treatment and trial treatment may be shipped to the patient's home if acceptable according to local law and regulations.

Potential down-titrations (dose reductions) can be done by the investigational site. This will be managed via the IRT system. Dose reductions must not be performed by instructing the patient to take less than the three daily doses. The patient will be informed that down titrations may be needed as decided by the Investigator. Down-titrations will require a (unscheduled) visit at the trial site.

Rules for Titration in Case of Interruption of Trial Treatment

Since an interruption of trial treatment may have an influence on the tolerance, the following rules will apply for the safety of the patient:

- An interruption of trial treatment is defined as any occurrence where 4 consecutive doses* or more were not administered (i.e. missed or dosing temporarily discontinued). *One dose refers to an individual timepoint e.g. morning dose, or middle dose or evening dose.
  - If less than 4 consecutive doses of trial treatment are missed then the next dose of trial treatment should be taken as scheduled.
- After an interruption of trial treatment the patient should be restarted at Compound 114 1 mg/placebo TID independent from the dose the patient was on before unless the patient was down-titrated due to an adverse event (see Section 4.1.4.2) in which case:
  - If they had been on Compound 114 2 mg/3 mg/placebo they would re-start on Compound 114 1 mg/placebo.
  - If they had been on Compound 114 1 mg/placebo then they should restart on Compound 114 1 mg/placebo.
- Before any up-titration occurs, the patient must have taken the preceding dose for at least 10 consecutive days. This applies throughout the treatment period.
  - This may mean that a patient due to be up-titrated at Visit 3 or 4 (as per Table 4.1.4: 1) is held at their current dose until their next scheduled visit. They could also be up-titrated at an unscheduled visit once this requirement is met.
- If interruption for any reason occurs after Visit 4, subsequent up-titration will be allowed either at a scheduled or unscheduled visits.
- Patients with an interruption on Compound 114 2 mg or 3 mg or matching placebo will need to return to the clinic either for the next scheduled or an unscheduled visit to receive Compound 114 1 mg/placebo tablets before continuation of trial treatment.

Rules for Down-Titration in Case of Intolerance to Trial Treatment

If a patient has an AE that the Investigator believes may be related to trial treatment, then the Investigator may either interrupt a patient's trial treatment (re-start to follow the rules above) or dose reduce the patient as described below:

- If the patient reports symptomatic orthostatic hypotension between the regular visits, investigator should consider interruption of trial treatment until the unscheduled visit.
- If the patient is on Compound 114 1 mg TID or matching placebo the patient will be taken off trial treatment.
- If the patient is on Compound 114 2 mg TID or 3 mg TID (or corresponding matching placebo) and interrupts trial treatment:
  - less than 4 consecutive doses, then the patient will be down-titrated one level i.e.:
    - Compound 114 2 mg/placebo goes to Compound 114 1 mg TID/placebo.
    - Compound 114 3 mg/placebo goes to Compound 114 2 mg TID/placebo.
  - 4 consecutive doses or more, then the patient will be down-titrated to Compound 114 1 mg TID or placebo.
- Dose-reduction must NOT be performed by taking less than the three daily doses or by splitting tablets so that a whole tablet isn't taken.
- If the patient has already had an interruption/down-titration due to an AE and experiences a second AE that the Investigator believes is related and would require further down-titration, then the patient should permanently discontinue trial treatment.
- In case of persistent AEs despite dose reduction, or severe adverse effects at any dose, permanent treatment discontinuation should be considered.

Up-titration for patients who were down-titrated or interrupted for a related AE is not permitted.

All changes in trial-treatment dose, will require a scheduled or unscheduled visit to the site and an IRT call.

Blinding and Procedures for Unblinding

Blinding

With the exceptions noted below, patients, investigators, central reviewers, and everyone involved in trial conduct or analysis or with any other interest in this double-blind trial will remain blinded regarding the randomised treatment assignments until the database is declared ready for analysis according to the sponsor's Standard Operating Procedures (SOPs). Further details regarding the timepoint of unblinding the database for analysis will be documented in the TSAP.

The randomization codes will be provided to bioanalytics before the last patient completed the first 48-week treatment period of the trial to exclude placebo samples from the PK analysis. The randomization code or the results of their measurements will not be disclosed until the database lock.

An external independent statistician will receive data and treatment codes to produce quarterly safety reports for the DMC. The external independent statistician will also receive data and treatment codes to perform the interim analysis, which is planned following approximately 80% of patients completing the first 24 weeks of treatment. The DMC and project team will have access to the aggregate results of the interim analysis.

In order to expedite the population PK and PK-PD analyses and ensure timely delivery of PK/PD results after data base lock, specific data must be unblinded and the treatment information must be made available to selected individuals. It should be noted no PK/PD results will be communicated to the project and trial team prior to database lock.

Prior to the interim analysis, logistics and access plans will document the details of data transfer, timelines and individual functions involved for both the interim analysis and the population PK and PK-PD analyses.

Unblinding and Breaking the Code

Emergency unblinding will be available to the Investigator via IRT. It must only be used in an emergency situation when the identity of the trial drug must be known to the Investigator in order to provide appropriate medical treatment or otherwise assure safety of trial participants. The reason for unblinding must be documented in the source documents and/or appropriate CRF page.

Due to the requirements to report Suspected Unexpected Serious Adverse Reactions (SUSARs), it may be necessary to access the randomization code for individual patients during trial conduct. The access to the code will only be given to authorized Pharmacovigilance representatives for processing in the PV database system and not be shared further.

Other Treatments, Emergency Procedures, Restrictions

Other Treatments and Emergency Procedures

The following immunomodulating/immunosuppressive medications are allowed and should be at stable dose for at least 4 months prior to randomization and during the trial until EOT.

Dose reduction of concomitantly used medications may be permitted in exceptional situations,

- Mycophenolate mofetil/sodium
- MTX—Patients on MTX should be taking folic acid supplementation according to local SOC before randomization and during the trial to minimize the likelihood of MTX associated toxicity. (For MTX, stable dose means stable dose and route of administration of this drug)
- Azathioprine—Concomitant use of xanthine oxidase inhibitors such as allopurinol and febuxostat should be avoided. If concomitant use of xanthine oxidase inhibitors is needed, the dose of azathioprine should be reduced to a quarter of the normal dose, because xanthine oxidase inhibitors reduce the metabolism of azathioprine.

If these medications are not used concomitantly, but have been used before, they should have been stopped at least 4 weeks prior to randomisation (Visit 2).

In addition, the following concomitant medications are allowed and should be at stable doses for at least 2 weeks prior to randomization and during the trial until EOT visit (Decreases in doses of these medications for safety reasons are permitted):

- Oral corticosteroids (≤10 mg/day of prednisone or equivalent)
- NSAIDs
- ACE inhibitors
- Calcium channel blockers
- Endothelin—receptor antagonists These treatments will also be allowed as new-onset during the study at the discretion of the investigator to treat SSc-specific adverse events (e.g., Raynaud's phenomena, joint inflammation, new onset renal crisis).

For patients who receive corticosteroids and/or NSAIDs, prophylactic treatment with proton-pump inhibitors or histamine-2 receptor blockers may be added at the investigator's discretion, according to local SOC.

Analgesics up to the maximum recommended dose may be used as required for pain. However, patients should be discouraged from using analgesics, including NSAIDs, within 12 hours prior to performance of efficacy assessments at a clinic visit.

In Case of Deterioration of dcSSc

In case of a clinically significant deterioration of dcSSc, initiation of therapy or dose change of immunomodulating/immunosuppressive therapy as well as corticosteroids >10 mg/day of prednisone or equivalent are allowed at or after the Week 24 Visit. The use of these medications before Week 24 is discouraged except in the case of clinically significant deterioration. If restricted therapies are started for treatment of significant deterioration, the study drug should be discontinued.

Clinically significant deterioration is defined as:

- Absolute decline since baseline in FVC percent predicted ≥10% (for example, if FVC percent predicted changes from 70% at baseline to <60%, other causes, e.g. respiratory tract infection to be excluded), or
- Relative change from baseline in mRSS of ≥25% and an absolute change from baseline of >5 points, or
- Clinically significant deterioration in other organ systems or clinical parameters at the discretion of the Investigator.

Medication as individually indicated per discretion of the Investigator is allowed unless covered by medication restrictions described herein as well as given in inclusion/exclusion criteria. If not permitted therapies are initiated, study drug must be discontinued.

In Case of Severe AE or Overdose

There are no special emergency procedures to be followed. While there is no specific antidote to Compound 114, symptomatic therapies to reverse its effects are widely available and should be applied.

All concomitant, and/or rescue therapies will be recorded on the appropriate pages of the electronic Case Report Form (eCRF).

Restrictions

Restrictions Regarding Concomitant Treatment

Mitigation of the potential risks can be achieved by close monitoring of patients and the prohibited co-administration of drugs with a similar mechanism of action (i.e., activators of the NO-sGC-cGMP pathway). Special caution is warranted when administering Compound 114 in combination with NTI and/or sensitive CYP3A4 substrates, because the exposure of such drugs may potentially increase in a clinically relevant manner. In addition, Compound 114 must not be co-administered with OATP1B1/3 inhibitors and drugs known to inhibit or induce UGT enzymes, as this may impact Compound 114 exposures in a clinically relevant manner. A list of relevant drugs can be found in the ISF.

In addition, therapies with a known risk of TdP must not be co administered with Compound 114. These restrictions apply from screening (Visit 1) throughout the study including treatment period and follow up period until EOS Visit. In the event of temporary concomitant use of such a therapy, trial treatment must be temporarily stopped and can then be re-started after a period of at least 5 half-lives after the concomitant therapy with the known risk of TdP has been stopped, as long as the interruption rules are followed.

Table 4 summarizes the medications and therapies which must not be taken for the time periods as specified.

TABLE 4

| Restricted medications | | | |
|---|---|---|---|
| | Prior to randomization | During treatment period | After EOT, follow-up period |
| Immunomodulating/Immunosuppressive agents | | | |
| Anakinra | NOT permitted 1 week prior Visit 2 | NOT permitted except for deterioration/rescue | permitted |

TABLE 4-continued

| Restricted medications | Prior to randomization | During treatment period | After EOT, follow-up period |
|---|---|---|---|
| Etanercept | NOT permitted 2 weeks prior Visit 2 | NOT permitted except for deterioration/rescue | permitted |
| Cyclophosphamide, cyclosporine A, sirolimus, colchicine, D-penicillamine, mizoribine or intravenous immunoglobulin | NOT permitted 4 weeks prior Visit 2 | NOT permitted except for deterioration/rescue | permitted |
| Hydroxychloroquine, tacrolimus | NOT permitted 4 weeks prior Visit 2 | NOT permitted | NOT permitted |
| Infliximab, certolizumab, golimumab, adalimumab abatacept, tocilizumab, brodalumab, leflunomide | NOT permitted 8 weeks prior Visit 2 | NOT permitted except for deterioration/rescue | permitted |
| Rituximab or other anti-CD20 antibodies | NOT permitted 6 months prior Visit 2 | NOT permitted | permitted |
| Non-investigational or investigational cell-depleting therapies, including but not limited to alemtuzumab, anti-CD4, anti-CD5, anti-CD3, anti-CD19 | NOT permitted 18 months prior Visit 2 | NOT permitted | NOT permitted |
| Chlorambucil, bone marrow transplantation, or total lymphoid irradiation | NOT permitted | NOT permitted | NOT permitted |
| Thalidomide, antithymocyte globulin, plasmapheresis, or extracorporeal photopheresis | NOT permitted | NOT permitted | NOT permitted |
| Corticosteroids | | | |
| Oral prednisone >10 mg/day or equivalent[1] | NOT permitted 2 weeks prior Visit 2 | NOT permitted | permitted |
| Intravenous and intramuscular corticosteroids[1] | NOT permitted 2 weeks prior Visit 2 | NOT permitted | permitted |
| Other restricted medications | | | |
| Nitrates[2] or NO donors (e.g. amyl nitrate) in any form, including topical; phosphodiesterase (PDE) 5 (PDE5) inhibitors (e.g. sildenafil, tadalafil, vardenafil); and nonspecific PDE5 inhibitors (theophylline, dipyridamole) | NOT permitted 2 weeks prior to Visit 2 | NOT permitted | NOT permitted |
| Prostacyclin analogues (oral beraprost for digital ulcers/Raynaud's disease and short-term/intermittent therapy of up to 21 days with intravenous prostacyclin analogues for digital/vascular lesions is allowed) | NOT permitted 2 weeks prior to Visit 2 | NOT permitted | permitted |
| Nintedanib, pirfenidone, terguride, tyrosine-kinase inhibitors (e.g. imatinib, nilotinib, dasatinib), janus-kinase inhibitors | NOT permitted 2 weeks prior to Visit 2 | NOT permitted | permitted |
| sGC-stimulators/activators (other than Compound 114) | NOT permitted 4 weeks prior to Visit 2 | NOT permitted | NOT permitted |
| Treatment with clinically relevant OATP1B1/3 | NOT permitted 4 weeks prior | NOT permitted | permitted |

TABLE 4-continued

| Restricted medications | | | |
|---|---|---|---|
| | Prior to randomization | During treatment period | After EOT, follow-up period |
| inhibitors and clinically relevant UGT inhibitors/ inducers as provided in the Investigator Site File (ISF) | to Visit 2 | | |
| Drugs with known risk of Torsade de Pointes | NOT permitted 5 half-lives prior to Visit 2 | NOT permitted | NOT permitted |
| Other investigational drugs | NOT permitted 1 month or 5 half-lives (whichever is greater) prior Visit 2 | NOT permitted | NOT permitted |
| Other restricted therapies | | | |
| Ultraviolet phototherapy | NOT permitted 6 weeks prior to Visit 2 | NOT permitted | permitted |
| Herbal or natural products (Including Traditional Chinese Medicine) | Recommended to be stopped. Should not be initiated at or after screening. If used at a stable dose prior to screening may be continued. | Initiation not permitted. If used at a stable dose prior to screening may be continued. | Initiation not permitted. If used at a stable dose prior to screening may be continued. |

[1]To treat non-SSc-related conditions such as asthma or allergy/anaphylaxis allowed according to Investigator's judgment.
[2]In case a sublingual nitrate is needed for suspected acute coronary syndrome, when the patient is on trial treatment, close monitoring of the blood pressure is required.

Restrictions on Diet and Lifestyle

Patients should be fasted for at least 8 hours prior to collection of safety laboratory samples, starting from Visit 2.

Contraception Requirements

WOCBP trial participants, must use a highly effective method of birth control throughout the trial, and for a period of at least 7 days after last trial drug intake, if their sexual partner is a male able to father a child. No contraceptive is required for the WOCBP participant's partner.

Highly effective methods of birth control per ICH M3 (R2) that results in a low failure rate of less than 1% per year when used consistently and correctly include (examples depending on approval status in each country):

- Combined (estrogen and progestogen containing) hormonal birth control that prevents ovulation (oral, intravaginal, transdermal).
- Progestogen-only hormonal birth control that prevents ovulation (oral, injectable, implantable).
- Intrauterine device or intrauterine hormone-releasing system.
- Bilateral tubal occlusion.

A male trial participant must be vasectomised with documented absence of sperm or use a condom until at least 7 days after last trial drug intake, if their sexual partner is a WOCBP.

No contraceptive is required for the male participant's partner.

Alternatively, WOCBP participants and male participants able to father a child must abstain from male-female sex. This is defined as being in line with the preferred and usual lifestyle of the patient. Periodic abstinence e.g. calendar, ovulation, symptothermal, post-ovulation methods; declaration of abstinence for the duration of exposure to trial drug; and withdrawal are not acceptable.

Assessments

Assessment of Efficacy

Forced Vital Capacity

Spirometry measurements will be performed according to ATS/ERS 2019 guideline. B. L. Graham et al., "American Thoracic Society, European Respiratory Society. Standardization of spirometry 2019 update: an official American Thoracic Society and European Respiratory Society technical statement," Am J Respir Crit Care Med 2019; 200(8): e70-e88. The FVC will be assessed using standardized spirometry equipment which will be provided centrally with supplies of pre-calibrated disposable flow sensors. These sensors meet International Organization for Standardization (ISO) 26782 standards, but with a maximum permissible accuracy error of ±2.5%, in accordance with the ATS/ERS Technical Statement. As such there is no need to conduct daily calibration prior to use. Only these spirometers are to be used for this trial. Spirometry will be conducted with the subject in a seated position. It is preferable that the same trained individual performs the PFTs for a given subject. The best of three efforts will be defined as the highest FVC obtained on any of three blows meeting the 2019 ATS/ERS criteria (with a maximum of eight attempts). Predicted normal values will be calculated according to Global Lung Initiative.

Efforts should be made, to schedule the spirometric measurements at approximately the same time of the day, with reference to baseline measurement (Visit 2). On days of clinic visits, patients must refrain from strenuous activity at least 12 hours prior to PFT. Smoking should be discouraged throughout the visit days (clinic visit) and will not be permitted in the 30-minute period prior to spirometry. Patients should also avoid cold temperatures, environmental smoke, dust, or areas with strong odors (e.g. perfumes). If treated with bronchodilators, wash-out of 24 hours for long acting and 8 hours for short acting bronchodilators should be observed before spirometry.

In case of decline in FVC % predicted of ≥15% (relative) from baseline, this should be confirmed by another FVC test within a month. If diagnosis of ILD had not been established by HRCT obtained at screening, a new HRCT of the chest should be performed to confirm ILD.

Spirometry results will be electronically transmitted. To ensure the quality of primary endpoint measurement a central spirometry review is put in place to provide feedback to the investigational site and the CRA on the quality of the data received from the site.

Further instructions regarding FVC measurements will be provided in the ISF.

Modified Rodnan Skin Score

The mRSS consists of an evaluation of patient's skin thickness rated by clinical palpation using a 0-3 scale (0=normal skin; 1=mild thickness; 2=moderate thickness; 3=severe thickness with inability to pinch the skin into a fold) for each of 17 surface anatomic areas of the body: face, anterior chest, abdomen, (right and left separately) fingers, forearms, upper arms, thighs, lower legs, dorsum of hands and feet. These individual values are added and the sum is defined as the total skin score. D. Khanna et al., "Scleroderma Clinical Trials Consortium, World Scleroderma Foundation. Standardization of the modified Rodnan skin score for use in clinical trials of systemic sclerosis," J Scleroderma Rel Disord 2017; 2(1):11-18.

This assessment should be performed by a physician who is experienced and trained in skin scoring. It should be attempted that the skin scoring is performed by the same rater for a given patient throughout the trial in order to prevent inter-observer variability Further instructions regarding mRSS assessment will be provided in the ISF.

Diffusing Capacity for Carbon Monoxide

The site will use its own DLCO equipment and conduct all measurements with the same DLCO equipment (e.g. if several devices would be available at the site). Single-breath DLCO will be carried out according to the ATS/ERS guideline on DLCO measurements. N. Macintyre et al., "Standardisation of the single-breath determination of carbon monoxide uptake in the lung," Eur Respir J 2005; 26(4): 720-735. Before beginning the test, the maneuvers should be demonstrated and the patient carefully instructed.

DLCO values will be adjusted for the most recent haemoglobin value. For predicted normal values, different sites may use different prediction formulas, based on the method used to measure DLCO. In any case, the calculation method used must comply with the ATS/ERS guideline on DLCO measurements and the prediction formula appropriate for that method. Raw data (gas mixture, equation used for prediction of normal, further adjustments made if so) must be traced.

The DLCO assessment should be performed after the FVC assessment and should always be started approximately the same time a day i.e. with <90 minutes maximum difference between start of the tests.

Further instructions regarding DLCO measurements will be provided in the ISF.

Oxygen Saturation Measurement

Oxygen saturation (SPO2) will be measured at rest by standard pulse oximetry (unaffected skin of earlobe or forehead) and the recorded value will be entered in eCRF.

Digital Ulcer Net Burden

Digital ulcer net burden is defined as the total number of "active" and indeterminate digital ulcers at an assessment. Digital ulcers are defined according to proposed WSF (World Scleroderma Foundation) definition: "Loss of epidermal covering with a break in the basement membrane (which separates dermis from epidermis). It appears clinically as visible blood vessels, fibrin, granulation tissue and/or underlying deeper structures (e.g. muscle, ligament, fat) or as it would appear on debridement." Y. A. Suliman et al., "Defining skin ulcers in systemic sclerosis: Systematic literature review and proposed World Scleroderma Foundation (WSF) definition, J Scleroderma Relat Disord 2017; 2(2): 115-1204.

Ulcer count will ideally be performed by the same healthcare professional at every visit.

Further instructions regarding DU assessment will be provided in the ISF

Raynaud's Attacks Assessment (Composite Measure of RP Activity)

Raynaud's attacks will be assessed using the composite of the following 6 individual outcome measures to minimize the measurement variability and placebo response: Raynaud's condition score (RCS), patient assessment of RP, physician assessment of RP, attack symptoms, duration of attacks, and average number of attacks per day as described in H. Gladue et al., "Evaluation of test characteristics for outcome measures used in Raynaud's phenomenon clinical trials" Arthritis Care & Res. 2013: 65(4):630-636.

The RCS is a daily patient self-assessment of RP activity using a 0 to 10 ordinal scale from 'no difficulty' to 'extreme difficulty'. It incorporates the cumulative frequency, duration, severity and impact of RP attacks, reflecting the overall degree that RP has affected use of the patient's hands. See P. A. Merkel et al., "Scleroderma Clinical Trials Consortium. Measuring disease activity and functional status in patients with scleroderma and Raynaud's phenomenon," Arthritis Rheum 2002; 46(9):2410-2420.

The RCS, details of the frequency and duration of Raynaud's attacks, and attack symptoms of pain, numbness and tingling, each represented by a 0 to 100 VAS, will be incorporated into the daily diary that patients will be asked to complete for 7 consecutive days leading up to the visits.

The patient and physician assessment measures the severity of RP in the past week using a 0 to 100 VAS will be assessed at visits.

Tendon Friction Rubs

Anatomical sites including the hands, wrists, elbows, shoulders, knees and ankles will be examined for the presence or absence of tendon friction rubs.

Tender and Swollen Joint Count

This physician-reported tool evaluates 28 joints for swelling and tenderness. This outcome measure should be performed by the same physician to assess the burden of joint disease from SSc-associated polyarthritis and myopathy.

Questionnaires and Derived Outcomes

The patient should complete PRO questionnaires on his/her own in a quiet area/room prior to any other trial-related examination. Site personnel will check the answers of the patients in the questionnaires for completeness prior to the patient leaving the site, but the response to each item should not be scrutinized. In instances where a patient cannot give or decide upon a response, no response should be recorded. The scores will then be transcribed into the eCRF by designated site-personnel.

Functional Assessment of Chronic Illness Therapy-Fatigue

The FACIT-Fatigue Scale is a 13-item measure that assesses self-reported fatigue and its impact upon daily activities and function. M. Hinchcliff et al., "Validity of two new patient-reported outcome measures in systemic sclerosis: Patient-Reported Outcomes Measurement Information System 29 item Health Profile and Functional Assessment of Chronic Illness Therapy-Dyspnea short form," Arthritis Care Res (Hoboken) 2011; 63(11):1620-1628.

Health Assessment Questionnaire-Disability Index (HAQ-DI)

The HAQ is a questionnaire that has been used frequently in rheumatological disorders including Systemic Sclerosis, assessing function/activities of daily living with 20 items in 8 categories, namely dressing and grooming, hygiene, arising, reach, eating, grip, walking, and common daily activities. See J. Pope, "Measures of systemic sclerosis (scleroderma)," Arthritis Care Res (Hoboken) 2011; 63(Suppl 11):S98-S111; and B. Bruce et al, "The Health Assessment Questionnaire (HAQ)," Clin Exp Rheumatol 2005; 23(Suppl 39):S14-S18.

Each category has at least two sub-category questions. Within each category, patients report the amount of difficulty they have in performing the specific sub-category items. There are four response options ranging from No Difficulty to Unable to Do, scored 0-3. A global score (the HAQ disability index, or HAQ-DI) will be calculated from the category scores.

Scleroderma Health Assessment Questionnaire

The SHAQ includes the HAQ-DI and 6 additional VASes of relevance to patients with Systemic Sclerosis. V. D. Steen et al., "The value of the Health Assessment Questionnaire and special patient-generated scales to demonstrate change in systemic sclerosis patients over time," Arthritis Rheum 1997; 40(11):1984-1991.

The 6 additional VASes of relevance to patients with Systemic Sclerosis are pain, a patient global assessment of limitation, vascular involvement, DUs, lung involvement and gastrointestinal involvement. Scores from these scales are not incorporated into the overall score of the HAQ-DI.

The SHAQ will be self-administered by the patient at visits. Detailed further instructions regarding the SHAQ administration to the patient and scoring is provided in the ISF.

EuroQol 5-Dimensional Quality of Life Questionnaire

The EQ-5D was developed by the European Quality of Life (EuroQol) Group and is a standardised instrument for use as a measure of health outcome. M. Herdman et al., "Development and preliminary testing of the new five-level version of EQ-5D (EQ-5D-5L)," Qual Life Res 2011; 20:1727-1736. The version used in this trial is the new five level version (EQ-5D-5L).

The questionnaire essentially consists of 2 pages. The first page is the descriptive system with 5 questions to the patient's health state today. Each question captures one dimension of health (e.g. mobility, self-care) and has five levels to answer. The second page records the patient's self-rated health status of today on a vertical graduated (0 to 100) visual analogue scale.

Patient's and Clinician's Global Assessment

This tool incorporates a self-assessment (PGA VAS) and a clinician assessment (CGA VAS) on the patient's overall health in the prior 1 week using a 0-10 ordinal scale and a rating of overall SSc-related health transition compared with 1 month prior and 1 year prior.

Scleroderma Skin Patient Reported Outcome

The SSPRO is a validated PRO measure that assesses Health Related Quality of Life (HRQOL) related to skin involvement in SSc. A. Man et al., "Development and validation of a patient-reported outcome instrument for skin involvement in patients with systemic sclerosis," Ann Rheum Dis 2017; 76:1374-1380. It has 18 items representing 4 HRQOL scales: physical effects, emotional effects, physical function, and social effects. All items are scored from 0 (better) to 6 (worse).

Worst Pain Numeric Rating Scale

Worst Pain NRS is a horizontal line with an eleven-point numeric range. It is labeled from zero to ten, with zero being an example of someone with no pain and ten being the worst pain possible.

Patient Global Impression of Change (PGI-C)

The Patient Global Impression scale (PGI) is the PRO counterpart to the Clinical Global Impressions scale, (CGI), which was published in 1976 by the National Institute of Mental Health (US). It consists of one item based on the CGI and adapted to the patient. Used as the PGI-C, It mainly measures change in clinical status.

Combined Response Index in Systemic Sclerosis, ACR-CRISS version and revised version The CRISS is a two-step composite index which includes in Step 2 the mRSS, FVC percent predicted, HAQ-DI, patient's global assessment and clinicians' global assessment. Step 1 in the ACR-CRISS version consists of the absence of significant worsening of interstitial lung disease, a new scleroderma renal crisis, left ventricular failure or pulmonary arterial hypertension. D Khanna et al., "The American College of Rheumatology provisional composite response index for clinical trials in early diffuse cutaneous systemic sclerosis," Arthritis Rheumatol 2016; 68(2):299-311. In Step 1, worsening of the ILD is defined as decline in FVC % predicted ≥15% (relative), confirmed by another FVC test within a month, HRCT to confirm ILD—if not already confirmed at screening—and FVC<80% of predicted. Left ventricular failure is defined as left ventricular ejection fraction≤45%, requiring treatment. New PAH should be confirmed by right-sided heart catheterization. Patients who have any of the above are considered not improved and are assigned a probability score of 0.0.

In Step 2 of the ACR-CRISS, a weighted probability score (between 0.0 and 1.0, inclusive) that incorporates absolute changes from baseline in the five core set measures: mRSS, FVC percent predicted, HAQ-DI, patient's global assessment and clinicians's global assessment is calculated.

In the revised version, significant gastrointestinal dysmotility requiring parenteral or enteral nutrition and significant digital ischaemia requiring hospitalization, gangrene or amputation are added to Step 1. D. Khanna et al., "New composite endpoint in early diffuse cutaneous systemic sclerosis: revisiting the provisional American College of Rheumatology Composite Response Index in Systemic Sclerosis," Ann Rheum Dis 2021; 80:641-650. These patients are considered not improved and are not included in Step 2.

In Step 2 of the revised CRISS, the proportion of patients who achieve a defined percentage of improvement in at least 1, 2, 3, 4 or 5 core set measures is assessed.

Global Rank Composite Score (GRCS).

The GRCS is a composite score reflecting how trial participants compare with one another on the basis of a hierarchy of ordered outcomes: death, event-free survival (survival without respiratory, renal, or cardiac failure), FVC, the score on the Disability Index of the Health Assessment Questionnaire, and the modified Rodnan skin score. K. M. Sullivan et al., "Myeloablative autologous stem-cell transplantation for severe scleroderma," N Engl J Med 2018; 378(1):35-47.

EXAMPLES

Example 1

Example 1 describes an experiment that is used to demonstrate inhibition of hypoxia induced TGFβ2 production in primary human microvascular endothelial cells by Compound 114. TGFβ and hypoxia are considered important drivers of vascular remodeling and fibrosis associated with the pathogenesis of SSc.

Materials and Methods

The assay uses the following materials and reagents:

Human dermal microvascular endothelial cells are obtained from (Lonza, 2543).

All experiments are performed with cells between passage 4 and passage 8. Four donors are used in these experiments EBM™-2 (Lonza, 3156 or 00190860)

EGM™-2 MV Singlequots (Lonza, 4147)

FBS (Gibco, A4766801)

Reagent Pack (Lonza, 5034)

Pen/Strep (Gibco, 15140122)

Glutamax (Gibco, 35050061)

T175 flasks (Corning, 431466)

DMSO (Sigma D2650-5×5 ML)

Compound 114 (Sample ID 30295026, Batch 5, mol weight 582.689)

ODQ (Enzo Life sciences, ALX270034M010)

96 well culture plate (Corning Costar 3595)

Hypoxia Chamber (Water jacketed incubator with settings at 37° C. and 1% $O_2$ (Thermo Scientific, 3110)

Media Preparation: Normal culturing Media: EBM-2 is supplemented with EGM-2MV singlequots, 10% Premium Plus FBS, 1% Glutamax and 1% Pen-strep. Basal media: EBM-2 was supplemented with 2% FBS Culturing endothelial cells: Dermal endothelial cells from each of the indicated donors are grown in T175 flasks with normal culturing media in 37° C./5% $CO_2$ incubator. When cells reach 80-90% confluence, cells are subcultured via trypsinization with Trypsin from the reagent pack for five minutes at 37° C. Cells are counted and plated into new T175 for further expansion or plated for the experiment as described in the protocol below.

Preparation of compound: 5.2 mg of Compound 114 is dissolved in 446.2 μL of 100% DMSO at a concentration of 20 mM. The compound solution is then diluted to 10 mM in 100% DMSO. 10 mM of the compound solution is then diluted to 1 mM and 100 mM in 100% DMSO and then secondarily diluted to 100 μM, 10 μM, and 1 μM in HEPES-Tyrode BSA buffer, making a 10× stock.

Hypoxia Assay:

Day 0: Cells are trypsinized, counted and plated such that each well contains 8×103 cells and 100 μl of media and put in an incubator overnight (37° C.)

Day 1: Media is aspirated and replaced with basal media left at 37° C. overnight-24 hours Day 2: Basal media is replaced with 90 μL of fresh basal media.

10 μL of ODQ (12×) is added so that a final concentration of 10 μM (or 3-fold serial dilution) is reached. Plates are incubated 45 minutes at 37° C. Aliquots of the compound solution are added at a 6× concentration 20 μl per well so that the final well volume is 120 μl.

After treatment plates are left in 37° C. Normoxia or 37° C. 1% 02 hypoxia for 48 hrs. Supernatant is collected and TGFβ2 μlevels are measured using MSD ELISA.

MSD Elisa: The MSD ELISA is done according to manufacturer suggested protocol.

Dermal microvascular endothelial cells from three normal donors are plated and grown to confluence. The cells are serum starved and treated with DMSO/ODQ/Compound 114. After DMSO/ODQ/Compound 114 addition, cells are incubated in a Hypoxia Chamber (1% $O_2$). Cells and supernatants are collected after 48 hours and TGFβ2 μlevels are measured by MSD-ELISA. MSD plates are read using the MSD QuickPlex SQ 120 Instrument. Discovery Workbench Version 4.0 is used to determine standard curve and TGF-β2 concentration. Normoxia is used as the control for hypoxia conditions.

Figure 1:
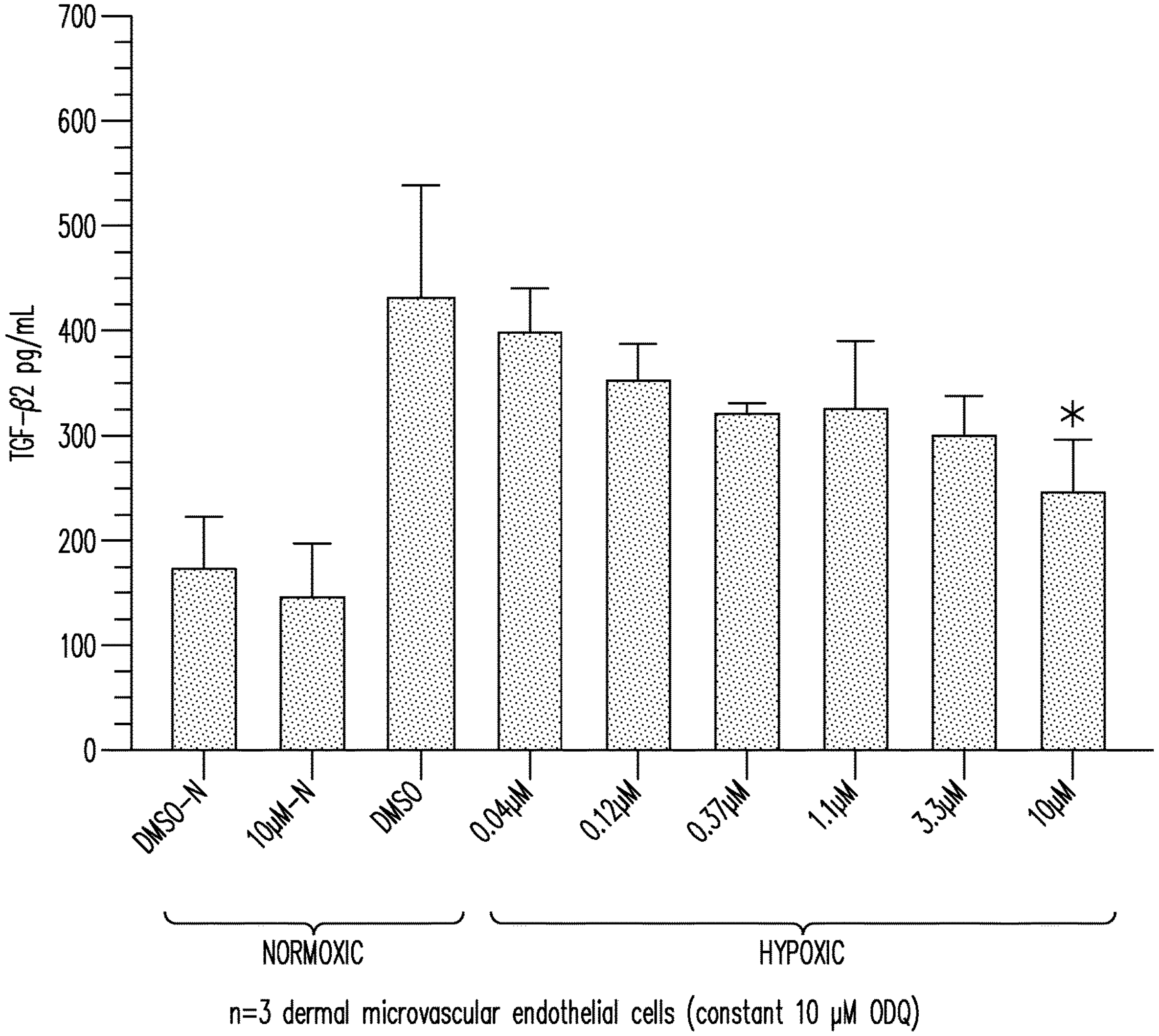
FIG. 1 shows the hypoxia induced TGFb2 production in primary human microvascular endothelial cells by Compound 114.

TGFβ and hypoxia are considered important drivers of vascular remodeling and fibrosis associated with the pathogenesis of SSc. As shown in FIG. 1, elevated levels of TGFβ2 are produced in primary human microvascular endothelial cells in hypoxic conditions (1% $O_2$) compared to normoxic control conditions. Compound 114 inhibits hypoxia-induced TGFβ2 levels in the primary human microvascular endothelial cells.

Using hypoxia (1% $O_2$) as a disease-relevant stimulus, the results demonstrate that elevated levels of TGFβ2 are produced in primary human microvascular endothelial cells in hypoxic conditions compared to normoxic control conditions. The data also demonstrate that sGC activation by Compound 114 reduced hypoxia-driven TGFβ2 production in a concentration-dependent manner in the primary human microvascular endothelial cells derived from 3 donors (see FIG. 1). Statistically significant reduction was achieved with 10 μM Compound 114. Therefore, Compound 114 is expected to provide significant vasculoprotective and anti-fibrotic benefits for patients with SSc by reducing hypoxia mediated endothelial cell activation.

REFERENCES

Yuansheng Gao, J. Usha Raj, fetal neonatal Physiology, 2017

Pyriochou A, Papapetropoulos A. Soluble guanylyl cyclase: more secrets revealed. Cell Signal. 2005 April; 17(4):407-13. doi: 10.1016/j.cellsig.2004.09.008. PMID: 15601619.

Kimberly A. Lucas, Giovanni M. Pitari, Shiva Kazerounian, Inez Ruiz-Stewart, Jason Park, Stephanie Schulz, Kenneth P. Chepenik and Scott A. Waldman. Guanylyl Cyclases and Signaling by Cyclic GMP. Pharmacological Reviews September 2000, 52 (3) 375-414

Dumitrascu R, Weissmann N, Ghofrani H A, Dony E, Beuerlein K, Schmidt H, Stasch J P, Gnoth MJ, Seeger W, Grimminger F, Schermuly R T. Activation of soluble guanylate cyclase reverses experimental pulmonary hypertension and vascular remodeling. Circulation. 2006 Jan. 17; 113(2):286-95.

Beyer C, Reich N, Schindler S C, Akhmetshina A, Dees C, Tomcik M, Hirth-Dietrich C, von Degenfeld G, Sandner P, Distler O, Schett G, Distler J H. Stimulation of soluble guanylate cyclase reduces experimental dermal fibrosis. Ann Rheum Dis. 2012 June; 71(6):1019-26.

Stasch J P, Pacher P, Evgenov O V. Soluble guanylate cyclase as an emerging therapeutic target in cardiopulmonary disease. Circulation. 2011 May 24; 123(20):2263-73.

Example 2

Example 2 shows the therapeutic efficacy of BI sGC Activator in bleomycin-induced lung fibrosis and skin-fibrosis models.

Materials and Methods

Compounds and formulation: Compound: Compound 114 (sample ID 30295026), batch 5 and EX00076637 (EX76637/riociguat), sample ID 17810950, batch 5 are both dissolved in Methylcellulose solution. The concentration is 10 mg/kg, 3 mg/kg and 1 mg/kg in a volume of 0.1 ml p.o. Nintedanib ethanesulfonate is prepared freshly every second day. The concentration is 60 mg/kg in a volume of 0.1 ml p.o.

Bleomycin-Induced Dermal Fibrosis

Skin fibrosis is induced by subcutaneous injections of bleomycin (2.5 mg/kg) every other day for six weeks. To evaluate the effects of therapeutic dosing, fibrosis is first induced by injections of bleomycin for three weeks in the absence of treatment. Thereafter, treatment is initiated, while injections of bleomycin are continued. The outcome is analyzed six weeks after the first injection of bleomycin. Mice injected with 0.9% NaCl, the vehicle of bleomycin, serve as non-fibrotic controls. The following groups with n=8 female C57Bl/6 mice each are analyzed:

- Group 1 NaCl/vehicle
- Group 2 bleomycin/vehicle
- Group 3 bleomycin/nintedanib
- Group 4 bleomycin/Cpd 114 1 mg/kg bid p.o.
- Group 5 bleomycin/Cpd 114 3 mg/kg bid p.o.
- Group 6 bleomycin/Cpd 114 10 mg/kg bid p.o.
- Group 7 bleomycin/EX76637 1 mg/kg bid p.o.
- Group 8 bleomycin/nintedanib+Cpd 114 3 mg/kg bid p.o.
- Group 9 bleomycin/nintedanib+Cpd 114 10 mg/kg bid p.o.

Quantification of dermal thickening: Defined areas of the skin of the upper back are excised, subsequently fixed in 4% formalin for 6 h and embedded in paraffin. Skin sections are cut and stained with hematoxylin/eosin. The dermal thickness (measured as distance between the epidermal-dermal border to the dermal-subcutaneous border in arbitrary units) is quantified in 4 different sections from different sites with 2 measurements per section as described 1,2,4-7. The analysis is performed in a blinded manner.

Detection of myofibroblasts: Myofibroblasts are characterized by the expression of α-smooth muscle actin (αSMA). Fibroblasts positive for αSMA are detected in paraffin-embedded slides from the upper back by incubation with monoclonal anti-αSMA antibodies (clone 1A4, Sigma-Aldrich, Steinheim, Germany). The expression is visualized with horseradish peroxidase labeled secondary antibodies and 3,3-diaminobenzidine tetrahydrochloride (DAB) (Sigma-Aldrich). Monoclonal mouse IgG antibodies (Calbiochem, San Diego, CA, USA) are used for controls 4,8-10. The analysis is performed by a blinded reviewer evaluating the myofibroblasts in four sections per sample.

Hydroxyproline assay: The amount of collagen protein in skin samples is determined via hydroxyproline assay. After digestion of full skin thickness punch biopsies (Ø 3 mm) derived from the upper back in 6 M HCl for three hours at 120° C., the pH of the samples is adjusted to 6 with 6 M NaOH. For lungs, the middle lobe is analyzed. Afterwards, 0.06 M chloramine T is added to each sample and incubated for 20 min at room temperature. Next, 3.15 M perchloric acid and 20% p-dimethylaminobenzaldehyde are added and samples are incubated for additional 20 min at 60° C. The absorbance is determined at 557 nm with a Spectra MAX 190 microplate spectrophotometer using a standard curve generated with purified type I collagen (Sigma-Aldrich).

Bleomycin-Induced Pulmonary Fibrosis

In the model of bleomycin-induced lung fibrosis, fibrosis is induced by a single intratracheal injection of 50 μl bleomycin at day 0. Mice injected with equal volumes of 0.9% NaCl served as controls. The outcome is analyzed after 28 days. Treatment is started at day 15 post intratracheal installation of bleomycin and thus at a timepoint, when fibrosis is already preestablished.

The following groups with n=8 female C57Bl/6 mice each are analyzed:

- Group 1 NaCl/vehicle
- Group 2 bleomycin/vehicle
- Group 3 bleomycin/nintedanib
- Group 4 bleomycin/Cpd 114 1 mg/kg bid p.o.
- Group 5 bleomycin/Cpd 114 3 mg/kg bid p.o.
- Group 6 bleomycin/Cpd 114 10 mg/kg bid p.o.
- Group 7 bleomycin/EX76637 1 mg/kg bid p.o.
- Group 8 bleomycin/nintedanib+Cpd 114 3 mg/kg bid p.o.
- Group 9 bleomycin/nintedanib+Cpd 114 10 mg/kg bid p.o.

Two mice (one from groups 3 and one from group 9) died within the pretreatment phase and are thus not available for analysis.

Histological evaluation of pulmonary fibrosis: Whole lungs are excised, fixed in 4% formalin for 6 h and embedded in paraffin. 5 m sections are cut and stained with Sirius Red. Images are captured using a Hamamatsu nano sumo S60 slide scanner microscope (Hamamatsu, Herrsching am Ammersee, Germany). Histological changes of pulmonary fibrosis are quantified by Ashcroft Scoring. The analysis is performed in a blinded manner. In addition, whole lung sections are stained with Sirius Red (Sigma-Aldrich) and fibrotic area is determined as the percentage of Sirius Red covered area per total area using ImageJ (V. 1.42q, National Institutes of Health, USA) 4, 8, 12, 13.

Missing samples/values: As outlined above, two mice in bleomycin-induced pulmonary fibrosis died and samples are thus not available. In addition, the following values are missing: Ashcroft scoring: 1 sample in the NaCl group (tissue washed off the slide), hydroxyproline lung: 1 sample each for Cpd 114 3 mg/kg, Cpd 114 10 mg/kg and Cpd 114 10 mg/kg+Nintedanib (assay related issues), dermal thickness: 1 mouse each in the Cpd 114 1 mg/kg and Cpd 114 10 mg/kg+Nintedanib (embedding not in perfectly upright position).

Statistics: All data are presented as median ±range, and differences between the groups are tested for their statistical significance by Mann-Whitney U non-parametric test for non-related samples.

Figure 2A:
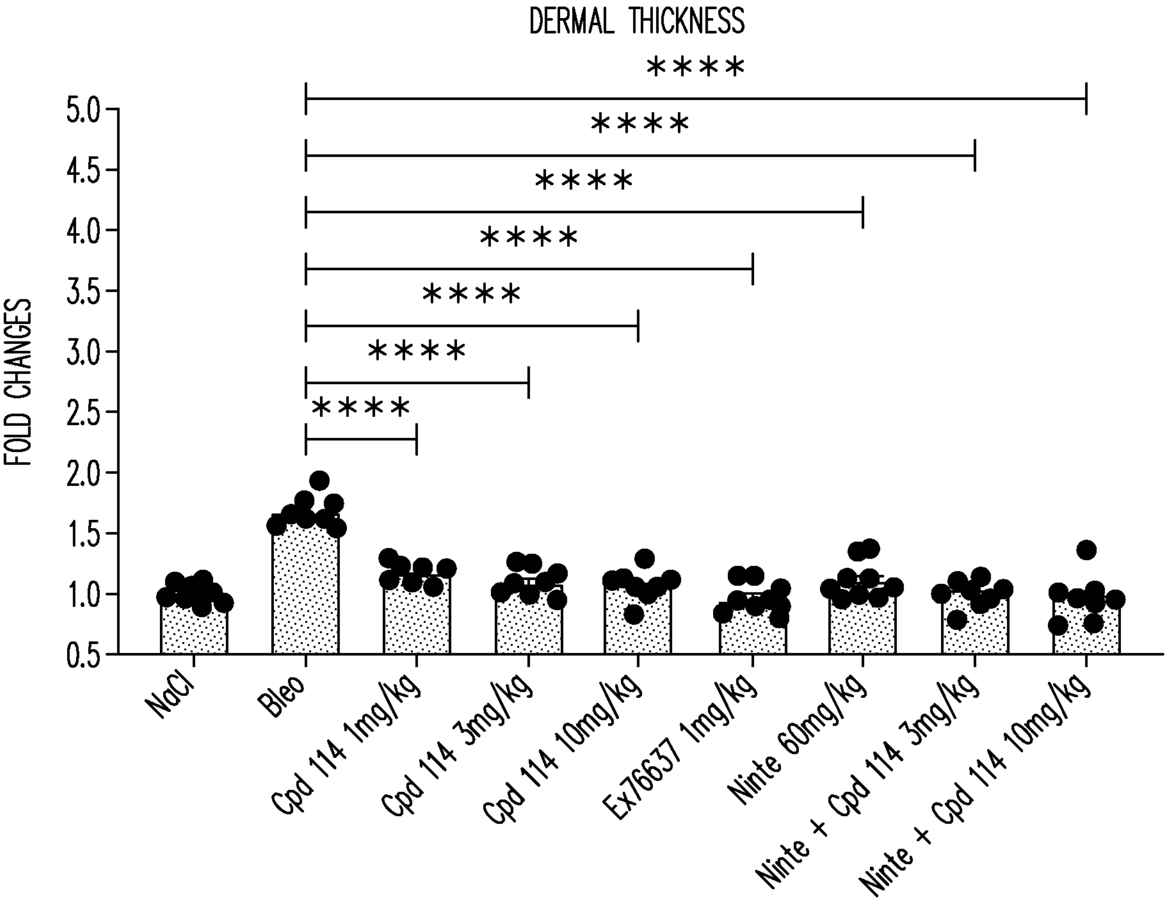
FIGS. 2A-2C show the effect of bleomycin-induced skin fibrosis dermal thickness (FIG. 2A), decreased myofibroblast counts (FIG. 2B) and lower hydroxyproline content (FIG. 2C) as compared to bleomycin/vehicle mice. P-values of less than 0.05 are considered as statistically significant; p-values are expressed as follows: 0.05>p>0.01 as *; 0.01>p>0.001 as , 0.001>p>0.0001 as * and p<0.0001 as ****.
Figure 2B:
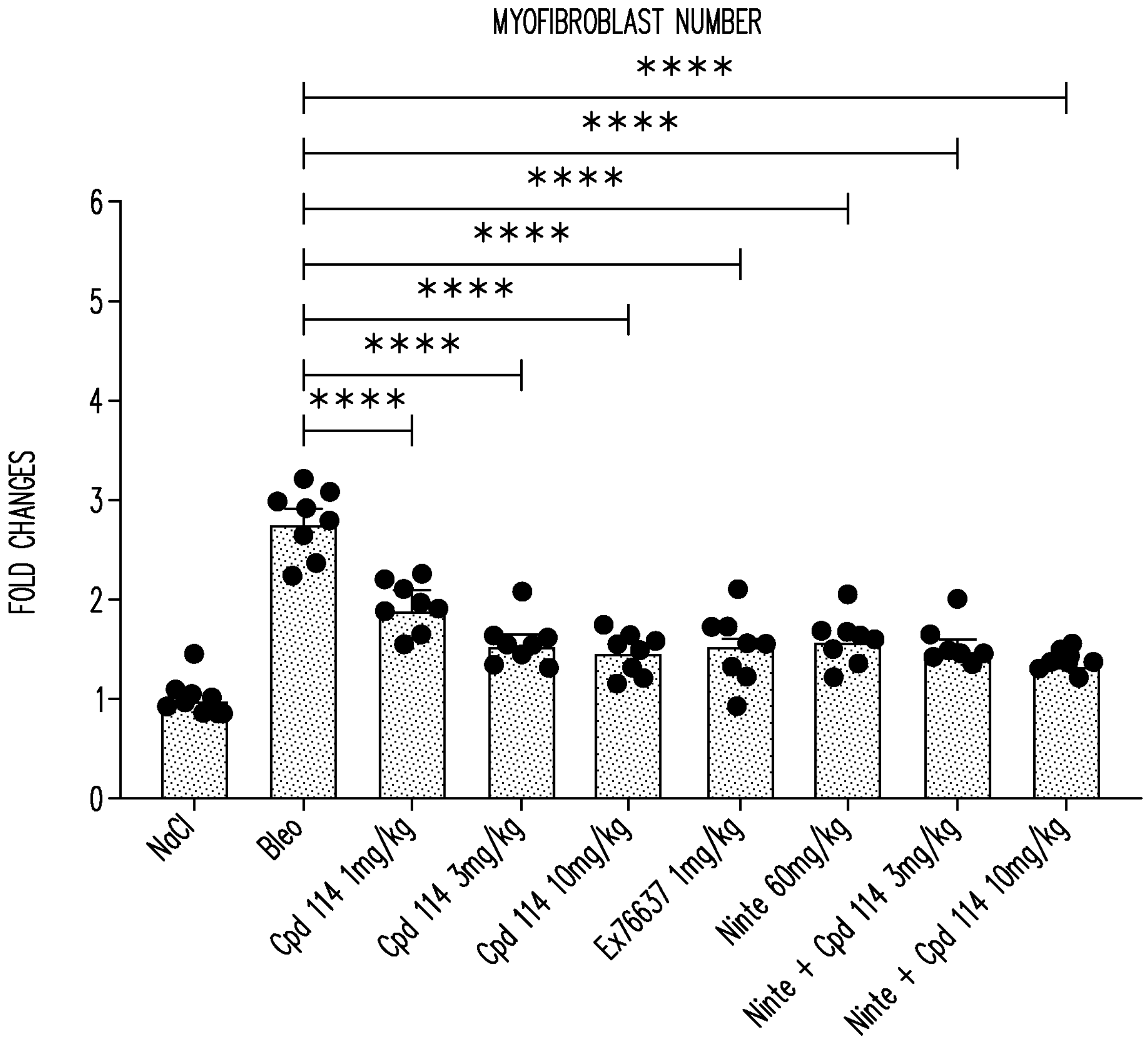
Figure 2C:
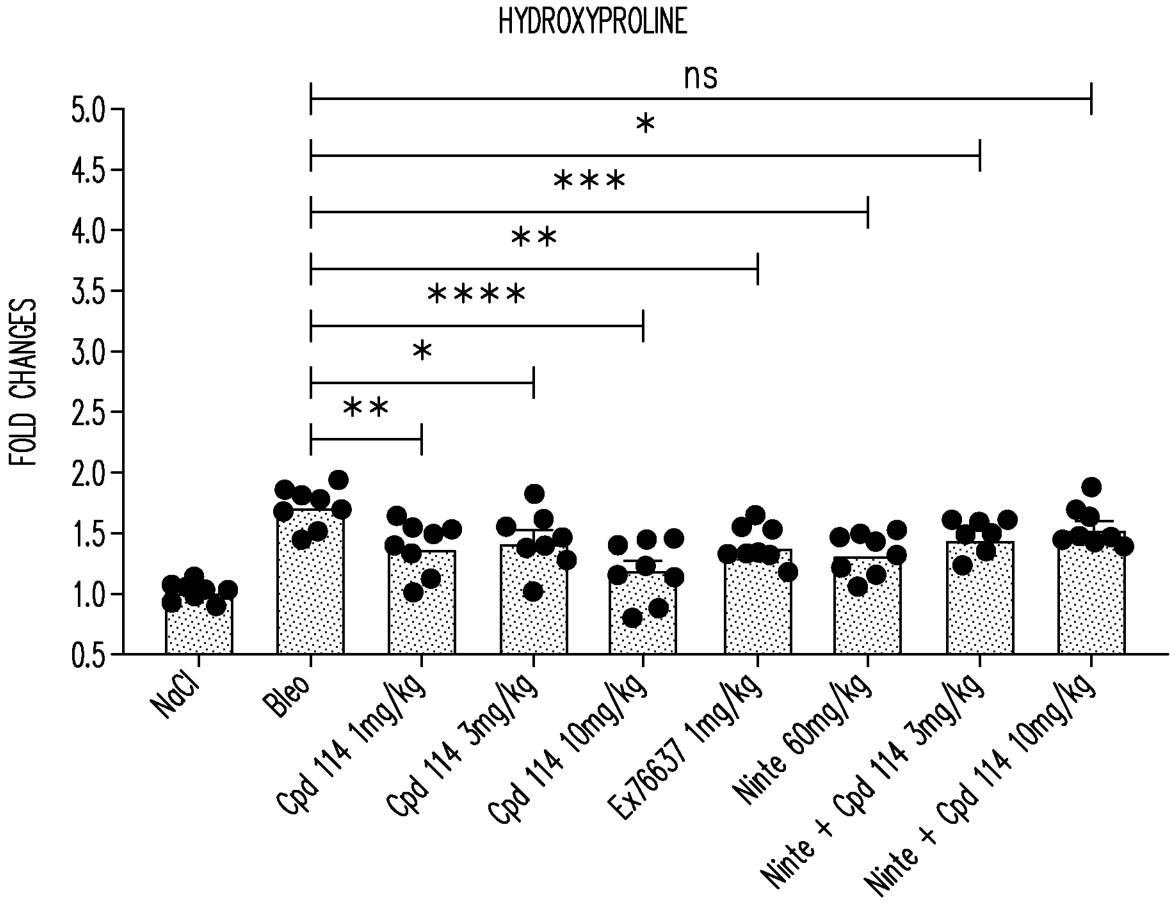

Results: The results show that therapeutic dosing of Compound 114 (Cpd 114) and EX76637 ameliorates bleomycin-induced dermal and pulmonary fibrosis Mice challenged with bleomycin for six weeks (bleomycin/vehicle) developed dermal fibrosis as compared to control mice. As expected, treatment with nintedanib at doses of 60 mg/kg qd for the last three weeks ameliorated bleomycin-induced dermal fibrosis with reduced dermal thickness (FIG. 2A), decreased myofibroblast counts (FIG. 2B) and lower hydroxyproline content (FIG. 2C) as compared to bleomycin/vehicle mice. Treatment with Compound 114 at doses of 1, 3 or 5 mg/kg for the last two weeks also ameliorated bleomycin-induced dermal fibrosis (FIGS. 2A to B). However, no clear dose-dependency was observed despite certain trends for the dermal thickness and myofibroblast counts, eventually because the effects of even the lowest dose are already quite pronounced. The effects are within the range of those observed with nintedanib. EX76637 at doses of 1 mg/kg also ameliorated bleomycin-induced dermal fibrosis and the effects are comparable to those of Compound 114 (FIGS. 2A to B). The combination of nintedanib with Compound 114 in doses of 3 or 10 mg/kg bid was well tolerated and demonstrated antifibrotic effects. However, no additive effects of the combination therapy as compared to monotherapy with either nintedanib or Compound 114 are observed.

Intratracheal instillation of bleomycin induced severe pulmonary fibrosis. Consistent with previous reports, treatment with nintedanib, initiated two weeks after instillation of bleomycin until the end of the experiment, reduced Ashcroft scores (FIG. 3A), the collagen-covered area (FIG. 3B) and the hydroxyproline content (FIG. 3C). Treatment with Compound 114 in doses of 1, 3 or 10 mg/kg also significantly improved the fibrotic readouts. Although there was a tendency towards more pronounced effects with higher doses for the Ashcroft score, the differences did not reach statistical significance. As for bleomycin-induced dermal fibrosis, EX76637 also ameliorated bleomycin-induced pulmonary fibrosis. Combination therapy of nintedanib with Compound 114 demonstrated no increased efficacy as compared to individual monotherapies.

The results show activation of sGC signaling significantly ameliorates bleomycin-induced dermal and pulmonary fibrosis.

REFERENCES

1 Gabrielli, A., Avvedimento, E. V. & Krieg, T. Scleroderma. N Engl J Med 360, 1989-2003, doi:10.1056/NEJMra0806188 (2009).

2 Varga, J. & Abraham, D. Systemic sclerosis: a prototypic multisystem fibrotic disorder. The Journal of clinical investigation 117, 557-567, doi:10.1172/jci31139 (2007).

3 Distler, J. H. et al. Review: Frontiers of Antifibrotic Therapy in Systemic Sclerosis. Arthritis & rheumatology (Hoboken, N.J.) 69, 257-267, doi:10.1002/art.39865 (2017).

4 Akhmetshina, A. et al. Activation of canonical Wnt signalling is required for TGF-beta-mediated fibrosis. Nature communications 3, 735, doi:10.1038/ncomms1734 (2012).

5 Avouac, J. et al. Inactivation of the transcription factor STAT-4 prevents inflammation-driven fibrosis in animal models of systemic sclerosis. Arthritis and rheumatism 63, 800-809, doi:10.1002/art.30171 (2011).

6 Avouac, J. et al. Inhibition of activator protein 1 signaling abrogates transforming growth factor beta-mediated activation of fibroblasts and prevents experimental fibrosis. Arthritis and rheumatism 64, 1642-1652, doi:10.1002/art.33501 (2012).

7 Weingartner, S. et al. Pomalidomide is effective for prevention and treatment of experimental skin fibrosis. Annals of the rheumatic diseases 71, 1895-1899, doi:10.1136/annrheumdis-2012-201784 (2012).

8 Dees, C. et al. Platelet-derived serotonin links vascular disease and tissue fibrosis. The Journal of experimental medicine 208, 961-972, doi:10.1084/jem.20101629 (2011).

9 Dees, C. et al. JAK-2 as a novel mediator of the profibrotic effects of transforming growth factor beta in systemic sclerosis. Arthritis and rheumatism 64, 3006-3015, doi:10.1002/art.34500 (2012).

10 Dees, C. et al. Inhibition of Notch signaling prevents experimental fibrosis and induces regression of established fibrosis. Arthritis and rheumatism 63, 1396-1404, doi:10.1002/art.30254 (2011).

11 Reich, N. et al. Jun N-terminal kinase as a potential molecular target for prevention and treatment of dermal fibrosis. Annals of the rheumatic diseases 71, 737-745, doi:10.1136/annrheumdis-2011-200412 (2012).

12 Chakraborty, D. et al. Activation of STAT3 integrates common profibrotic pathways to promote fibroblast activation and tissue fibrosis. Nature communications 8, 1130, doi:10.1038/s41467-017-01236-6 (2017).

13 Palumbo-Zerr, K. et al. Orphan nuclear receptor NR4A1 regulates transforming growth factor-beta signaling and fibrosis. Nat Med 21, 150-158, doi:10.1038/nm.3777 (2015).

Example 3

Example 3 describes a study used to evaluate the in vitro efficacy of Compound 114 in reducing platelet activation as measured by CXCL4 release. CXCL4 is a chemokine highly expressed by platelets. It is increased in the blood and skin of patients with SSc and associated with progression of lung fibrosis and pulmonary arterial hypertension. NO-sGC-cGMP is a central pathway to keep platelets quiescent. Dysregulation of this pathway could result in increased systemic CXCL4. Accordingly, reducing human platelet activation as measured by CXCL4 release can be used to assess efficacy of a treatment regimen.

Material and Methods

Compound 114 (sample ID: 30295026, batch: 5)
EX0076637 (sample ID: 17810950, batch: 5)
Nintedanib esilate (Boehringer Ingelheim, Manufacture #67653, lot #1078235)
EX0000076 (sample ID: 15614118, batch: 1)
Blood from healthy donor volunteers
Plastic blood collection tubes with sodium citrate (BD biosciences, 363083)
50 ml conical tube (Corning, 430828)
BSA solution, 30% in saline, fatty acid free, aseptically filled (Sigma, A9205)
ADP (Sigma, 01905-250MG-F)
Tyrode's buffer (Sigma, T2397)
HEPES (Gibco, 15630-080)
DMSO (Sigma, D2650)
1 ml deep well plate (Thermo Scientific, 260251)
Sterile 0.22 um PVDF filter plate (Millipore, MAGVS2210)
96 well microplate (Thermo Scientific, 249946)
CXCL4 ELISA kit (Abcam, ab189573 and R&D systems, DPF40)

Buffer preparation: HEPES-Tyrode BSA buffer: Tyrode's buffer supplemented with 0.35% BSA and 5 mM HEPES.

Generating platelet-rich plasma (PRP): Blood is collected from healthy donor volunteers, into plastic sodium citrate tubes. The first two collected tubes are discarded. The remaining blood is processed within 30 mins of blood drawing. The blood is poured into 50 ml conical tubes without exceeding 35 ml per tube and centrifuged at 200×g for 16 minutes at room temperature with acceleration set at half of maximum speed and deceleration off. After centrifugation, the top layer (PRP) is carefully transferred to a new tube by avoiding the buffy coat. The PRP is rested at room temperature for 5-15 minutes. The PRP is then ready to use for experiment as described in protocol below.

Preparation of Compound: 5.2 mg of Compound 114 is dissolved in 446.241 of 100% DMSO at a concentration of 20 mM. The compound solution is then diluted to 10 mM in 100% DMSO. 10 mM of the compound solution is then diluted to 1 mM and 100 μM in 100% DMSO and then secondarily diluted to 100 μM, 10 μM, and 1 μM in HEPES-Tyrode BSA buffer, making 10× stock solutions.

Preparation of Compound 114 and EX 76637: 5.2 mg of Compound 114 is dissolved in 446.241 of 100% DMSO at a concentration of 20 mM. 2.3 mg of EX 76637 is dissolved in 109 μl of 100% DMSO at a concentration of 50 mM. The compound solution is then diluted to 10 mM in 100% DMSO. 10 mM of the compound solution is then diluted to 1 mM and 100 M in 100% DMSO and then secondarily diluted to 100 μM, 10 μM, and 1 μM in HEPES-Tyrode BSA buffer, making 10× stock solutions.

Preparation of nintedanib: 2.9 mg of nintedanib is dissolved in 446.3 μl of 100% DMSO at a concentration of 10 mM. The compound solution is then diluted to 100 μM in 100% DMSO. 100 μM of the compound solution is then diluted to 1 M in HEPES-Tyrode BSA buffer, making 10× stock solutions.

Preparation of EX 00000776 (MMF): 2.3 mg of EX 00000776 is dissolved in 530.5 μl of 100% DMSO at a concentration of 10 mM. The compound solution is then diluted to 5 mM in 100% DMSO. 5 mM of the compound solution is then diluted to 50 M in HEPES-Tyrode BSA buffer, making 10× stock solutions.

ADP is dissolved in distilled water at concentration of 100 mM. 100 mM ADP are further diluted in HEPES-Tyrode BSA buffer to 10 mM and then secondarily diluted to 100 μM in HEPES-Tyrode BSA buffer, making a 10× stock.

Activation of PRP by ADP and CXLC4 Detection by ELISA

Eighty or forty microliters of PRP is added into a well of a 1 ml deep well plate containing 560 μl or 280 μl of HEPES-Tyrode BSA buffer. Eighty or forty microliters of the 10× compound solution is added per well and incubated at 37° C./5% $CO_2$ for 30 mins prior to addition of ADP. Eighty or forty microliters of 100 μM ADP is added per well and the plate incubated at 37° C./5% $CO_2$ for 5 mins. After 5 minutes of incubation, 300 microliters per well of stimulated PRP is transferred to a sterile 0.22 um PVDF 96-well filter plate. A 96 well microplate is placed under the filter plate to collect supernatant after centrifugation at 1100 rpm for 5 mins. Flow-through supernatant is collected and diluted 1:50 in Sample diluent NS from the Abeam CXCL4 ELISA kit or diluted 1:4 in Calibrator Diluent RD6-13 from R&D systems CXCL4 Quantikine ELISA kit. The CXCL4 ELISA is performed as per vendor's instruction.

Data Analysis

Raw data are generated from Victor Nivo plate reader and analyzed with Microsoft Excel 2016. A standard curve is generated by using XLfit 5.5.0 model 205. The concentration of CXCL4 in the sample is determined by interpolating the absorbance values against the standard curve. The resulting value is multiplied by 50 or 4 (dilution factor) to obtain the concentration of CXCL4 in the sample. The CXCL4 percentage of Max is calculated by concentration values of samples divided by the concentration values of DMSO/ADP and then multiplied by 100.

Results

PRP generated from fresh blood is stimulated with 10 μM ADP with or without the addition of 10 μM, 1 μM, 0.1 μM of Compound 114 or DMSO for 5 minutes.

Platelets are filtered out by filter plates and supernatant is collected for CXCL4 ELISA. CXCL4 percentage of Max is calculated by values of samples divided by values of DMSO/ADP and multiplied by 100. ADP induced CXCL4 production in all 10 donors tested. Addition of sGC activator 1 μM and 10 μM Compound 114 attenuated the ADP-induced CXCL4 production in all 10 donors. Low dose (0.1 μM) of Compound 114 also reduced ADP-induced CXCL4 production in 9 out of 10 donors (FIG. 4). FIG. 5 shows the percentage of Max of all donors compared to ADP/DMSO. The sGC activator Compound 114 significantly reduced ADP-induced CXCL4 production in a dose-dependent manner.

The results show that very low levels of CXCL4 secretion is observed in PRP without activation. As shown in FIG. 4, ADP-induced CXCL4 secretion is reduced by sGC activator Compound 114. 10 donors of PRP are stimulated with 10 μM ADP with or without addition of 10 μM, 1 μM or 0.1 μM Compound 114 or DMSO. Ex 114=Compound 114. As shown in FIG. 5, sGC activator Compound 114 significantly reduced ADP-induced CXCL4 production in a dose-dependent manner. Moreover, minimal effect on CXCL4 production was observed following treatment with riociguat (EX 76637 and designated as EX 637 in the figure) at doses equivalent to Compound 114. Likewise, nintedanib or MMF treatment was also ineffective. CXCL4 percentage of Max is calculated by values of variables divided by values of DMSO/ADP and then multiplied by 100. All values represent as means; T bars represent standard deviation. Statistical analysis is determined using Paired t-test.

The addition of 10 μM ADP, a known platelet agonist, resulted in release of large amount of CXCL4. The data demonstrates that sGC activation by Compound 114 inhibited agonist-induced CXCL4 release in a concentration dependent manner from PRP from 10 donors. Addition of Compound 114 significantly and dose-dependently attenuates the ADP-induced CXCL4 production in all 10 donors. Minimal to no effect was observed following treatment with riociguat, nintedanib or MMF suggesting that Compound 114 possesses differential activity in CXCL4 release in activated human platelets versus the sGC stimulator riociguat or standards of care.

The results show that platelet activation is associated with fibrosis, inflammation, and microvascular injury. CXCL4, highly produced by activated platelets is found directly correlated with SSc disease activity. Inhibition of CXCL4 release is demonstrated in ADP-activated PRP with the sGC activator Compound 114.

What is claimed is:

1. A method for treating a patient with systemic sclerosis, comprising administering to the patient a therapeutically effective amount of a compound of formula (I),

I

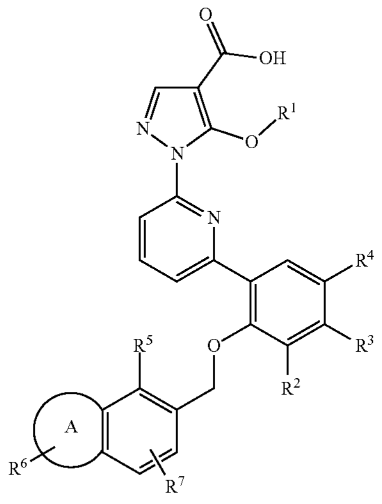

wherein:

A is a 5-7 membered saturated heterocyclyl group containing one nitrogen and optionally one oxygen, wherein one carbon of said heterocyclyl group is optionally substituted with one or two groups selected from $C_{1-3}$alkyl and oxo;

$R^1$ is $C_{1-4}$ alkyl optionally substituted with a methoxy group;

$R^2$ is selected from H, F, Cl, $C_{1-3}$alkyl, —CN, —OMe and —$CF_3$;

$R^3$ is selected from H and —$CH_3$;

$R^4$ is selected from H, F, —$CH_3$ and —OMe;

$R^5$ is selected from H, Cl, —$CH_3$, —$CH_2CH_3$, —$CF_3$, F, and —OMe;

$R^6$ is bonded to the nitrogen on A and is selected from H, $C_{1-6}$alkyl, —$(CH_2)_n$$C_{3-6}$cycloalkyl, —C(O)$C_{1-6}$alkyl, —$(CH_2)_n$ heterocyclyl, —$(CH_2)_n$ aryl —$(CH_2)_n$ heteroaryl, —$SO_2$aryl, $SO_2C_{1-6}$alkyl wherein said $C_{1-6}$alkyl, —$(CH_2)_n$ heterocyclyl, —$(CH_2)_n$ $C_{3-6}$cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH, oxo, —$(CH_2)_{1-3}OH(CH_2)_{2-3}OH$, and —$SO_2CH_3$;

$R^7$ is selected from H, —$CH_3$, —$CH_2CH_3$, —$CF_3$, F, and —CN;

n is 0, 1 or 2 or a pharmaceutically acceptable salt thereof.

2. The method of claim 1, wherein the patient has early diffuse cutaneous systemic sclerosis (dcSSc) and/or vasculopathy.

3. The method according to claim 1, wherein the compound of formula (I) is administered to the patient in an amount selected from the group consisting of 1 mg, 1.5 mg, 2 mg, 2.5 mg, 3 mg, 3.5 mg, 4, mg, 4.5 mg, 5 mg, 5.5 mg, 6 mg, 6.5 mg, 7 mg, 7.5 mg, 8 mg, 8.5 mg, 9 mg, 9.5 mg, and 10 mg.

4. The method according to claim 1, wherein the compound of formula (I) is administered to the patient two times a day (BID) or three times a day (TID).

5. The method according to claim 1, wherein the compound of formula (I) is orally administered to the patient in amount selected from the group consisting of 1 mg, 2 mg, 3 mg, and 4 mg.

6. The method according to claim 5, where the compound of formula (I) is administered to the patient in an amount of 1 mg three times a day (TID), or in an amount of 2 mg TID, or an amount of 3 mg TID, or an amount of 4 mg TID.

7. The method of claim 1, wherein the treatment comprises an initiation treatment comprising administering the compound of formula (I) in an amount of 1 mg three times a day (TID) for weeks one and two; followed by 2 mg TID for weeks 3 and 4 weeks, followed by 3 mg for week 5 until the end of treatment.

8. The method according to claim 1, wherein the amount of the compound of formula (I) is decreased if the patient develops symptomatic orthostatic hypotension.

9. The method according to claim 1, wherein the treatment produces an improvement in:

rate of decline in FVC (mL) over 48 weeks over placebo, change from baseline in mRSS at Week 48, revised CRISS score at Week 48, change from baseline in HAQ-DI score at Week 48, change from baseline in the PGA VAS score at Week 48, change from baseline in the CGA VAS score at Week 48, composite measure of RP activity at Week 48, change from baseline in DU net burden at Week 48, and/or time to treatment failure, defined as the time to one of the following events occurring over the 48-week and extended treatment period selected from the group consisting of:

death, absolute decline in percent-predicted FVC≥10% relative to baseline,

≥25% increase in mRSS and an increase in mRSS of >5 points, and initiation or dose change of immunomodulating/immunosuppressive therapy for clinically significant deterioration of dcSSc.

10. The method according to claim 1, wherein the treatment produces an improvement in:

absolute change from baseline in the FACIT—Fatigue Scale score at Week 48, absolute change from baseline in SSPRO score at Week 48, absolute change from baseline in EQ-5D-5L score at Week 48, absolute change from baseline in Worst Pain NRS at Week 48, absolute change from baseline in the six individual SHAQ domain scores (pain, intestinal problems, respiratory problems, RP, finger ulcers, disease severity) at Week 48, PGIC score at Week 48, change from baseline in DLCO in percent predicted at Week 48, Global Rank Composite Score (GRCS) at the end of the extended treatment period or at the end of the 48-week primary assessment treatment period versus patients who do not participate in the extended treatment period, annual rate of decline in FVC (mL) over the Primary Assessment Treatment Period and extended treatment period change from baseline in presence or absence tendon friction rubs at Week 48, change from baseline in joint involvement at Week 48, and/or absolute change from baseline in RCS at Week 48.

11. The method according to claim 1, wherein the compound of formula (I) has the structure:

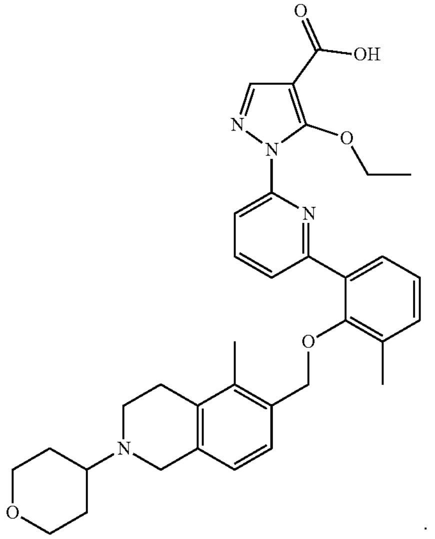 [SMILES: CCOc1c(C(=O)O)cnn1-c1cccc(-c2cccc(C)c2OCc2ccc3c(c2C)CCN(C2CCOCC2)C3)n1]

12. A method for treating a patient with systemic sclerosis, comprising administering to the patient a therapeutically effective amount of a compound having the

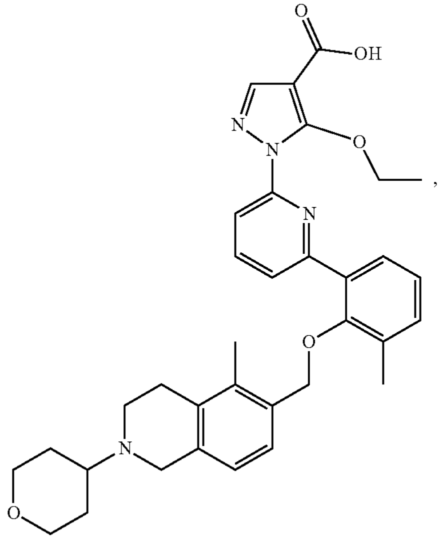 [SMILES: CCOc1c(C(=O)O)cnn1-c1cccc(-c2cccc(C)c2OCc2ccc3c(c2C)CCN(C2CCOCC2)C3)n1]

wherein the compound is orally administered to the patient in amount of amount 1 mg, 2 mg, 3 mg, or 4 mg.

13. The method according to claim 12, wherein the compound is administered to the patient two times a day (BID) or three times a day (TID).

14. The method according to claim 12, where the compound is administered to the patient in an amount of 1 mg three times a day (TID), or in an amount of 2 mg TID, or an amount of 3 mg TID, or an amount of 4 mg TID.

15. The method of claim 12, wherein the treatment comprises an initiation treatment comprising administering the compound in an amount of 1 mg three times a day (TID) for weeks one and two; followed by 2 mg TID for weeks 3 and 4 weeks, followed by 3 mg (TID) for week 5 until the end of treatment.

16. The method according to claim 12, wherein the amount of the compound is decreased if the patient develops symptomatic orthostatic hypotension.

17. The method according to claim 12, wherein the treatment produces an improvement in:

rate of decline in FVC (mL) over 48 weeks over placebo, change from baseline in mRSS at Week 48, revised CRISS score at Week 48, change from baseline in HAQ-DI score at Week 48, change from baseline in the PGA VAS score at Week 48, change from baseline in the CGA VAS score at Week 48, composite measure of RP activity at Week 48, change from baseline in DU net burden at Week 48, and/or time to treatment failure, defined as the time to one of the following events occurring over the 48-week and extended treatment period selected from the group consisting of:

death, absolute decline in percent-predicted FVC ≥10% relative to baseline,

≥25% increase in mRSS and an increase in mRSS of >5 points, and initiation or dose change of immunomodulating/immunosuppressive therapy for clinically significant deterioration of dcSSc.

18. The method according to claim 12, wherein the treatment produces an improvement in:

absolute change from baseline in the FACIT-Fatigue Scale score at Week 48, absolute change from baseline in SSPRO score at Week 48, absolute change from baseline in EQ-5D-5L score at Week 48, absolute change from baseline in Worst Pain NRS at Week 48, absolute change from baseline in the six individual SHAQ domain scores (pain, intestinal problems, respiratory problems, RP, finger ulcers, disease severity) at Week 48, PGIC score at Week 48, change from baseline in DLCO in percent predicted at Week 48, Global Rank Composite Score (GRCS) at the end of the extended treatment period or at the end of the 48-week primary assessment treatment period versus patients who do not participate in the extended treatment period, annual rate of decline in FVC (mL) over the Primary Assessment Treatment Period and extended treatment period change from baseline in presence or absence tendon friction rubs at Week 48, change from baseline in joint involvement at Week 48, and/or absolute change from baseline in RCS at Week 48.

19. The method of claim 12, wherein the patient has early diffuse cutaneous systemic sclerosis (dcSSc) and/or vasculopathy.

20. A method for treating a patient with systemic sclerosis, comprising administering to the patient a compound having the formula:

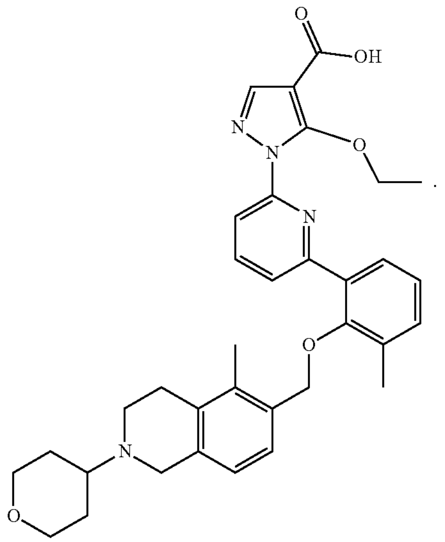 [SMILES: CCOc1c(C(=O)O)cnn1-c1cccc(-c2cccc(C)c2OCc2ccc3c(c2C)CCN(C2CCOCC2)C3)n1]
wherein the compound is administered orally as a pharmaceutical composition comprising 1 mg, 2 mg, 3 mg or 4 mg of the compound.
* * * * *